United States Patent
Tang et al.

(10) Patent No.: US 11,559,497 B2
(45) Date of Patent: Jan. 24, 2023

(54) TRANSDERMAL DRUG DELIVERY SYSTEM FOR KETAMINE

(71) Applicant: Guangzhou Dazhou Biomedicine Ltd., Guangdong (CN)

(72) Inventors: Huadong Tang, McLean, VA (US); Hock S. Tan, East Brunswick, NJ (US); Michael Mayersohn, Marana, AZ (US); Wenfei Liang, Guangdong (CN)

(73) Assignee: GUANGZHOU DAZHOU BIOMEDICINE LTD., Guangzhou (CN)

( * ) Notice: Subject to any disclaimer, the term of this patent is extended or adjusted under 35 U.S.C. 154(b) by 0 days.

(21) Appl. No.: 17/352,006

(22) Filed: Jun. 18, 2021

(65) Prior Publication Data
US 2021/0393544 A1 Dec. 23, 2021

Related U.S. Application Data

(60) Provisional application No. 63/041,489, filed on Jun. 19, 2020.

(51) Int. Cl.
| | |
|---|---|
| *A61K 9/70* | (2006.01) |
| *A61K 47/14* | (2017.01) |
| *A61K 47/12* | (2006.01) |
| *A61K 31/135* | (2006.01) |
| *A61P 25/24* | (2006.01) |

(52) U.S. Cl.
CPC .......... *A61K 9/7061* (2013.01); *A61K 9/7053* (2013.01); *A61K 31/135* (2013.01); *A61K 47/12* (2013.01); *A61K 47/14* (2013.01); *A61P 25/24* (2018.01)

(58) Field of Classification Search
CPC .... A61K 9/7061; A61K 31/135; A61K 47/12; A61K 47/14; A61K 9/7053; A61K 9/7038; A61P 25/24
See application file for complete search history.

(56) References Cited

U.S. PATENT DOCUMENTS 11,191,734 B2 12/2021 Tang et al.

FOREIGN PATENT DOCUMENTS

| | | |
|---|---|---|
| CN | 107847469 A | 3/2018 |
| CN | 109966272 A | 7/2019 |
| CN | 110913844 A | 3/2020 |
| WO | 2006022611 A2 | 3/2006 |
| WO | 2013048453 A1 | 4/2013 |
| WO | 2017003935 A1 | 1/2017 |
| WO | 2018102488 A1 | 6/2018 |

OTHER PUBLICATIONS

International Search Report and Written Opinion for PCT Application No. PCT/IB2021/000413, dated Oct. 27, 2021, 9 pages.

*Primary Examiner* — Shobha Kantamneni
(74) *Attorney, Agent, or Firm* — Nixon & Vanderhye P.C.

(57) ABSTRACT

Provided herein are transdermal delivery devices comprising ketamine, such as monolithic transdermal patches. Also provided herein are methods of preparing transdermal delivery devices. The transdermal delivery device and monolithic patch herein can have various uses, for example, for treating various diseases or disorders, such as depression, anxiety, and/or pain in a subject in need thereof.

9 Claims, 6 Drawing Sheets

Abbreviations: hr = hour; T = duration; wk = week.

TRANSDERMAL DRUG DELIVERY SYSTEM FOR KETAMINE

CROSS REFERENCE TO RELATED APPLICATIONS

This application claims the benefit of U.S. Provisional Application No. 63/041,489, filed Jun. 19, 2020, the content of which is incorporated herein by reference in its entirety.

BACKGROUND

Field of the Invention

In various embodiments, the present invention generally relates to ketamine compositions, transdermal delivery device comprising ketamine, methods of preparation thereof, and methods of using thereof.

Background Art

Major depressive disorder (MDD) is a disabling psychiatric illness. Lifetime prevalence of MDD is approximately 16%. Kessler et al., JAMA, 289(23):3095-105 (2003). There are three primary classes of antidepressants that are commonly prescribed for MDD: (1) monoamine oxidase inhibitors (MAOIs); (2) tricyclics; and (3) serotonin-norepinephrine reuptake inhibitors (SNRIs) and selective serotonin reuptake inhibitors (SSRIs). There are significant limitations with the use of current antidepressants, including limited efficacy, delayed onset of action, and adverse side effects. Antidepressants have been found to be only about 20-30% more effective than placebo. The delay of onset varies from weeks to months, which may result in adverse events, including but not limited to increased vulnerability for suicide, decrease in compliance, and increase in social and economic burden. Common side effects of these antidepressants include nausea, insomnia, anxiety, weight-loss/gain, drowsiness, headache, loss of sex drive, and/or blurred vision. Penn and Tracey, Ther Adv. Psychopharmacol., 2(5): 179-188 (2012).

Recently, clinical and basic biology data have been accumulating to indicate that ketamine may be an effective antidepressant with consistent, rapid and sustained antidepressant effects at low doses (Berman et al., 2000). Unlike conventional antidepressants, which generally take weeks to months to take full effect, ketamine lifts depression in as little as a few hours, and such effects may extend to days after a single subanesthetic-intravenous infusion (Schwartz et al., 2016). Ketamine has been widely used in off-label treatment for MDD, mostly with short-term intravenous infusions (Andrade, 2017; Bobo et al., 2016). Janssen developed an intranasal delivery product of S-ketamine (Spravato), which was approved for treatment resistant depression (TRD) in March of 2019. Intravenous (IV) administration of ketamine, which is being widely used for off-label treatment of depression, presents numerous challenges, including high clinical delivery cost, inconvenience in drug administration, potential unnecessary adverse side effects due to the rapid initial rise in ketamine circulating blood concentrations and relatively high maximum plasma concentrations (Cmax). An intranasal formulation of the S-enantiomer of ketamine has many issues as well, including relatively high Cmax and the consequent side effects, high variability in use or in absorption among subjects, risks of developing nasal rhinitis due to frequent intranasal administration (Singh et al., 2016), and abuse potential (e.g., snorting is the major route of abuse for ketamine among recreational users). It was generally thought that the anesthetic and/or antidepressant effects of ketamine were mainly through the action of S-ketamine, because in vitro S-ketamine has about a 4-fold greater affinity than R-ketamine for NMDA receptor binding (Shimoyama et al., 1999). However, recent animal model studies have suggested that R-ketamine may be more effective as an antidepressant than S-ketamine (Yang et al., 2016). In addition, R-ketamine was shown in animal models to be free of psychotomimetic side effects and abuse liability. Until now, the most abundant data on clinical antidepressant effects are largely from the use of racemic ketamine. Ketamine may be abused by teenagers and adults (Dillon et al., 2003).

Pain can present as a disabling physical illness. One type of pain, neuropathic pain, is a complex chronic pain state often accompanied by tissue injury. The occurrence of pain with neuropathic characteristics is about 6.9-10% of the general population. Hecke et al., Pain, 155(4):654-62 (2014). Symptoms of neuropathic pain include spontaneous burning, shooting pain, hyperalgesia, and allodynia. Patients with neuropathic pain often have conditions that are associated with other significant health issues, including depression, sleep problems, and loss of independence. Bouhassira et al., Pain, 136(3):380-7 (2008). Neuropathic pain can be caused by a variety of mechanisms, including infection, central or peripheral nerve injury, stroke, multiple sclerosis, diabetes mellitus, sarcoidosis, toxic agents (e.g., alcohol, chemotherapy), inherited or genetic neuropathy, and Complex Regional Pain Syndrome (CRPS). CRPS is an intractable form of pain, often resistant to a variety of conventional therapies. Correll et al., Pain Med., 5(3):263-75 (2004). Neuropathic pain is difficult to treat, with only about 40-60% of patients achieving partial relief. Treatment for neuropathic pain includes antidepressants, anticonvulsants, and/or topical pain management medications. Niesters et al., Expert Opin. Drug Metab. Toxicol., 8(11):1409-17 (2012); Dworkin et al., Pain, 132(3):237-51 (2007). Human clinical studies have shown the efficacy of ketamine in the treatment of chronic neuropathic pain. Correll et al., Pain Med. 5(3): 263-75 (2004); Sigtermans et al., Pain, 145(3):304-11 (2009).

Ketamine has been increasingly used as an adjunct in the management of acute perioperative pain. One meta-analysis (Pain medicine, 2015) included clinical trials representing 2,482 patients, 1,403 of whom received ketamine, demonstrating that low-dose IV ketamine reduces opioid consumption by 40% and lowers pain scores. No major complications have been reported with low-dose IV infusion of ketamine when given up to 48 hours after surgery. The dosing paradigm varied from IV bolus during intraoperative only, to IV bolus during intraoperative followed by IV infusion up to 48 hrs. Overall, it appears that, when used in a low-dose range (IV infusion rate less than 1.2 mg/kg/h), a continuous ketamine infusion is not associated with serious side effects.

Posttraumatic stress disorder (PTSD) is a chronic and disabling condition arising after exposure to a severe traumatic event, characterized by persistent reexperiencing, avoidance, and hyperarousal symptoms. Prevalence was reported at about 7.8%, and it occurs at much higher rates for people exposure to interpersonal violence (Kessler R C, Sonnega A, Bromet E, Hughes M, Nelson C B. Posttraumatic stress disorder in the National Comorbidity Survey. Arch Gen Psychiatry. 1995; 52(12):1048-1060.) There have been very few pharmacotherapies available with sufficient efficacy against PTSD. Only 2 FDA-approved SSRIs are indicated for PTSD. There have been no new drugs in >10 years and minimal investment has been made by pharmaceutical industry. Treatment algorithms based largely on clinical opinion and these treatments are associated with significant levels of nonresponse (Jeffreys M, Capehart B, Friedman M J. Pharmacotherapy for posttraumatic stress disorder: review with clinical applications. J Rehabil Res Dev. 2012; 49(5):703-715).

Accumulating evidence for the role of glutamate, the most widely distributed excitatory neurotransmitter, in mediating stress responsivity, the formation of traumatic memories, and the pathophysiology of PTSD, suggests a potential benefit for novel pharmacotherapeutic interventions for this disorder. Recently, ketamine, an antagonist of glutamate NMDA receptor, has emerged as an effective, rapidly acting intervention for MDD patients when administered at sub-anesthetic doses of 0.5 mg/kg for 40 minutes. There have been reported cases that ketamine may be effective for treatment of PTSD (Schönenberg M, Reichwald U, Domes G, Badke A, Hautzinger M. Effects of peritraumatic ketamine medication on early and sustained posttraumatic stress symptoms in moderately injured accident victims. Psychopharmacology (Berl). 2005; 182(3):420-425; McGhee L L, Maani C V, Garza T H, Gaylord K M, Black I H. The correlation between ketamine and posttraumatic stress disorder in burned service members. J Trauma. 2008; 64(2 suppl):S195-S198; Discussion S197-S198; Zeng M C, Niciu M J, Luckenbaugh D A, et al. Acute stress symptoms do not worsen in posttraumatic stress disorder and abuse with a single subanesthetic dose of ketamine. Biol Psychiatry. 2013; 73(12):e37-e38. D'Andrea D, Andrew Sewell R. Transient resolution of treatment-resistant posttraumatic stress disorder following ketamine infusion. Biol Psychiatry. 2013; 74(9):e13-e14). One primary study reported that patients with PTSD who received ketamine experienced significant and greater improvements in depression severity, and experienced significant and greater improvements in PTSD severity, measured by IES-R, compared to active placebo (Feder A, Parides M K, Murrough J W, Perez A M, Morgan J E, Saxena S, et al. Efficacy of intravenous ketamine for treatment of chronic posttraumatic stress disorder: a randomized clinical trial. JAMA Psychiatry. 2014 June; 71(6):681-8).

Despite the wide range of possible indications, existing ketamine formulations and/or methods of treatments have various drawbacks. For example, IV administration of ketamine presents numerous challenges. First, the patient incurs increased costs to receive IV administration. Second, IV administration is inconvenient for the patient, and may lead to reduced compliance. Third, the rapid initial rise in ketamine plasma concentrations following IV administration to the maximum plasma concentration ($C_{max}$) can cause adverse side effects, including drug toxicity, psychotomimetic problems, and increased potential for addiction. Moreover, because ketamine has a short half-life (about 2 hours), this immediate release delivery of ketamine by IV administration may result in little to no ketamine remaining in plasma after about 4 hours, necessitating frequent and repeated dosing to maintain therapeutic plasma levels. Fourth, without additional safeguards, IV administration of ketamine may be susceptible to abuse.

An intranasal formulation of the S-enantiomer of ketamine, Spravato, was approved for TRD. However, intranasal delivery of ketamine presents numerous challenges. It suffers from many of the same immediate release issues faced by IV administration of ketamine: fast time to maximum concentration ($T_{max}$), high $C_{max}$, increased risk of side effects like drug toxicity, and the need for frequent, multiple dosing to maintain therapeutic plasma concentrations. Frequent administration of intranasal ketamine may increase the risk of irritating and damaging the nasal epithelium, which in turn may reduce patient compliance. Also, intranasal administration is associated with high variability in absorption among subjects. Kublik et al., Adv. Drug Deliv. Rev. 29:157-77 (1998). Further, the rapid rise in ketamine plasma concentration following intranasal administration may cause adverse side effects, such as drug toxicity. Moreover, intranasal delivery of ketamine, without additional safeguards, is highly susceptible to abuse. Other routes of administration of ketamine, including parenteral administration of ketamine (e.g., subcutaneous, intramuscular, etc.) suffer from many of these same challenges.

While oral administration (i.e., tablet or capsule) is typically a convenient route for the patient, the metabolic and pharmacokinetic properties of ketamine make oral administration less suitable. Ketamine has a high systemic (primarily hepatic) clearance of about 19 ml/min·kg, a rate which approaches liver plasma flow. Thus, ketamine is subject to substantial pre-systemic metabolism, or first-pass effect, in the liver and gut wall by metabolic enzymes, such as cytochrome P450 enzymes (CYP450). Consequently, the absolute oral bioavailability of ketamine in humans is only about 10-20%. Due to this first-pass effect, there is an increased risk for drug-drug interactions (DDI) with drugs that can inhibit or induce CYP450s. Clements et al., J Pharm Sci, 71(5):539-42 (1981); Fanta, et al., Eur. J. Clin. Pharmacol., 71:441-47 (2015); Peltoniemi et al., Basic & Clinical Pharmacology & Toxicology, 111:325-332 (2012). Moreover, ketamine tablets or capsules are easily abused.

BRIEF SUMMARY

In various embodiments, the present disclosure relates to transdermal delivery devices comprising ketamine. The transdermal delivery devices can be advantageous in many aspects over conventional intravenous infusion or intranasal ketamine delivery. For example, administering ketamine with the transdermal delivery device herein can maintain antidepressant effects while reduce the risk of side effects, which also will lead to improve patient compliance.

Short time infusion (typical 40 min 0.5 mg/kg) of ketamine for treating MDD, widely used off-label, or Janssen's Spravato (a nasal spray of esketamine, approved in 2019) demonstrated large adverse side effects ("AE(s)") and potential of drug abuse and addiction. Spravato is approved with blackbox label, indicating warnings of potential "SEDATION; DISSOCIATION; ABUSE AND MISUSE; and SUICIDAL THOUGHTS AND BEHAVIORS". Because of these serious AEs, a REMS system is mandatory in order to prescribe and administer Spravato to patients. The goal of the REMS is to mitigate the risks of serious adverse outcomes resulting from sedation and dissociation caused by SPRAVATO administration, and abuse and misuse of SPRAVATO by: Ensuring that SPRAVATO is only dispensed and administered to patients in a medically supervised healthcare setting that monitors these patients; Ensuring pharmacies and healthcare settings that dispense SPRAVATO are certified; Ensuring that each patient is informed about the serious adverse outcomes resulting from sedation and dissociation and need for monitoring; Enrollment of all patients in a registry to further characterize the risks and support safe use (FDA REMS for Spravato). Because of the AEs and the resulting REMS system, the medical benefits of SPRAVATO for MDD patients may be significantly limited. As commented by Wilkinson et al (Samuel T. Wilkinson; David H. Howard; Susan H. Busch Psychiatric Practice Patterns and Barriers to the Adoption of Esketamine. JAMA. 2019; 322(11):1039-1040), "Many traditional psychiatric practices may be reluctant to invest in the costly infrastructure necessary to provide this therapy, especially because of the uncertainty regarding the reimbursement of patient monitoring. Patients who do not live near a larger practice that is accepting new patients may have trouble accessing the drug . . . ." On the pharmacology science, nearly all of these major AEs are caused by the rapid increasing ketamine concentrations, thus resulting in a high maximal concentration ($C_{max}$), in about 20-40 mins after nasal spray of Spravato. These side effects start to disappear after about 2-3 hours post dose when the ketamine concentration in circulation drop significantly (SPRAVATO Prescribing Information, the FDA, 2019). Therefore, it is critical in the antidepressant field to separate the AEs and antidepressant effects of ketamine. Unfortunately after a decade since the discovery of ketamine for treatment of MDD, not much effort has been done in clinical studies to understand and minimize the AEs while maintain the antidepressant effects, although hundreds of ketamine clinical trials have been conducted. Among all these trials, most were by short IV infusion, or intranasal, and all these dosing methods resulted in fast absorption to the circulation and central nervous system (CNS), which causes major AEs associated with ketamine as expected.

In light of the above, novel ketamine formulations and/or methods of using thereof are still needed. In particular, the major side effects, including dissociative effects, dizziness, nausea, sedation, vertigo, blood pressure elevation, etc. which occur in a large percentage of patients (such as ~70% with Spravato as an antidepressant), regardless of the indications, pose great limits and concerns of application of ketamine. One objective of the present disclosure is to provide a novel method of using ketamine for these unmet medical needs with minimized side effects, lower cost, and reduced abuse potential, while maintaining the efficacies.

As detailed herein, in various embodiments, the present disclosure provides a transdermal delivery device of ketamine (ketamine patch) for solving these critical issues of ketamine by separating the AEs from the antidepressant effects of ketamine. The transdermal delivery device herein can achieve the antidepressant effects and minimize AEs, in part due to its capability to deliver a large amount of ketamine in a slow and controllable manner, such as the capability to deliver ketamine from hours to up to 3 days with a relative constant rate. The ketamine transdermal patch herein can deliver ketamine to the circulation in a controllable manner, thus, can provide a pronged exposure profile with much lower $C_{max}$ than that observed from other approaches used so far. While similar PK profile as described herein may be achievable, for example, through long time IV infusion, it is very difficult and not practical as it is a high invasive approach, and requires intensive care in a clinical setting. The transdermal patch herein offers a noninvasive with minimal interference to the patients. Further, prior to this disclosure, there was no clinical data to show that lowering the $C_{max}$ and prolonging the exposure can minimize the AEs while maintaining the antidepressant effects.

Certain embodiments of the present disclosure are directed to a transdermal delivery device comprising ketamine. As detailed herein, it was discovered that it is possible to prepare a transdermal delivery device with a desired ketamine flux, which is also stable under storage conditions for 6 months or longer, such as 12 months, 18 months, 24 months, 30 months, or longer. This and other advantageous effects make the transdermal delivery devices herein particularly suitable as medical products for treating or preventing the various diseases and disorders described herein.

The transdermal delivery device typically comprises a backing layer, a drug-in-adhesive layer, and a release liner. The drug-in-adhesive layer typically includes ketamine, a skin permeation enhancer, a crystallization inhibitor, an antioxidant, and a pressure sensitive adhesive. Typically, the drug-in-adhesive layer comprise: a) ketamine in an amount of about 12-18% by weight; b) a skin permeation enhancer in an amount of about 5-15% by weight; c) a crystallization inhibitor in an amount of about 15-25% by weight; d) an antioxidant in an amount of about 0.01-2% by weight; and e) a pressure sensitive adhesive in an amount of about 40-65% by weight. The transdermal delivery device is typically storage stable, e.g., for 1, 3, or 6 months, and up to 30 months or longer. In some embodiments, the transdermal delivery device can be characterized by a ketamine flux rate of about 0.1-1 mg/cm$^2$/day when tested in vitro using human cadaver skin. In some embodiments, a method of preparing the transdermal delivery device is also provided herein.

In some embodiments, the transdermal delivery device is a monolithic patch. In some embodiments, the monolithic patch can have an active surface area of about 10 cm$^2$ to about 180 cm$^2$, such as about 20 cm$^2$, about 40 cm$^2$, about 60 cm$^2$, about 80 cm$^2$, about 90 cm$^2$, about 100 cm$^2$, about 120 cm$^2$, or about 180 cm$^2$. In some embodiments, the monolithic patch includes about 15 mg to about 300 mg of ketamine, such as about 24.7 mg, about 49.6 mg, about 87.3 mg, about 100 mg, about 112.5 mg, about 124.7 mg, about 150 mg, or about 225 mg of ketamine. One monolithic patch typically delivers a dose of ketamine at a rate of about 4 mg/day to about 72 mg/day. Suitable other ingredients and characteristics include any of those described herein in any combination.

The transdermal delivery devices and monolithic patches herein can have various uses, for example, for treating various diseases or disorders described herein, such as depression, anxiety, and/or pain in a subject in need thereof.

Some specific embodiments of the present disclosure are directed to methods of treating depression (e.g., major depressive disorder, treatment resistant depression, or bipolar depression). In some embodiments, the method comprises transdermally administering to a subject in need thereof a therapeutically effective amount of ketamine. In some embodiments, the therapeutically effective amount of ketamine is a dose of about 15 mg to about 250 mg of ketamine, typically delivered over a duration of about 24 hours. In some embodiments, the therapeutically effective amount of ketamine is delivered to the subject by administering a transdermal delivery device herein, such as the monolithic patches herein. As discussed herein, it was found that administering one single dose of about 15 mg to about 150 mg of ketamine over about 24 hours can have a sustained effect in treating depression for about 2 or 3 days or more, such as a week. Thus, in some embodiments, the methods herein can advantageously administer ketamine to the subject with a less frequent dosing frequency, such as once in at least two or three days, such as once or twice a week, which can improve patient compliance.

Some embodiments of the present disclosure are based in part on the novel pharmacokinetic (PK) profile achieved herein as well as the associated pharmacodynamic (PD) effects. For example, the antidepressant effects, following a single dose of ketamine via administering the ketamine transdermal patches over about 24 hours, were relative prolonged and lasted an entire week, which are more sustained compared with those observed from single doses of ketamine by IV infusion or intranasal spray. As also detailed herein, it was found that the baseline MADRS score dropped from stage 1 to stages 2 and 3 of the clinical study, which indicates that the antidepressant effects from administering the ketamine transdermal patches were also a long-term effect, which were present even after ketamine or metabolites are completely cleared in the body. Moreover, studies of individual plasma concentrations of ketamine and its metabolite hydroxynorketamine (HNK) and the antidepressant effects around the $T_{max}$ demonstrated a PK/PD correlation. Based on such correlation, some embodiments of the present disclosure are directed to providing higher doses of ketamine and/or higher concentrations of ketamine and/or HNK for treating depression.

Based in part on the observed PK and PD herein, some embodiments of the present disclosure provide various novel methods of treating depression (e.g., major depressive disorder, treatment resistant depression, or bipolar depression) in a subject in need thereof. In some embodiments, the method comprises administering to the subject a therapeutically effective plasma concentration of ketamine, hydroxynorketamine, and norketamine. In some embodiments, the method comprises administering to the subject a transdermal delivery device comprising ketamine, and administering to the subject a placebo transdermal delivery device, wherein the placebo transdermal delivery device is substantially the same as the transdermal delivery device comprising ketamine, except that the placebo transdermal delivery device does not contain ketamine. In some embodiments, the method comprises administering to the subject a transdermal delivery device comprising ketamine to transdermally deliver a dose of about 20 mg to about 120 mg, such as about 60 mg to about 120 mg of ketamine, such as about 100 mg of ketamine to the subject, for example, over about 24 hours. In some embodiments, the method comprises administering to the subject transdermal delivery device comprising ketamine to transdermally deliver a sufficient amount of ketamine to the subject to achieve a $C_{max}$ of ketamine of about 5-50 ng/mL such as about 20-30 ng/ml and/or a $C_{max}$ of hydroxynorketamine of about 5-50 ng/mL such as about 20-30 ng/ml. In some embodiments, the method is characterized by a dosing frequency ranging from once a day to once a week, more preferably, 1-3 times per week, such as once or twice a week. In some embodiments, each dose of ketamine is administered by applying the transdermal delivery device to the subject for a duration of about 24 hours. In some embodiments, the method is also characterized by having no or minimal adverse effects associated with ketamine, including no or minimal dizziness, sedation, dissociative effects, blood pressure elevations, etc. In some embodiments, the method does not require a REMS program, e.g., it is not necessary to ensure that the ketamine patch herein is only dispensed and administered to patients in a medically supervised healthcare setting that monitors these patients; it is not necessary to ensure pharmacies and healthcare settings that dispense the ketamine patch herein are certified; it is not necessary to ensure that each patient is informed about the serious adverse outcomes resulting from sedation and dissociation and need for monitoring; it is not necessary to ensure enrollment of all patients in a registry to further characterize the risks and support safe use. In some embodiments, the method herein does not require close monitoring of the subject in a medically supervised healthcare setting.

In some embodiments, a method is also provided for screening or selecting a candidate transdermal delivery device for treating depression (e.g., major depressive disorder, treatment resistant depression, or bipolar depression). In some embodiments, the method comprises (1) determining a ketamine flux profile of the candidate transdermal delivery device, (2) optionally administering the candidate transdermal delivery device to a subject, and (3) optionally selecting the candidate transdermal delivery device that provides any of the ketamine flux profile and/or PK profile described herein, such as a mean $C_{max}$ of ketamine of about 5-50 ng/mL such as about 20-30 ng/ml and/or a $C_{max}$ of hydroxynorketamine of about 5-50 ng/mL such as about 20-30 ng/ml.

In some embodiments, the present disclosure provides:

[1] A transdermal delivery device comprising a drug-in-adhesive layer, wherein the drug-in-adhesive layer comprises:
 (a) ketamine in an amount of about 12-18% by weight;
 (b) a skin permeation enhancer in an amount of about 5-15% by weight;
 (c) a crystallization inhibitor in an amount of about 15-25% by weight;
 (d) an antioxidant in an amount of about 0.01-2% by weight; and
 (e) a pressure sensitive adhesive in an amount of about 40-65% by weight.

[2] The transdermal delivery device of [1], wherein the skin permeation enhancer in the drug-in-adhesive layer comprises oleyl oleate and levulinic acid, wherein the weight ratio of oleyl oleate and levulinic acid is about 2:1 to 1:2.

[3] The transdermal delivery device of [1] or [2], wherein the crystallization inhibitor is a vinyl pyrrolidone polymer such as polyvinyl pyrrolidone-co-vinyl acetate (e.g., Kollidon VA64).

[4] The transdermal delivery device of any one of [1]-[3], wherein the antioxidant is a phenol antioxidant, such as butylated hydroxytoluene (also named 3,5-Di-tert-butyl-4-hydroxytoluene).

[5] The transdermal delivery device of any one of [1]-[4], wherein the pressure sensitive adhesive is a polyacrylate adhesive, such as polyacrylate-vinylacetate copolymer, for example, a carboxylate-functionalized polyacrylate-vinylacetate copolymer, e.g., Duro Tak 87-2677.

[6] A transdermal delivery device comprising a drug-in-adhesive layer, wherein the drug-in-adhesive layer comprises:
 (a) ketamine in an amount of about 14-17% by weight;
 (b) oleyl oleate and levulinic acid, each in an amount of about 4-7% by weight;
 (c) a vinyl pyrrolidone polymer in an amount of about 15-25% by weight;
 (d) a polyacrylate copolymer in an amount of about 45-55% by weight; and optionally
 (e) an antioxidant in an amount of about 0.01-1% by weight.

[7] A transdermal delivery device comprising a drug-in-adhesive layer, wherein the drug-in-adhesive layer comprises:
 (a) ketamine in an amount of about 14-17% by weight;
 (b) oleyl oleate and levulinic acid, each in an amount of about 4-7% by weight;
 (c) a polyvinyl pyrrolidone-co-vinyl acetate in an amount of about 15-25% by weight;

(d) a polyacrylate-vinylacetate copolymer in an amount of about 45-55% by weight; and optionally
(e) an antioxidant in an amount of about 0.01-1% by weight.

[8] A transdermal delivery device comprising a drug-in-adhesive layer, wherein the drug-in-adhesive layer comprises:
(a) ketamine in an amount of about 14-17% by weight;
(b) oleyl oleate and levulinic acid, each in an amount of about 4-7% by weight;
(c) a polyvinyl pyrrolidone-co-vinyl acetate in an amount of about 15-25% by weight;
(d) a carboxylate-functionalized polyacrylate-vinylacetate copolymer in an amount of about 45-55% by weight; and optionally
(e) an antioxidant in an amount of about 0.01-1% by weight.

[9] A transdermal delivery device comprising a drug-in-adhesive layer, wherein the drug-in-adhesive layer comprises:
(a) ketamine in an amount of about 15% to about 16%, such as about 15.7% by weight;
(b) oleyl oleate and levulinic acid, each in an amount of about 5-6% by weight;
(c) a polyvinyl pyrrolidone-co-vinyl acetate in an amount of about 20-25% by weight;
(d) a carboxylate-functionalized polyacrylate-vinylacetate copolymer in an amount of about 50-55% by weight; and
(e) an antioxidant in an amount of about 0.3-0.7%, such as about 0.5% by weight.

[10] The transdermal delivery device according to any of [1]-[9], wherein the drug-in-adhesive layer is substantially homogenous.

[11] The transdermal delivery device according to any of [1]-[10], wherein the drug-in-adhesive layer is substantially free of ketamine particles or crystals, e.g., after the transdermal delivery device is stored at room temperature (25±2° C.) at 60% relative humidity (RH)±5% RH for about 6 months or longer, e.g., about 6 months, about 12 months, about 18 months, about 24 months, about 30 months, or longer, or at 40±2° C. at 75% relative humidity (RH)±5% RH for about 1 month, about 3 months, about 6 months, or longer.

[12] The transdermal delivery device according to any of [1]-[11], which is storage stable for about 3 months, about 6 months, about 12 months, about 18 months, about 24 months, about 30 months, or longer, when stored at room temperature at 60% relative humidity (RH)±5% RH, or storage stable for about 1 month, about 3 months, about 6 months, or longer when stored at 40±2° C. at 75% relative humidity (RH)±5% RH.

[13] The transdermal delivery device according to any of [1]-[12], which has an active surface area of about 10 cm$^2$ to about 180 cm$^2$.

[14] The transdermal delivery device according to any of [1]-[13], which has a total ketamine load of about 0.5 mg/cm$^2$ to about 2 mg/cm$^2$.

[15] The transdermal delivery device according to any of [1]-[14], which has a ketamine flux of about 0.1-1 mg/cm$^2$/day.

[16] The transdermal delivery device according to any of [1]-[15], which is capable of adhering to the skin of a subject for a period of time ranging from 8 hours to about 168 hours.

[17] The transdermal delivery device of [16], which is capable of continuously delivering ketamine to the subject during the period of time when the transdermal delivery device adheres to the skin of the subject, for example, at a substantially constant rate ranging from about 0.1 mg/cm$^2$/day to about 1 mg/cm$^2$/day.

[18] A transdermal delivery device comprising 1) a backing layer; 2) a drug-in-adhesive layer; and 3) a release liner, wherein the drug-in-adhesive layer comprises:
(a) ketamine in an amount of about 14-17% by weight;
(b) a means for enhancing ketamine flux to a rate of about 0.1-1 mg/cm$^2$/day when tested in vitro using human cadaver skin;
(c) a means for preventing crystallization of ketamine in the drug-in-adhesive layer after the transdermal delivery device is stored at 40° C. at a relative humidity of 75% for a month or longer;
(d) a pressure sensitive adhesive in an amount of about 45-55% by weight; and optionally
(e) an antioxidant in an amount of about 0.01-1% by weight.

[19] A method of preparing an adhesive composition, the method comprising:
(a) mixing ketamine, oleyl oleate, levulinic acid, a vinyl pyrrolidone polymer, a polyacrylate copolymer, and optionally an antioxidant in a solvent to form a homogenous mixture; and
(b) drying the homogenous mixture to remove the solvent, thereby providing the adhesive composition, wherein on a dry basis of the adhesive composition:
  (i) ketamine is in an amount of about 14-17% by weight;
  (ii) oleyl oleate and levulinic acid are each in an amount of about 4-7% by weight;
  (iii) the vinyl pyrrolidone polymer is in an amount of about 15-25% by weight;
  (iv) the polyacrylate copolymer is in an amount of about 45-55% by weight; and
  (v) the optional antioxidant, if present, is in an amount of about 0.01-1% by weight.

[20] The method of [19], wherein the solvent comprises ethyl acetate.

[21] The method of [19] or [20], wherein the polyacrylate copolymer is a polyacrylate-vinylacetate copolymer, preferably, a carboxylate-functionalized polyacrylate-vinylacetate copolymer.

[22] The method of any one of [19]-[21], wherein the vinyl pyrrolidone polymer is a polyvinyl pyrrolidone-co-vinyl acetate (e.g., Kollidon VA64).

[23] The method of any one of [19]-[22], wherein the antioxidant is a phenol antioxidant, such as butylated hydroxytoluene.

[24] The method of any one of [19]-[23], wherein on a dry basis of the adhesive composition:
(a) ketamine is in an amount of about 15-16%, such as about 15.7% by weight;
(b) oleyl oleate and levulinic acid are each in an amount of about 5-6% by weight;
(c) the vinyl pyrrolidone polymer (e.g., polyvinyl pyrrolidone-co-vinyl acetate) is in an amount of about 20-25% by weight;
(d) the polyacrylate copolymer (e.g., polyacrylate-vinylacetate copolymer, preferably, a carboxylate-functionalized polyacrylate-vinylacetate copolymer) is in an amount of about 50-55% by weight; and
(e) the antioxidant is in an amount of about 0.3-0.7%, such as about 0.5% by weight.

[25] The method of any one of [19]-[24], further comprising laminating the adhesive composition on a backing layer, protecting the adhesive surface with a release liner, and die-cutting the laminated adhesive composition into one or more transdermal patches having an active surface area ranging from about 10 cm² to about 180 cm².

[26] The method of [25], wherein the one or more transdermal patches individually have a total ketamine load of about 0.5 mg/cm² to about 2 mg/cm².

[27] The adhesive composition prepared by the method according to any one of [19]-[26].

[28] A transdermal delivery device comprising the adhesive composition of [27].

[29] A method of treating depression in a subject in need thereof, the method comprising transdermally administering to the subject a therapeutically effective amount of ketamine.

[30] The method of [29], wherein the therapeutically effective amount of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours.

[31] The method of [29] or [30], wherein the therapeutically effective amount of ketamine is a dose of about 15 mg to about 30 mg of ketamine.

[32] The method of [29] or [30], wherein the therapeutically effective amount of ketamine is a dose of about 30 mg to about 60 mg (e.g., about 50 mg) of ketamine.

[33] The method of [29] or [30], wherein the therapeutically effective amount of ketamine is a dose of about 60 mg to about 120 mg (e.g., about 100 mg) of ketamine.

[34] The method of [29] or [30], wherein the therapeutically effective amount of ketamine is a dose of about 75 mg to about 150 mg of ketamine.

[35] The method of any one of [29]-[34], comprising administering to the subject a transdermal delivery device comprising ketamine to deliver the therapeutically effective amount of ketamine.

[36] The method of [35], wherein the transdermal delivery device is applied to the subject for a duration of about 24 hours (i.e., the patch-on period is about 24 hours), wherein during the patch-on period, the transdermal delivery device delivers ketamine to the subject at a substantially constant rate.

[37] The method of [36], wherein during the patch-on period, the transdermal delivery device delivers ketamine to the subject at a substantially constant rate ranging from about 0.1 mg/cm²/day to about 1 mg/cm²/day.

[38] The method of any of [35]-[37], wherein the transdermal delivery device is applied to the subject at a dosing frequency ranging from once a day to once a week, preferably, 1-3 times every week, more preferably, once in at least 3 days, such as once a week or twice a week, wherein each application of the transdermal delivery device has a duration of about 24 hours.

[39] The method of any of [35]-[38], wherein the transdermal delivery device is the transdermal delivery device according to any of [1]-[18] and [28].

[40] The method of any of [29]-[39], wherein the depression is selected from major depressive disorder, treatment resistant depression and bipolar depression.

[41] A method of treating depression in a subject in need thereof, the method comprising administering to the subject a therapeutically effective plasma concentration of ketamine, hydroxynorketamine, and norketamine, wherein the therapeutically effective plasma concentration of ketamine, hydroxynorketamine, and norketamine, during the period of 0-96 hours, is characterized by one or more of the following:
(a) a $C_{max}$ of ketamine of about 5-50 ng/mL such as about 10-30 ng/ml and/or a $C_{max}$ of hydroxynorketamine of about 5-50 ng/mL such as about 10-30 ng/ml;
(b) a ratio of area under the curve from 0-96 hours of hydroxynorketamine to ketamine ranging from about 1 to about 3;
(c) a ratio of area under the curve from 0-96 hours of norketamine to ketamine ranging from about 1 to about 2;
(d) a ratio of $C_{max}$ of hydroxynorketamine to ketamine during 0-96 hours ranging from about 0.7 to about 1.5; and
(e) a ratio of $C_{max}$ of norketamine to ketamine during 0-96 hours ranging from about 0.7 to about 1.5.

[42] The method of [41], comprising administering to the subject a transdermal delivery device to deliver the therapeutically effective plasma concentrations of ketamine, hydroxynorketamine, and norketamine.

[43] The method of [41], wherein the transdermal delivery device comprises ketamine and is free of hydroxynorketamine and norketamine.

[44] The method of [42] or [43], wherein the transdermal delivery device is applied to the subject for a duration of about 24 hours (i.e., the patch-on period is about 24 hours), wherein during the patch-on period, the transdermal delivery device delivers ketamine to the subject at a substantially constant rate.

[45] The method of [44], wherein during the patch-on period, the transdermal delivery device delivers ketamine to the subject at a substantially constant rate ranging from about 0.1 mg/cm²/day to about 1 mg/cm²/day.

[46] The method of any of [42]-[45], wherein the transdermal delivery device is applied to the subject at a dosing frequency ranging from once a day to once a week, preferably, 1-3 times every week, more preferably, once in at least 3 days, such as once a week or twice a week, wherein each application of the transdermal delivery device has a duration of about 24 hours.

[47] The method of any of [42]-[46], wherein the transdermal delivery device is the transdermal delivery device according to any of [1]-[18] and [28].

[48] The method of any of [41]-[47], wherein the depression is selected from major depressive disorder, treatment resistant depression and bipolar depression.

[49] A method of treating depression in a subject in need thereof, the method comprising administering to the subject a transdermal delivery device comprising ketamine, and administering to the subject a placebo transdermal delivery device, wherein the placebo transdermal delivery device is substantially the same as the transdermal delivery device comprising ketamine, except that the placebo transdermal delivery device does not contain ketamine.

[50] The method of [49], wherein one or two administrations of the placebo transdermal delivery device follow every one or two administrations of the transdermal delivery device comprising ketamine.

[51] The method of [49] or [50], wherein the first administering is an administration of the transdermal delivery device comprising ketamine.

[52] The method of any of [49]-[51], wherein each administering of the transdermal delivery device comprising ketamine provides a therapeutically effective amount of ketamine to the subject.

[53] The method of [52], wherein the therapeutically effective amount of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours.

[54] The method of [52], wherein the therapeutically effective amount of ketamine is a dose of about 15 mg to about 30 mg of ketamine.

[55] The method of [52], wherein the therapeutically effective amount of ketamine is a dose of about 30 mg to about 60 mg (e.g., about 50 mg) of ketamine.

[56] The method of [52], wherein the therapeutically effective amount of ketamine is a dose of about 60 mg to about 120 mg (e.g., about 100 mg) of ketamine.

[57] The method of [52], wherein the therapeutically effective amount of ketamine is a dose of about 75 mg to about 150 mg of ketamine.

[58] The method of any of [49]-[57], wherein the transdermal delivery device comprising ketamine is applied to the subject for a duration of about 24 hours (i.e., the patch-on period is about 24 hours), wherein during the patch-on period, the transdermal delivery device comprising ketamine delivers ketamine to the subject at a substantially constant rate.

[59] The method of [58], wherein during the patch-on period, the transdermal delivery device comprising ketamine delivers ketamine to the subject at a substantially constant rate ranging from about 0.1 mg/cm$^2$/day to about 1 mg/cm$^2$/day.

[60] The method of any of [49]-[59], wherein the transdermal delivery device comprising ketamine and placebo transdermal delivery device are administered at a frequency ranging from once a day to once a week, preferably, 1-3 times a week, more preferably, once in at least 3 days such as once a week or twice a week, wherein each administration is independently an administration of the transdermal delivery device comprising ketamine or the placebo transdermal delivery device.

[61] The method of any of [49]-[60], wherein the transdermal delivery device comprising ketamine is the transdermal delivery device according to any of [1]-[18] and [28].

[62] The method of any of [49]-[61], wherein the depression is selected from major depressive disorder, treatment resistant depression and bipolar depression.

[63] A method of treating depression in a subject in need thereof, the method comprising administering to the subject a transdermal delivery device comprising ketamine to deliver a maintenance dose of ketamine to the subject, e.g., the subject has received a bolus dose of ketamine administered.

[64] The method of [63], wherein the transdermal delivery device comprising ketamine is administered to the subject at a dosing frequency ranging from once a day to once every week, preferably, 1-3 times every week, more preferably, once in at least 3 days, such as once a week or twice a week, wherein each application of the transdermal delivery device has a duration of about 24 hours.

[65] The method of [63] or [64], wherein administering the transdermal delivery device comprising ketamine provides the maintenance dose of ketamine to the subject.

[66] The method of [65], wherein the maintenance dose of ketamine is about 15 mg to about 250 mg of ketamine, wherein the maintenance dose is delivered to the subject over a period of time ranging from about 8 hours to about 72 hours, preferably, about 24 hours to about 48 hours, such as about 24 hours or about 48 hours.

[67] The method of [65], wherein the maintenance dose of ketamine is about 15 mg to about 30 mg of ketamine.

[68] The method of [65], wherein the maintenance dose of ketamine is about 30 mg to about 60 mg (e.g., about 50 mg) of ketamine.

[69] The method of [65], wherein the maintenance dose of ketamine is about 60 mg to about 120 mg (e.g., about 100 mg) of ketamine.

[70] The method of [65], wherein the maintenance dose of ketamine is about 75 mg to about 150 mg of ketamine.

[71] The method of any of [63]-[70], wherein the transdermal delivery device comprising ketamine is applied to the subject for a duration of about 24 hours (i.e., the patch-on period is about 24 hours), wherein during the patch-on period, the transdermal delivery device comprising ketamine delivers the maintenance dose of ketamine to the subject at a substantially constant rate.

[72] The method of [71], wherein during the patch-on period, the transdermal delivery device comprising ketamine delivers the maintenance dose of ketamine to the subject at a substantially constant rate ranging from about 0.1 mg/cm$^2$/day to about 1 mg/cm$^2$/day.

[73] The method of any of [63]-[72], wherein the transdermal delivery device comprising ketamine is applied to the subject at a dosing frequency ranging from once a day to once a week, preferably, 1-3 times every week, more preferably, once in at least 3 days, such as once a week or twice a week, wherein each application of the transdermal delivery device has a duration of about 24 hours.

[74] The method of any of [63]-[73], wherein the transdermal delivery device comprising ketamine is the transdermal delivery device according to any of [1]-[18] and [28].

[75] The method of any of [63]-[74], wherein the depression is selected from major depressive disorder, treatment resistant depression and bipolar depression.

[76] The method of any of [63]-[75], wherein the bolus dose of ketamine is an intravenous bolus dose or an intranasal bolus dose.

[77] A kit comprising:
(a) one or more substantially the same transdermal delivery devices comprising ketamine; and optionally
(b) one or more substantially the same placebo transdermal delivery device.

[78] The kit of [77], wherein the one or more substantially the same transdermal delivery device comprising ketamine is the transdermal delivery device according to any of [1]-[18] and [28].

[79] The kit of [77] or [78], wherein each of the placebo transdermal delivery devices is substantially the same as each of the transdermal delivery devices comprising ketamine, except that the placebo transdermal delivery device does not contain ketamine.

[80] The kit of any one of [77]-[79], for use in treating a subject in need thereof for a treatment period of one month or more, wherein the kit includes four or more transdermal delivery devices, wherein each transdermal delivery device is independently the transdermal delivery device comprising ketamine or placebo transdermal delivery device, wherein each transdermal delivery device is labeled or organized according to its sequence of administration during the treatment period, preferably, the first administration is an administration of the transdermal delivery device comprising ketamine.

[81] The kit of [80], wherein at least one administration is an administration of the placebo transdermal delivery device.

[82] The kit of [80] or [81], wherein the sequence of administration during the treatment period comprises one or two administrations of the placebo transdermal delivery devices after every one or two administrations of the transdermal delivery device comprising ketamine.

[83] The transdermal delivery device according to any one of [1]-[18] and [28], which is in a form of a monolithic patch, such as a monolithic patch with an active surface area of about 20 cm$^2$, about 40 cm$^2$, about 60 cm$^2$, about 80 cm$^2$, about 90 cm$^2$, about 100 cm$^2$, about 120 cm$^2$, or about 180 cm$^2$, which contains ketamine in the amount of about 24.7 mg, about 49.6 mg, about 87.3 mg, about 100 mg, about 112.5 mg, about 124.7 mg, about 150 mg, and about 225 mg, respectively, which can deliver a dose of ketamine at a rate of about 6-16 mg/day, about 10-30 mg/day, about 20-40 mg/day, about 25-50 mg/day, about 30-60 mg/day, about 35-70 mg/day, about 40-80 mg/day, about 60-110 mg/day, respectively, e.g., for about 1 day, 2 days, or 3 days.

[84] A method of treating depression in a subject in need thereof, the method comprising administering one or more of the monolithic patches of [83] to transdermally deliver a therapeutically effective amount of ketamine to the subject.

[85] The method of [84], wherein the therapeutically effective amount of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours.

[86] The method of [84] or [85], wherein the therapeutically effective amount of ketamine is a dose of about 15 mg to about 30 mg of ketamine.

[87] The method of [84] or [85], wherein the therapeutically effective amount of ketamine is a dose of about 30 mg to about 60 mg (e.g., about 50 mg) of ketamine.

[88] The method of [84] or [85], wherein the therapeutically effective amount of ketamine is a dose of about 60 mg to about 120 mg (e.g., about 100 mg) of ketamine.

[89] The method of [84] or [85], wherein the therapeutically effective amount of ketamine is a dose of about 75 mg to about 150 mg of ketamine.

[90] The method of any one of [84]-[89], wherein the one or more monolithic patches are applied to the subject for a duration of about 24 hours (i.e., the patch-on period is about 24 hours), wherein during the patch-on period, the one or more monolithic patches deliver the therapeutically effective amount of ketamine to the subject at a substantially constant rate.

[91] The method of any one of [84]-[90], wherein the one or more monolithic patches are applied to the subject at a dosing frequency ranging from once a day to once a week, preferably, 1-3 times every week, more preferably, once in at least 3 days, such as once a week or twice a week, wherein each application of the transdermal delivery device has a duration of about 24 hours.

[92] The method of any of [84]-[91], wherein the depression is selected from major depressive disorder, treatment resistant depression and bipolar depression.

[93] The method of any of [29]-[76] and [84]-[92], characterized in that the treated subject has no or minimal adverse effects associated with ketamine, including no or minimal dizziness, sedation, dissociative effects, blood pressure elevations.

[94] The method of any of [29]-[76] and [84]-[93], characterized in that the method is carried out without a risk evaluation and mitigation strategy (REMS) program.

[95] The method of any of [29]-[76] and [84]-[94], characterized in that the method does not require close monitoring of the subject in a medically supervised healthcare setting.

[96] The method of any of [29]-[76] and [84]-[95], further comprising administering one or more additional antidepressant treatments, such as oral antidepressants or another ketamine related antidepressant such as intranasal ketamine treatment.

[97] A method of treating or preventing a disease or disorder chosen from pain (e.g., neuropathic pain, complex regional pain syndrome (CRPS), chronic pain), depression (major depressive disorder, treatment-resistant depression, bipolar depression), restless legs syndrome, a condition associated with spinal cord injury (e.g., autonomic dysreflexia, immune suppression, chronic central neuropathic pain suffering from spinal cord injury, leukocyte apoptosis, splenic atrophy, leucopenia, or combinations thereof), anxiety, bipolar disorder (e.g., childhood-onset bipolar disorder, bipolar depression), stress-induced disorder (e.g., stress-induced affective disorder, stress-induced psychopathology), post-traumatic stress disorder, Alzheimer's dementia, amyotrophic lateral sclerosis, and suicidality, the method comprising transdermally deliver a therapeutically effective amount of ketamine to a subject in need thereof.

[98] A method of treating or preventing a disease or disorder wherein antagonizing NMDA receptors, enhancing synaptic plasticity, and/or enhancing expression of AMPA receptors is beneficial, the method comprising transdermally deliver a therapeutically effective amount of ketamine to a subject in need thereof.

[99] A method of treating or preventing pain, e.g., neuropathic pain, complex regional pain syndrome (CRPS), or chronic pain, the method comprising transdermally deliver a therapeutically effective amount of ketamine to a subject in need thereof.

[100] A method of treating or preventing psychosis, e.g., psychosis associated with Parkinson's disease, Alzheimer's disease, various dementia such as vascular dementia etc., the method comprising transdermally deliver a therapeutically effective amount of ketamine to a subject in need thereof.

[101] The method of [97]-[100], wherein the therapeutically effective amount of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours.

[102] The method of [97]-[101], comprising administering to the subject a transdermal delivery device comprising ketamine to deliver the therapeutically effective amount of ketamine.

[103] The method of [102], wherein the transdermal delivery device is applied to the subject for a duration of about 24 hours (i.e., the patch-on period is about 24 hours), wherein during the patch-on period, the transdermal delivery device delivers ketamine to the subject at a substantially constant rate.

[104] The method of [103], wherein during the patch-on period, the transdermal delivery device delivers ketamine to the subject at a substantially constant rate ranging from about 0.1 mg/cm$^2$/day to about 1 mg/cm$^2$/day.

[105] The method of any of [102]-[104], wherein the transdermal delivery device is applied to the subject at a dosing frequency ranging from once a day to once a week, preferably, 1-3 times every week, more preferably, once in at least 3 days, such as once a week or twice a week, wherein each application of the transdermal delivery device has a duration of about 24 hours.

[106] The method of any of [102]-[105], wherein the transdermal delivery device is the transdermal delivery device according to any of [1]-[18] and [28].

[107] Any of [1]-[106], wherein ketamine is in a racemic form.

[108] Any of [1]-[106], wherein ketamine is a substantially pure S-enantiomer (e.g., with less than 10% R-isomer, less than 5% R-isomer, less than 1% R-isomer, or less than 0.1% R-isomer), a substantially pure R-enantiomer (e.g., with less than 10% S-isomer, less than 5% S-isomer, less than 1% S-isomer, or less than 0.1% S-isomer), or a mixture of S- and R-isomers in any ratio.

It is to be understood that both the foregoing summary and the following detailed description are exemplary and explanatory only, and are not restrictive of the invention herein.

DETAILED DESCRIPTION

Figure 1:
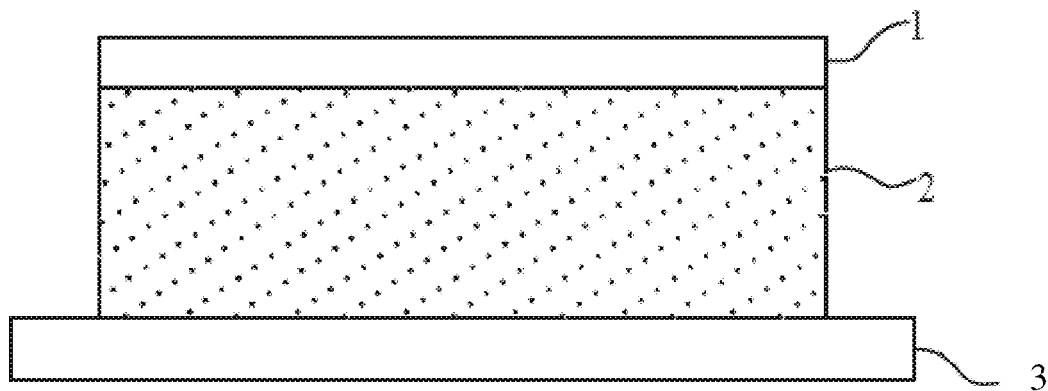
FIG. 1 shows a configuration of a typical drug-in-adhesive patch.

In various embodiments, the present disclosure relates to transdermal delivery devices comprising ketamine. The transdermal delivery device can be advantageous in many aspects over conventional intravenous infusion or intranasal ketamine delivery. For example, administering ketamine with the transdermal delivery device herein can maintain antidepressant effects while reduce the risk of side effects and can improve patient compliance. The current widely used dosage form, 40-min intravenous infusion at 0.5 mg/kg, is not a viable commercial product that can be widely, conveniently and cost-effectively prescribed, as it has many critical issues, such as side effects, abuse potential, high cost and inconvenience. The major side effects of the 40-min IV infusion at 0.5 mg/kg include: psychomimetic effects, dissociative symptoms, elevated blood pressure and/or heart rate (Murrough et al., Am J Psychiatry. 2013 October; 170(10):1134-42). Recently, FDA emphasized publicly on the potential neurotoxicity from ketamine, which was observed in rats (Olney, J. W., et al., Science 244:1360-1362, 1989; Annual Meeting of American Society of Clinical Psychopharmacology, May 29-Jun. 2, 2017). These side effects from the IV dosing were also observed with intranasal administration of ketamine, and such intranasal administration has to be implemented in medical environment, such as in hospitals/clinics with physicians/staff monitoring, thus adding a significant cost to the patients and healthcare.

The transdermal delivery system of embodiments of this disclosure can, at least partially, overcome or minimize these issues by providing a slow rising pharmacokinetic profile with prolonged exposure and a substantially lowered $C_{max}$ (comparing to 40-min infusion or intranasal administration at the same doses). As detailed herein, it is believed that the prolonged exposure can also lead to prolonged antidepressant effects, which can lead to a less frequent dosing frequency. The primary treatment mode involves administration of ketamine via constant rate IV infusion, generally given as a 40-minute infusion of 0.5 mg ketamine/kg. The psychomimetic side effects and the more common dissociative symptoms are noted to occur around 2 hours and disappear quickly after about 4 hours, so are the hemodynamic changes. Ketamine has a short $T_{1/2}$ of about 2 hours.

Therefore, ketamine plasma concentrations are very low at or after 4 hours post-infusion. This correlation of drug concentrations and side effects strongly suggested that these side effects are driven by $C_{max}$. A slow rising pharmacokinetic profile with prolonged exposure and a substantially lower $C_{max}$ of ketamine can therefore significantly reduce risks of these $C_{max}$ driven side effects.

Further, the transdermal delivery device herein can reduce abuse potential. A patch itself is a device that may reduce the abuse potential. The common abuse approaches of ketamine include oral assumption, snorting, and IV/IM injection (U.S. Department of Justice http://www.justice.gov/archive/ndic/pubs4/4769/). To abuse the ketamine in patches, one has to be able to extract the ketamine, which is a significant barrier. Abuse deterrent formulations (ADF) can also be incorporated into the transdermal delivery device herein. Lowered $C_{max}$ with prolonged exposure reduces the dissociative effects, or the "high" feeling, resulting from the high concentration of ketamine, reduces a self-rewarding feedback and thus abuse potential.

Also, the transdermal delivery device herein can reduce potential neurotoxicity with a slow rising pharmacokinetic profile: Olney's paper suggested that the neuro-cytomorphological changes by NMDAR antagonists are mediated by $C_{max}$, rather than total dose or AUC. Prior low dose exposure of NMDAR antagonists could lead to insensitivity of such changes to high exposure (that is, tolerance to neuro-cytotoxicity developed after low exposure). Therefore, the slow-rising concentration can be advantageous by offering insensitivity to neuro-cytotoxicity with low exposure at early times.

In some embodiments, the present disclosure further provides novel transdermal delivery devices and methods of preparing the transdermal delivery devices. The novel transdermal delivery devices typically have a desired ketamine flux and desired adhesive property, which are also stable under storage conditions for 6 months or longer, such as for 12 months, 18 months, 24 months, 30 months, or longer. These and other advantageous effects make the transdermal delivery devices herein particularly suitable as medical products for treating or preventing the various diseases and disorders described herein.

Additionally, in various embodiments, the present disclosure also provides novel treatment methods, e.g., for treating depression, using the transdermal delivery devices herein. The novel treatment methods are based in part on the novel PK/PD results of the present disclosure. The methods herein also provide various advantages over existing ketamine therapies. For example, as detailed herein, the transdermal delivery devices of ketamine (ketamine patch) can separate the AEs associated with ketamine (e.g. dissociation, dizziness, and elevation of blood pressure) from the antidepressant effects of ketamine. As discussed herein, administering representative transdermal delivery devices herein was found to be safe with no or minimal observation for dizziness, sedation, dissociative effects, blood pressure elevations, comparing to about 70-80% prevalence of these AEs with IV infusion or Spravato.

Transdermal Delivery Device Comprising Ketamine

Certain embodiments of the present disclosure are directed to a transdermal delivery device for administering ketamine. The ketamine in the transdermal delivery device described herein is typically in a racemic form. However, the present disclosure is not limited to racemic ketamine. For example, in any of the embodiments described herein, unless otherwise specified or obvious contradictory, the ketamine can be in a racemic form, a substantially pure S-enantiomer (e.g., with less than 10% R-isomer, less than 5% R-isomer, less than 1% R-isomer, or less than 0.1% R-isomer), a substantially pure R-enantiomer (e.g., with less than 10% S-isomer, less than 5% S-isomer, less than 1% S-isomer, or less than 0.1% S-isomer), or a mixture of S- and R-isomers in any ratio. For the avoidance of doubt, the ketamine used in the Examples section is a racemic mixture.

Typically, the transdermal delivery device herein comprises a drug-in-adhesive (DIA) layer. An exemplary configuration of the transdermal delivery device is shown in FIG. 1, which has three main components, a backing layer 1, which is typically an impermeable backing film, a drug-in-adhesive layer 2, which includes an adhesive, ketamine, and other ingredients (e.g., as described herein), the DIA layer may also be referred to herein as adhesive matrix, and a release liner 3, which protects the adhesive surface of the DIA layer prior to use. In some embodiments, the transdermal delivery device is a single layer patch (not counting the backing film and release liner), for example, the single layer includes ketamine homogenously dispersed such as dissolved in the adhesive. In some embodiments, the transdermal delivery device is a multilayer patch. For example, in some embodiments, the transdermal delivery device can include a DIA layer and an additional adhesive matrix or an abuse deterrent layer as described in U.S. Patent Application Publication No. 2018/0353437, the content of which is herein incorporated by reference in its entirety.

The drug-in-adhesive layer typically includes ketamine, a skin permeation enhancer, a crystallization inhibitor, an antioxidant (optional, but typically included), and a pressure sensitive adhesive. In some embodiments, the drug-in-adhesive layer comprise: a) ketamine in an amount of about 12-18% by weight; b) a skin permeation enhancer in an amount of about 5-15% by weight; c) a crystallization inhibitor in an amount of about 15-25% by weight; d) an antioxidant in an amount of about 0.01-2% by weight; and e) a pressure sensitive adhesive in an amount of about 40-65% by weight. To be clear, unless specified otherwise or obviously contradictory from context, the weight percentages of the ketamine, skin permeation enhancer, crystallization inhibitor, antioxidant, and pressure sensitive adhesive herein should be understood as referring to the respective weight percentage based on the final weight of the drug-in-adhesive layer, not including the backing layer and release liner.

Ketamine base is typically used for preparing the drug-in-adhesive layer. In some embodiments, the drug-in-adhesive layer can comprise ketamine in an amount of about 12%, about 13%, about 14%, about 15%, about 16%, about 17%, about 18%, or any range between the recited values, such as about 12-17%, about 13-16%, about 14-17%, about 15-18%, about 15-17%, etc. While the drug-in-adhesive layer typically includes ketamine in an amount ranging from about 12-18%, in some embodiments, it can also include a higher amount of ketamine, such as about 18-20% or about 20-25% or higher than 25% up to 30%. In some embodiments, the drug-in-adhesive layer can also include a lower amount of ketamine, such as about 5-12%, about 10-12%.

The skin permeation enhancer is typically selected such that a desired ketamine flux is reached. In some embodiments, the skin permeation enhancer is present in an amount of about 5%, about 6%, about 7%, about 8%, about 9%, about 10%, about 11%, about 12%, about 13%, about 14%, about 15%, or any range between the recited values such as about 7-15%, about 10-15%, about 8-14%, etc. by weight of the drug-in-adhesive layer. In some embodiments, the skin permeation enhancer comprises oleyl oleate. In some embodiments, the skin permeation enhancer comprises levulinic acid. In some embodiments, the skin permeation enhancer comprises oleyl oleate and levulinic acid. In some embodiments, the skin permeation enhancer comprises oleyl oleate and levulinic acid in a weight ratio ranging from about 2:1 to about 1:2, for example, the weight ratio of oleyl oleate to levulinic acid can range from about 2:1, about 1.5:1, about 1:1, about 1:1.5, or about 1:2, or any ranges between the recited values. In some embodiments, the skin permeation enhancer can further include dimethyl sulfoxide (DMSO). However, it was also discovered that the inclusion of DMSO does not further enhance ketamine permeation from the drug-in-adhesive layer and might even contribute to destabilizing the DIA layer. Accordingly, in some embodiments, the skin permeation enhancer can also be free of DMSO. In some embodiments, the skin permeation enhancer can also comprise one or more other oleyl compounds useful as permeation enhancers, such as oleyl alcohol, oleic acid, etc.

The crystallization inhibitor is typically included in an amount that can stabilize the DIA layer such that no ketamine particles or crystals are formed during storage of a transdermal delivery device comprising the DIA layer, for example, for about 1 month, about 3 months, about 6 months, about 12 months, about 18 months, about 24 months, about 30 months, or longer. In some embodiments, the crystallization inhibitor can be present in the DIA layer in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the crystallization inhibitor comprises a vinyl pyrrolidone polymer, such as polyvinyl pyrrolidone-co-vinyl acetate (e.g., Kollidon VA64).

While optional, the antioxidant is preferably included in the DIA layer. Typically, the antioxidant is included in an amount of less than 2% by weight of the DIA layer. For example, in some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, about 1.5%, about 2%, or any ranges between the recited value such as about 0.1-1%, about 0.3-0.7%, about 0.5-1.5%, etc. by weight of the DIA layer. In some embodiments, the antioxidant can be a phenol based antioxidant, such as butylated hydroxytoluene.

The pressure sensitive adhesive is typically the most abundant component of the DIA layer. For example, in some embodiments, the pressure sensitive adhesive can be in an amount of about 40%, about 45%, about 50%, about 55%, about 60%, about 65%, or any range between the recited values such as about 45-60%, about 45-55%, etc. by weight of the DIA layer. The pressure sensitive adhesive typically comprises a polyacrylate adhesive. In some embodiments, the pressure sensitive adhesive comprises a polyacrylate-vinylacetate copolymer, for example, a carboxylate-functionalized polyacrylate-vinylacetate copolymer (i.e., the polyacrylate-vinylacetate copolymer contains —COOH functional groups), e.g., copolymers of 2-ethyl hexyl acrylate, vinyl acetate, butyl acrylate, acrylic acid, and tert octyl acrylamide, e.g., Duro Tak 87-2677. In some embodiments, the pressure sensitive adhesive comprises a non-reactive polyacrylate copolymer, e.g., copolymers of 2-ethyl hexyl acrylate, methyl acrylate, and tert octyl acrylamide (e.g., described in U.S. Pat. No. 9,056,060), such as Duro Tak 87-900A.

In some embodiments, the present disclosure provides a transdermal delivery device comprising a DIA layer, which comprises:
(a) ketamine in an amount of about 14-17% by weight;
(b) oleyl oleate and levulinic acid, each in an amount of about 4-7% by weight;
(c) a vinyl pyrrolidone polymer in an amount of about 15-25% by weight;
(d) a polyacrylate copolymer in an amount of about 45-55% by weight; and optionally
(e) an antioxidant in an amount of about 0.01-1% by weight.

In some embodiments, the ketamine is in an amount of about 14%, about 15%, about 16%, or about 17% by weight of the DIA layer. In some embodiments, each of the oleyl oleate and levulinic acid is independently present in an amount of about 4%, about 5%, about 6%, or about 7% by weight of the DIA layer. In some embodiments, the vinyl pyrrolidone polymer is a polyvinyl pyrrolidone-co-vinyl acetate such as Kollidon VA-64. In some embodiments, the vinyl pyrrolidone polymer can be present in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the polyacrylate copolymer is a polyacrylate-vinylacetate copolymer, such as Duro Tak 87-2677. In some embodiments, the polyacrylate copolymer is a non-reactive polyacrylate copolymer, such as Duro Tak 87-900A. In some embodiments, the polyacrylate copolymer can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some embodiments, the present disclosure provides a transdermal delivery device comprising a DIA layer, which comprises:
(a) ketamine in an amount of about 14-17% by weight;
(b) oleyl oleate and levulinic acid, each in an amount of about 4-7% by weight;
(c) a polyvinyl pyrrolidone-co-vinyl acetate in an amount of about 15-25% by weight;
(d) a polyacrylate-vinylacetate copolymer in an amount of about 45-55% by weight; and optionally
(e) an antioxidant in an amount of about 0.01-1% by weight.

In some embodiments, the ketamine is in an amount of about 14%, about 15%, about 16%, or about 17% by weight of the DIA layer. In some embodiments, each of the oleyl oleate and levulinic acid is independently present in an amount of about 4%, about 5%, about 6%, or about 7% by weight of the DIA layer. In some embodiments, the polyvinyl pyrrolidone-co-vinyl acetate, such as Kollidon VA-64, can be present in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the polyacrylate-vinylacetate copolymer, such as Duro Tak 87-2677, can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some embodiments, the present disclosure provides a transdermal delivery device comprising a DIA layer, which comprises:
 (a) ketamine in an amount of about 14-17% by weight;
 (b) oleyl oleate and levulinic acid, each in an amount of about 4-7% by weight;
 (c) a polyvinyl pyrrolidone-co-vinyl acetate in an amount of about 15-25% by weight;
 (d) a carboxylate-functionalized polyacrylate-vinylacetate copolymer in an amount of about 45-55% by weight; and optionally
 (e) an antioxidant in an amount of about 0.01-1% by weight.

In some embodiments, the ketamine is in an amount of about 14%, about 15%, about 16%, or about 17% by weight of the DIA layer. In some embodiments, each of the oleyl oleate and levulinic acid is independently present in an amount of about 4%, about 5%, about 6%, or about 7% by weight of the DIA layer. In some embodiments, the polyvinyl pyrrolidone-co-vinyl acetate, such as Kollidon VA-64, can be present in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the carboxylate-functionalized polyacrylate-vinylacetate copolymer, such as Duro Tak 87-2677, can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some embodiments, the present disclosure provides a transdermal delivery device comprising a DIA layer, which comprises:
 (a) ketamine in an amount of about 15-16%, such as about 15.7% by weight;
 (b) oleyl oleate and levulinic acid, each in an amount of about 5-6% by weight;
 (c) a polyvinyl pyrrolidone-co-vinyl acetate in an amount of about 20-25% by weight;
 (d) a carboxylate-functionalized polyacrylate-vinylacetate copolymer in an amount of about 50-55% by weight; and
 (e) an antioxidant in an amount of about 0.3-0.7%, such as about 0.5% by weight.

In some embodiments, each of the oleyl oleate and levulinic acid is independently present in an amount of about 5%, about 5.5%, or about 6% by weight of the DIA layer. In some embodiments, the polyvinyl pyrrolidone-co-vinyl acetate, such as Kollidon VA-64, can be present in an amount of about 20%, about 21%, about 22%, about 23%, about 24%, about 25%, or any range between the recited value such as about 20-22%, by weight of the DIA layer. In some embodiments, the carboxylate-functionalized polyacrylate-vinylacetate copolymer, such as Duro Tak 87-2677, can be in an amount of about 50%, about 51%, about 52%, about 53%, about 54%, about 55%, or any range between the recited values by weight of the DIA layer. In some embodiments, the antioxidant can be a phenol antioxidant, such as butylated hydroxytoluene. In some embodiments, the DIA layer is free of DMSO.

In some embodiments, the present disclosure provides a transdermal delivery device comprising: 1) a backing layer; 2) a drug-in-adhesive (DIA) layer; and 3) a release liner, wherein the drug-in-adhesive layer comprises:
 (a) ketamine in an amount of about 14-17% by weight;
 (b) a means for enhancing ketamine flux to a rate of about 0.1-1 mg/cm$^2$/day when tested in vitro using human cadaver skin;
 (c) a crystallization inhibitor in an amount of about 15-25% by weight;
 (d) a pressure sensitive adhesive in an amount of about 45-55% by weight; and optionally
 (e) an antioxidant in an amount of about 0.01-1% by weight.

In some embodiments, the ketamine is in an amount of about 14%, about 15%, about 16%, or about 17% by weight of the DIA layer. In some embodiments, the DIA layer comprises the means for enhancing ketamine flux to a rate of about 0.1-1 mg/cm$^2$/day when tested in vitro using human cadaver skin, such as to a ketamine flux rate of about 0.1 mg/cm$^2$/day, about 0.2 mg/cm$^2$/day, about 0.3 mg/cm$^2$/day, about 0.4 mg/cm$^2$/day, about 0.5 mg/cm$^2$/day, or about 1 mg/cm$^2$/day, or any range between the recited values, such as about 0.1-0.5 mg/cm$^2$/day, about 0.2-0.5 mg/cm$^2$/day. In some embodiments, the means for enhancing ketamine flux is oleyl oleate (about 5.7% by weight) and levulinic acid (about 5.2% by weight). In some embodiments, the crystallization inhibitor comprises a vinyl pyrrolidone polymer, e.g., a polyvinyl pyrrolidone-co-vinyl acetate such as Kollidon VA-64. In some embodiments, the crystallization inhibitor such as vinyl pyrrolidone polymer can be present in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the pressure sensitive adhesive comprises a polyacrylate copolymer such as a polyacrylate-vinylacetate copolymer, e.g., Duro Tak 87-2677. In some embodiments, the pressure sensitive adhesive such as polyacrylate copolymer comprises a non-reactive polyacrylate copolymer, such as Duro Tak 87-900A. In some embodiments, the pressure sensitive adhesive can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some embodiments, the present disclosure provides a transdermal delivery device comprising: 1) a backing layer; 2) a drug-in-adhesive (DIA) layer; and 3) a release liner, wherein the drug-in-adhesive layer comprises:
(a) ketamine in an amount of about 14-17% by weight;
(b) a skin permeation enhancer in an amount of about 5-15% by weight;
(c) a means for preventing crystallization of ketamine in the drug-in-adhesive layer after the transdermal delivery device is stored at 40° C. at a relative humidity of 75% for a month or longer;
(d) a pressure sensitive adhesive in an amount of about 45-55% by weight; and optionally
(e) an antioxidant in an amount of about 0.01-1% by weight.

In some embodiments, the ketamine is in an amount of about 14%, about 15%, about 16%, or about 17% by weight of the DIA layer. In some embodiments, the skin permeation enhancer comprises levulinic acid. In some embodiments, the skin permeation enhancer comprises oleyl oleate and levulinic acid. In some embodiments, each of the oleyl oleate and levulinic acid is independently present in an amount of about 4%, about 5%, about 6%, or about 7% by weight of the DIA layer. In some embodiments, the DIA layer comprises the means for preventing crystallization of ketamine in the drug-in-adhesive layer after the transdermal delivery device is stored at 40° C. at a relative humidity of 75% for 3 months, 6 months, or longer. In some embodiments, the means for preventing crystallization of ketamine is Kollidon VA64 (about 21.7% by weight). In some embodiments, the pressure sensitive adhesive comprises a polyacrylate copolymer such as a polyacrylate-vinylacetate copolymer, e.g., Duro Tak 87-2677. In some embodiments, the pressure sensitive adhesive such as polyacrylate copolymer comprises a non-reactive polyacrylate copolymer, such as Duro Tak 87-900A. In some embodiments, the pressure sensitive adhesive can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some embodiments, the present disclosure provides a transdermal delivery device comprising: 1) a backing layer; 2) a drug-in-adhesive (DIA) layer; and 3) a release liner, wherein the drug-in-adhesive layer comprises:
(a) ketamine in an amount of about 14-17% by weight;
(b) a means for enhancing ketamine flux to a rate of about 0.1-1 mg/cm$^2$/day when tested in vitro using human cadaver skin;
(c) a means for preventing crystallization of ketamine in the drug-in-adhesive layer after the transdermal delivery device is stored at 40° C. at a relative humidity of 75% for a month or longer;
(d) a pressure sensitive adhesive in an amount of about 45-55% by weight; and optionally
(e) an antioxidant in an amount of about 0.01-1% by weight.

In some embodiments, the ketamine is in an amount of about 14%, about 15%, about 16%, or about 17% by weight of the DIA layer. In some embodiments, the DIA layer comprises the means for enhancing ketamine flux to a rate of about 0.1-1 mg/cm$^2$/day when tested in vitro using human cadaver skin, such as to a ketamine flux rate of about 0.1 mg/cm$^2$/day, about 0.2 mg/cm$^2$/day, about 0.3 mg/cm$^2$/day, about 0.4 mg/cm$^2$/day, about 0.5 mg/cm$^2$/day, or about 1 mg/cm$^2$/day, or any range between the recited values, such as about 0.1-0.5 mg/cm$^2$/day, about 0.2-0.5 mg/cm$^2$/day. In some embodiments, the means for enhancing ketamine flux is oleyl oleate (about 5.7% by weight) and levulinic acid (about 5.2% by weight). In some embodiments, the DIA layer comprises the means for preventing crystallization of ketamine in the drug-in-adhesive layer after the transdermal delivery device is stored at 40° C. at a relative humidity of 75% for 3 months, 6 months, or longer. In some embodiments, the means for preventing crystallization of ketamine is Kollidon VA64 (about 21.7% by weight). In some embodiments, the pressure sensitive adhesive comprises a polyacrylate copolymer such as a polyacrylate-vinylacetate copolymer, e.g., Duro Tak 87-2677. In some embodiments, the pressure sensitive adhesive such as polyacrylate copolymer comprises a non-reactive polyacrylate copolymer, such as Duro Tak 87-900A. In some embodiments, the pressure sensitive adhesive can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

The DIA layer herein, such as those included in the transdermal delivery device herein (e.g., any of [1]-[18], [28], or [83] of the Brief Summary), is typically homogeneous or substantially homogeneous. For example, in some embodiments, the DIA layer is a homogeneous mixture. In some embodiments, the DIA layer herein is substantially free of ketamine particles or crystals, e.g., after a transdermal delivery device comprising the DIA layer is stored at room temperature (25±2° C.) at 60% relative humidity (RH)±5% RH for about 6 months or longer, e.g., about 6 months, about 12 months, about 18 months, about 24 months, about 30 months, or longer, or at 40±2° C. at 75% relative humidity (RH)±5% RH for about 1 month, about 3 months, about 6 months, or longer. In some embodiments, the DIA layer herein does not have any visible ketamine particle or crystal, for example, the DIA layer does not have any ketamine particles or crystals that are observable by visual inspection without magnification, e.g., after a transdermal delivery device comprising the DIA layer is stored at room temperature (25±2° C.) at 60% relative humidity (RH)±5% RH for about 6 months or longer, e.g., about 6 months, about 12 months, about 18 months, about 24 months, about 30 months, or longer, or at 40±2° C. at 75% relative humidity (RH)±5% RH for about 1 month, about 3 months, about 6 months, or longer.

In some embodiments, the DIA layer herein, such as those included in the transdermal delivery device herein (e.g., any of [1]-[18], [28], or [83] of the Brief Summary, or any of the monolithic patches herein), does not have any visible ketamine particles or crystals by polarized microscope after a transdermal delivery device comprising the DIA layer is stored at room temperature (25±2° C.) at 60% relative humidity (RH)±5% RH for about 1 month, about 3 months, about 6 months, about 12 months, about 18 months, about 24 months, about 30 months, or longer. In some embodiments, the DIA layer herein, such as those included in the transdermal delivery device herein (e.g., any of [1]-[18], [28], or [83] of the Brief Summary or any of the monolithic patches herein), does not have any visible ketamine particles or crystals by polarized microscope after a transdermal delivery device comprising the DIA layer is stored at 40±2° C. at 75% relative humidity (RH)±5% RH for about 1 month, about 3 months, about 6 months, or longer. In any of the embodiments described herein, unless specified or otherwise contrary, the DIA layer herein, such as those included in the transdermal delivery device herein (e.g., any of [1]-[18], [28], or [83] of the Brief Summary or any of the monolithic patches herein), does not have any visible ketamine particles or crystals by polarized microscope after a transdermal delivery device comprising the DIA layer is stored at room temperature at 60% relative humidity (RH)±5% RH for about 24 months or longer, or stored at 40±2° C. at 75% relative humidity (RH)±5% RH for about 6 months or longer.

One challenge in developing a DIA type transdermal delivery device is to maintain the active ingredient (drug) in the DIA layer without forming drug crystals. WO2017/003935 described an example of ketamine DIA patch, which was found to be free of drug crystals after being stored for 6 months. The described example therein contained Ketamine, 25 wt %, Duro Tak 47-4098, 40 wt %, polymethyacrylate as crystallization inhibitor, 20 wt %, and a combination of oleyl alcohol, levulinic acid, and diethylene glycol monoethyl ether as permeation enhancers, each 5 wt %). However, for reasons unknown to the applicant, when this example in WO2017/003935 publication was repeated, ketamine crystals were observed in less than 1 week after preparation. Further researches suggested that the combination of ingredients, not the identity of the crystallization inhibitor alone, is important in achieving the desired stability. For example, while the use of Duro Tak 87-900A with Soluplus in preparing ketamine DIA patches had resulted patches free of ketamine crystals for 6 months, the addition of oleyl oleate and levulinic acid to the DIA layer resulted patches having ketamine crystals formed within 3 months from preparation. The three formulations with Duro Tak 87-900A have the following ingredients by weight: (1) ketamine, 14%, Soluplus, 19%, and Duro Tak 87-900A, 68%, (no crystals after 6 months of preparation); (2) ketamine, 22%, Soluplus, 24%, and Duro Tak 87-900A, 54%, (no crystals after 6 months of preparation); (3) ketamine, 20%, Soluplus, 20%, oleyl oleate, 5%, levulinic acid, 5%, and Duro Tak 87-900A, 50%, (crystals within 3 months of preparation). WO2017/003935 also describes that an example of ketamine patch with a combination of Duro Tak 87-2677 and Kollidon VA64 did not achieve a physical stability for longer than 3 months. However, it was surprisingly found that the DIA patches herein with the same combination of Duro Tak 87-2677 and Kollidon VA64 achieved excellent storage stability for 30 months and beyond. The preliminary studies by the inventors herein show that Kollidon VA64 contributed to the stability of the formulation. For example, in an initial study, the formulation prepared with ketamine, 20%, Kollidon VA64, 20%, oleyl oleate, 5%, levulinic acid, 5%, and Duro Tak 87-2677, 50%, was found to have no crystals after 6 months of preparation. In contrast, in a formulation prepared with ketamine, 20%, oleyl oleate, 7%, levulinic acid, 7%, and Duro Tak 87-2677, 66%, i.e., Kollidon VA64 was not used, ketamine crystals formed within 3 months of preparation.

The transdermal delivery device herein (e.g., any of [1]-[18], [28], or [83] of the Brief Summary) is preferably storage stable when stored at room temperature (25±2° C.) at 60% relative humidity (RH)±5% RH or at 40±2° C. at 75% relative humidity (RH)±5% RH, for about 1 month, 3 months, 6 months, or longer. By storage stable, it is meant that the transdermal delivery device, after being stored under the storage condition for a designated period of time, would be accepted by those skilled in the art as equivalent to the initial transdermal delivery device, i.e., at the beginning of the storage. Storage stable is typically characterized by one or more of the following: (1) substantially the same amount of drug related impurities, no significant increased amount of either individual or total impurities; (2) substantially the same amount of ketamine; (3) substantially the same physical properties such as peel adhesion, shear adhesion, tack force, release force, etc.; and (4) substantially the same drug release rate and/or ketamine permeation rate. "Substantially the same" should be understood as meaning within 80-125% or within experimental errors.

In some embodiments, the transdermal delivery device herein (e.g., any of [1]-[18], [28], or [83] of the Brief Summary) is storage stable for about 1 month, about 3 months, about 6 months, or longer, such as for about 12 months, about 18 months, about 24 months, about 30 months, or longer, when stored at room temperature (25±2° C.) at 60% relative humidity (RH)±5% RH. In some embodiments, the transdermal delivery device herein (e.g., any of [1]-[18], [28], or [83] of the Brief Summary) is storage stable for about 1 month, about 3 months, about 6 months, or longer when stored at 40±2° C. at 75% relative humidity (RH)±5% RH. In some embodiments, the transdermal delivery device herein (e.g., any of [1]-[18], [28], or [83] of the Brief Summary) is characterized as conforming to the acceptance criteria described in Tables 1D or 1E in the Examples section, for about 6 months or more, such as for about 6 months, about 12 months, about 18 months, about 24 months, about 30 months, or more, when stored at room temperature (25±2° C.) at 60% relative humidity (RH)±5% RH or for about 1 month, about 3 months, or about 6 months, when stored at 40±2° C. at 75% relative humidity (RH)±5% RH. In any of the embodiments described herein, unless specified or otherwise contrary, the transdermal delivery device herein (e.g., any of [1]-[18], [28], or [83] of the Brief Summary) can be storage stable for about 24 months or longer, when stored at room temperature at 60% relative humidity±5% RH, or storage stable for about 6 months, or longer when stored at 40±2° C. at 75% relative humidity (RH)±5% RH.

Typically, the transdermal delivery device herein (e.g., any of [1]-[18], [28], or [83] of the Brief Summary) is supported by a backing layer such as an impermeable backing film, and the adhesive surface is protected by a release liner prior to use. Various materials can be used as a backing layer for the transdermal delivery device herein. Typically, the backing layer is impermeable. For example, the backing layer can be comprised of impermeable polymeric films such as polyester (PET) or polyethylene (PE) films. In some embodiments, the backing layer can comprise a polyester, such as Scotchpak 9723 (3M Drug Delivery Systems), Scotchpak 9736 or Scotchpak 1012, a polyurethane film, such as Scotchpak 9701, or a polyethylene film, such as CoTran 9720. In some embodiments, the backing is part of an overlay, and can be a non-woven fabric, a polyurethane film, or other pliable material to provide flexibility and better wear. In some embodiments, the backing layer can be a pigmented polyethylene and polyester laminated film, such as Scotchpak 9723 (3M Drug Delivery Systems). The backing layer can have a thickness of about 1-10 mils, such as about 1, 2, or 3 mils.

The release liner can be manufactured in the desired size for the transdermal delivery device herein (e.g., any of [1]-[18], [28], or [83] of the Brief Summary). The release liner can be comprised of silicone or fluoro-polymer coated polyester film. The release liner protects the transdermal delivery device during storage and is removed before its use. Silicone-coated release liners include those manufactured by Mylan Corporation, Loparex Corporation, and 3M's Drug Delivery Systems. The fluoro-polymer coated release liners include those manufactured and supplied by 3M's Drug Delivery Systems and Loparex. In some embodiments, the release liner comprises 3M's ScotchPak 9744 or Scotchpak 1022. In some embodiments, the release liner can be a fluoro-polymer coated release liner, such as those from Loparex.

The transdermal delivery device herein (e.g., any of [1]-[18], [28], or [83] of the Brief Summary) can also optionally include other suitable excipients such as humectants, plasticizers, antioxidants, anti-irritants, gel-forming agents, etc. These excipients are within the knowledge of those skilled in the art, and can be found, for example, in the Handbook of Pharmaceutical Excipients, ($7^{th}$ ed. 2012), the entire content of which is hereby incorporated by reference. In some embodiments, additional active ingredient(s) can also be included in the transdermal delivery device herein. However, in some embodiments, ketamine is the only active ingredient included in the transdermal delivery device herein (e.g., any of [1]-[18], [28], or [83] of the Brief Summary).

The transdermal delivery device herein (e.g., any of [1]-[18], [28], or [83] of the Brief Summary) can have different sizes (patch sizes) depending on its application. When applying the transdermal delivery devices herein to a skin of a subject, all of the adhesive surface can become in contact with the skin in theory. Thus, the area of the adhesive surface defines a skin contact area where the active ingredient from the device can permeate the skin, which is also herein referred to as an active surface area. In some embodiments, the adhesive surface is the only surface of the transdermal delivery device that is in contact with the skin upon application, and the active surface area is the same as the area of the adhesive surface. In a typical DIA patch, the patch size is the same as the area of the adhesive surface and the active surface area. Unless otherwise obvious from context, the unit "/$cm^2$" should be understood as per square centimeter of active surface area as defined herein.

The active surface area, ketamine flux per unit area, and duration of application (or patch-on period), together determine the doses of the drug to be delivered. Typically, the active surface area of the transdermal delivery device herein (e.g., any of [1]-[18], [28], or [83] of the Brief Summary) can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 70 $cm^2$, about 80 $cm^2$, about 90 $cm^2$, about 100 $cm^2$, about 120 $cm^2$, about 150 $cm^2$, about 200 $cm^2$ or any ranges between the specified values), for example, about 10 $cm^2$ to about 100 $cm^2$. In some embodiments, the active surface area of the transdermal delivery device herein (e.g., any of [1]-[18], [28], or [83] of the Brief Summary) can be about 10 $cm^2$ to about 180 $cm^2$, such as about 20 $cm^2$, about 30 $cm^2$, about 40 $cm^2$, about 50 $cm^2$, about 60 $cm^2$, about 70 $cm^2$, about 80 $cm^2$, about 90 $cm^2$, about 100 $cm^2$, about 120 $cm^2$, about 140 $cm^2$, about 160 $cm^2$, or about 180 $cm^2$.

In some embodiments, the transdermal delivery device herein (e.g., any of [1]-[18], [28], or [83] of the Brief Summary) can be configured to provide ketamine to a subject (e.g., human subject) at a ketamine flux of about 0.10 mg/$cm^2$/day to about 1 mg/$cm^2$/day. For example, in some embodiments, the transdermal delivery device can transdermally deliver about 0.1 mg/$cm^2$/day, about 0.2 mg/$cm^2$/day, about 0.3 mg/$cm^2$/day, about 0.4 mg/$cm^2$/day, about 0.5 mg/$cm^2$/day, or about 1 mg/$cm^2$/day, or any range between the recited values, such as about 0.1-0.5 mg/$cm^2$/day, about 0.2-0.5 mg/$cm^2$/day, etc.

The total ketamine loading for the transdermal delivery device herein (e.g., any of [1]-[18], [28], or [83] of the Brief Summary) can be adjusted based on the desired total dose. Typically, the total ketamine loading can be about 0.2 mg/$cm^2$ to about 2 mg/$cm^2$ (e.g., about 0.2 mg/$cm^2$, about 0.3 mg/$cm^2$, about 0.4 mg/$cm^2$, about 0.5 mg/$cm^2$, about 0.6 mg/$cm^2$, about 0.7 mg/$cm^2$, about 0.8 mg/$cm^2$, about 0.9 mg/$cm^2$, about 1 mg/$cm^2$, about 1.2 mg/$cm^2$, about 1.5 mg/$cm^2$, about 1.8 mg/$cm^2$, about 2 mg/$cm^2$, or any ranges between the recited values such as about 0.2-1 mg/$cm^2$, about 0.5-1 mg/$cm^2$, about 0.5-1.5 mg/$cm^2$, etc.). As used herein, the total ketamine load of a transdermal delivery device can be calculated by dividing the total amount of the ketamine in the transdermal delivery device by its active surface area.

The DIA layer herein is typically formulated such that transdermal delivery device herein can adhere to the skin of a subject for a desired period of time. For example, in some embodiments, the transdermal delivery device herein (e.g., any of [1]-[18], [28], or [83] of the Brief Summary) is capable of adhering continuously to the skin of a subject for a period of time ranging from about 8 hours to about 168 hours, such as for about 8 hours, about 12 hours, about 18 hours, about 24 hours, about 2 days, about 3 days, about 4 days, about 5 days, about 6 days, or about 7 days or more. In some embodiments, the transdermal delivery device herein (e.g., any of [1]-[18], [28], or [83] of the Brief Summary) is capable of continuously delivering ketamine to the subject during the period of time when the transdermal delivery device adheres to the skin of the subject, for example, at a substantially constant rate ranging from about 0.1 mg/$cm^2$/day to about 1 mg/$cm^2$/day (e.g., exemplified herein). In some embodiments, the transdermal delivery device herein (e.g., any of [1]-[18], [28], or [83] of the Brief Summary) can also be characterized as having substantially the same adhesive property (e.g., peel adhesion, shear adhesion, tack force, release force, etc.) after storage at room temperature (25±2° C.) at 60% relative humidity (RH)±5% RH for about 1 month, about 3 months, about 6 months, about 12 months, about 18 months, about 24 months, about 30 months, or longer, or at 40±2° C. at 75% relative humidity (RH)±5% RH for about 1 month, about 3 months, about 6 months, or longer. In some embodiments, the transdermal delivery device herein (e.g., any of [1]-[18], [28], or [83] of the Brief Summary) can also be characterized as having substantially the same ketamine permeation rate after storage at room temperature (25±2° C.) at 60% relative humidity (RH)±5% RH for about 1 month, about 3 months, about 6 months, about 12 months, about 18 months, about 24 months, about 30 months, or longer, or at 40±2° C. at 75% relative humidity (RH)±5% RH for about 1 month, about 3 months, about 6 months, or longer. In any of the embodiments described herein, unless specified or otherwise contrary, the transdermal delivery device herein (e.g., any of

[1]-[18], [28], or [83] of the Brief Summary) can be characterized as having substantially the same ketamine permeation rate after storage at room temperature (25±2° C.) at 60% relative humidity (RH)±5% RH for about 24 months or about 30 months or longer, or at 40±2° C. at 75% relative humidity (RH)±5% RH for about 6 months or longer.

Method of Preparation

The transdermal delivery device herein can be readily prepared by those skilled in the art in view of the present disclosure, e.g., as described below and in the Examples section.

In some embodiments, the present disclosure also provides a method of preparing an adhesive composition, such as a solvent casting method. The method typically comprises mixing ketamine and other ingredients, such as the permeation enhancer, crystallization inhibitor, pressure sensitive adhesive, and antioxidant described herein, to form a homogenous mixture, and drying the homogenous mixture.

For example, in some embodiments, the method of preparing the adhesive composition comprises:
(a) mixing ketamine, oleyl oleate, levulinic acid, a vinyl pyrrolidone polymer, a polyacrylate copolymer, and optionally an antioxidant in a solvent to form a homogenous mixture; and
(b) drying the homogenous mixture to remove the solvent, thereby providing the adhesive composition, wherein on a dry basis of the adhesive composition:
(i) ketamine is in an amount of about 14-17% by weight;
(ii) oleyl oleate and levulinic acid are each in an amount of about 4-7% by weight;
(iii) the vinyl pyrrolidone polymer is in an amount of about 15-25% by weight;
(iv) the polyacrylate copolymer is in an amount of about 45-55% by weight; and
(v) the optional antioxidant, if present, is in an amount of about 0.01-1% by weight.

In some embodiments, the solvent comprises ethyl acetate. In some embodiments, on a dry basis of the adhesive composition, the ketamine is in an amount of about 14%, about 15%, about 16%, or about 17% by weight of the DIA layer. In some embodiments, on a dry basis of the adhesive composition, each of the oleyl oleate and levulinic acid is independently present in an amount of about 4%, about 5%, about 6%, or about 7% by weight. In some embodiments, the vinyl pyrrolidone polymer is a polyvinyl pyrrolidone-co-vinyl acetate such as Kollidon VA-64. In some embodiments, the vinyl pyrrolidone polymer can be present in an amount of about 15%, about 16%, about 17%, about 18%, about 19%, about 20%, about 21%, about 22%, about 23%, about 24%, about 25%, or any range between the recited value such as about 20-25%, by weight, on a dry basis of the adhesive composition. In some embodiments, the polyacrylate copolymer is a polyacrylate-vinylacetate copolymer, such as Duro Tak 87-2677. In some embodiments, the polyacrylate copolymer is a non-reactive polyacrylate copolymer, such as Duro Tak 87-900A. In some embodiments, the polyacrylate copolymer can be in an amount of about 45%, about 50%, about 55%, or any range between the recited values by weight, on a dry basis of the adhesive composition. In some embodiments, the adhesive composition comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, etc. by weight, on a dry basis of the adhesive composition. In some embodiments, the adhesive composition is free of DMSO. Typically, the method includes casting the homogenous mixture onto an appropriate surface in a desired quantity before drying so that the dried adhesive composition can have a desired thickness, which is typically about 1-15 mils, such as about 2, 3, 4, 5, 10 mils, etc.

In some embodiments, the method of preparing the adhesive composition comprises:
(a) mixing ketamine, oleyl oleate, levulinic acid, a vinyl pyrrolidone polymer, a polyacrylate copolymer, and an antioxidant in a solvent to form a homogenous mixture; and
(b) drying the homogenous mixture to remove the solvent, thereby providing the adhesive composition, wherein on a dry basis of the adhesive composition:
(i) ketamine is in an amount of about 15-16%, e.g., about 15.7% by weight;
(ii) oleyl oleate and levulinic acid are each in an amount of about 5-6% by weight;
(iii) the vinyl pyrrolidone polymer (e.g., polyvinyl pyrrolidone-co-vinyl acetate) is in an amount of about 20-25% by weight;
(iv) the polyacrylate copolymer (e.g., polyacrylate-vinylacetate copolymer, preferably, a carboxylate-functionalized polyacrylate-vinylacetate copolymer) is in an amount of about 50-55% by weight; and
(v) the antioxidant is in an amount of about 0.3-0.7%, such as about 0.5% by weight.

In some embodiments, on a dry basis of the adhesive composition, each of the oleyl oleate and levulinic acid is independently present in an amount of about 5%, about 5.5%, or about 6% by weight. In some embodiments, the vinyl pyrrolidone polymer is a polyvinyl pyrrolidone-co-vinyl acetate, such as Kollidon VA-64, which can be present in an amount of about 20%, about 21%, about 22%, about 23%, about 24%, about 25%, or any range between the recited value such as about 20-22%, by weight, on a dry basis of the adhesive composition. In some embodiments, the polyacrylate copolymer can be a polyacrylate-vinylacetate copolymer, preferably, a carboxylate-functionalized polyacrylate-vinylacetate copolymer, such as Duro Tak 87-2677, which can be in an amount of about 50%, about 51%, about 52%, about 53%, about 54%, about 55%, or any range between the recited values by weight on a dry basis of the adhesive composition. In some embodiments, the antioxidant can be a phenol antioxidant, such as butylated hydroxytoluene. In some embodiments, the DIA layer is free of DMSO. Typically, the method includes casting the homogenous mixture onto an appropriate surface in a desired quantity before drying so that the dried adhesive composition can have a desired thickness, which is typically about 1-15 mils, such as about 2, 3, 4, 5, 10 mils, etc.

In some embodiments, the adhesive composition can be used to prepare a transdermal delivery device herein. For example, in some embodiments, the method comprises laminating the adhesive composition on a backing layer (e.g., described herein), protecting the adhesive surface with a release liner (e.g., described herein), and die-cutting the laminated adhesive composition into one or more transdermal patches having a patch size ranging from about 10 $cm^2$ to about 180 $cm^2$ (e.g., about 20 $cm^2$, about 30 $cm^2$, about 40 $cm^2$, about 50 $cm^2$, about 60 $cm^2$, about 70 $cm^2$, about 80 $cm^2$, about 90 $cm^2$, about 100 $cm^2$, about 120 $cm^2$, about 140 $cm^2$, about 160 $cm^2$, or about 180 $cm^2$). Typically, the one or more transdermal patches can individually have a total ketamine load of about 0.5 mg/cm$^2$ to about 2 mg/cm$^2$ (e.g., about 0.5 mg/cm$^2$, about 0.6 mg/cm$^2$, about 0.7 mg/cm$^2$, about 0.8 mg/cm$^2$, about 0.9 mg/cm$^2$, about 1 mg/cm$^2$, about 1.2 mg/cm$^2$, about 1.5 mg/cm$^2$, about 1.8 mg/cm$^2$, about 2 mg/cm$^2$, or any ranges between the recited values such as about 0.2-1 mg/cm$^2$, about 0.5-1 mg/cm$^2$, about 0.5-1.5 mg/cm$^2$, etc.).

It should be noted that the adhesive composition, the homogenous mixture, transdermal delivery device that are prepared by the methods described herein are also novel compositions of the present disclosure.

Monolithic Ketamine Patches

Certain embodiments of the present disclosure are directed to monolithic patches comprising ketamine. The monolithic patch typically includes a backing layer (e.g., described herein), a drug-in-adhesive layer (e.g., described herein, such as described in [1]-[18] or [28] of the Brief Summary), and a release liner (e.g., described herein). In some embodiments, the monolithic patch can have an active surface area of about 10 cm$^2$ to about 180 cm$^2$, such as about 20 cm$^2$, about 30 cm$^2$, about 40 cm$^2$, about 50 cm$^2$, about 60 cm$^2$, about 70 cm$^2$, about 80 cm$^2$, about 90 cm$^2$, about 100 cm$^2$, about 120 cm$^2$, or about 180 cm$^2$. In some embodiments, the monolithic patch includes about 15 mg to about 300 mg of ketamine, such as about 24.7 mg, about 49.6 mg, about 87.3 mg, about 100 mg, about 112.5 mg, about 124.7 mg, about 150 mg, or about 225 mg of ketamine, or any ranges between the recited values. The monolithic patch is typically configured to deliver a dose of ketamine at a rate of about 4 mg/day to about 110 mg/day, which can for example last for 1 day, 2 days, or 3 days. For example, in some embodiments, the monolithic patch can deliver a dose at a rate of about 24 mg/day, which can be applied for a duration of 1 day to deliver about 24 mg of ketamine, a duration of 2 days to deliver about 48 mg of ketamine, or a duration of 3 days to deliver about 72 mg of ketamine. Typically, the monolithic patch herein is applied for a duration of about 24 hours. Suitable other ingredients and characteristics include any of those described herein in any combination.

For example, in some embodiments, the monolithic patch has an active surface area of about 20 cm$^2$ to about 180 cm$^2$, such as an active surface area of about 20 cm$^2$ and about 24.7 mg of ketamine, an active surface area of about 40 cm$^2$ and about 49.6 mg of ketamine, an active surface area of about 60 cm$^2$ and about 87.3 mg of ketamine, an active surface area of about 80 cm$^2$ and about 100 mg of ketamine, an active surface area of about 90 cm$^2$ and about 112.5 mg of ketamine, an active surface area of about 100 cm$^2$ and about 124.7 mg of ketamine, an active surface area of about 120 cm$^2$ and about 150 mg of ketamine, or an active surface area of about 180 cm$^2$ and about 225 mg of ketamine, wherein the monolithic patch includes a) a backing layer (e.g., described herein); b) a drug-in-adhesive layer, which comprises i) ketamine in an amount of about 14-17% by weight; ii) oleyl oleate and levulinic acid, each in an amount of about 4-7% by weight; iii) a polyvinyl pyrrolidone-co-vinyl acetate in an amount of about 15-25% by weight; iv) a polyacrylate adhesive, such as a carboxylate-functionalized polyacrylate-vinylacetate copolymer in an amount of about 45-55% by weight; and v) an antioxidant in an amount of about 0.01-1% by weight; and c) a release liner (e.g., described herein). In some embodiments, the ketamine is in an amount of about 14%, about 15%, about 16%, or about 17% by weight of the DIA layer. In some embodiments, each of the oleyl oleate and levulinic acid is independently present in an amount of about 4%, about 5%, about 6%, or about 7% by weight of the DIA layer. In some embodiments, the polyvinyl pyrrolidone-co-vinyl acetate, such as Kollidon VA-64, can be present in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the polyacrylate adhesive is a carboxylate-functionalized polyacrylate-vinylacetate copolymer, such as Duro Tak 87-2677, which can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some more specific embodiments, the monolithic patch has an active surface area of about 20 cm$^2$ to about 180 cm$^2$, such as an active surface area of about 20 cm$^2$ and about 24.7 mg of ketamine, an active surface area of about 40 cm$^2$ and about 49.6 mg of ketamine, an active surface area of about 60 cm$^2$ and about 87.3 mg of ketamine, an active surface area of about 80 cm$^2$ and about 100 mg of ketamine, an active surface area of about 90 cm$^2$ and about 112.5 mg of ketamine, an active surface area of about 100 cm$^2$ and about 124.7 mg of ketamine, an active surface area of about 120 cm$^2$ and about 150 mg of ketamine, or an active surface area of about 180 cm$^2$ and about 225 mg of ketamine, wherein the monolithic patch includes a) a backing layer (e.g., described herein); b) a drug-in-adhesive layer, which comprises i) ketamine in an amount of about 15-16%, such as about 15.7% by weight; ii) oleyl oleate and levulinic acid, each in an amount of about 5-6% by weight; iii) a polyvinyl pyrrolidone-co-vinyl acetate in an amount of about 20-25% by weight; iv) a carboxylate-functionalized polyacrylate-vinylacetate copolymer in an amount of about 50-55% by weight; and v) an antioxidant in an amount of about 0.3-0.7%, such as about 0.5% by weight; and c) a release liner (e.g., described herein). In some embodiments, each of the oleyl oleate and levulinic acid is independently present in an amount of about 5%, about 5.5%, or about 6% by weight of the DIA layer. In some embodiments, the polyvinyl pyrrolidone-co-vinyl acetate, such as Kollidon VA-64, can be present in an amount of about 20%, about 21%, about 22%, about 23%, about 24%, about 25%, or any range between the recited value such as about 20-22%, by weight of the DIA layer. In some embodiments, the carboxylate-functionalized polyacrylate-vinylacetate copolymer, such as Duro Tak 87-2677, can be in an amount of about 50%, about 51%, about 52%, about 53%, about 54%, about 55%, or any range between the recited values by weight of the DIA layer. In some embodiments, the antioxidant can be a phenol antioxidant, such as butylated hydroxytoluene. In some embodiments, the DIA layer is free of DMSO.

In some more specific embodiments, the monolithic patch has an active surface area of about 20 cm$^2$ to about 180 cm$^2$, such as an active surface area of about 20 cm$^2$ and about 24.7 mg of ketamine, an active surface area of about 40 cm$^2$ and about 49.6 mg of ketamine, an active surface area of about 60 cm$^2$ and about 87.3 mg of ketamine, an active surface area of about 80 cm$^2$ and about 100 mg of ketamine, an active surface area of about 90 cm² and about 112.5 mg of ketamine, an active surface area of about 100 cm² and about 124.7 mg of ketamine, an active surface area of about 120 cm² and about 150 mg of ketamine, or an active surface area of about 180 cm² and about 225 mg of ketamine, wherein the monolithic patch includes a) a backing layer (e.g., Scotchpak 9723); b) a drug-in-adhesive layer, with ingredients shown in Table A of Example 1A or prepared by the method according to Example 1A; and c) a release liner (e.g., Loparex).

In some embodiments, the monolithic patch has an active surface area of about 20 cm² and about 24.7 mg of ketamine, e.g., as described herein, which is configured to have a ketamine delivery rate of about 6-16 mg/day. In some more specific embodiments, the monolithic patch has an active surface area of about 40 cm² and about 49.6 mg of ketamine, e.g., as described herein, which is configured to have a ketamine delivery rate of about 10-30 mg/day. In some more specific embodiments, the monolithic patch has an active surface area of about 60 cm² and about 87.3 mg of ketamine, e.g., as described herein, which is configured to have a ketamine delivery rate of about 20-40 mg/day. In some more specific embodiments, the monolithic patch has an active surface area of about 80 cm² and about 100 mg of ketamine, e.g., as described herein, which is configured to have a ketamine delivery rate of about 25-50 mg/day. In some more specific embodiments, the monolithic patch has an active surface area of about 90 cm² and about 112.5 mg of ketamine, e.g., as described herein, which is configured to have a ketamine delivery rate of about 30-60 mg/day. In some more specific embodiments, the monolithic patch has an active surface area of about 100 cm² and about 124.7 mg of ketamine, e.g., as described herein, which is configured to have a ketamine delivery rate of about 35-70 mg/day. In some more specific embodiments, the monolithic patch has an active surface area of about 120 cm² and about 150 mg of ketamine, e.g., as described herein, which is configured to have a ketamine delivery rate of about 40-80 mg/day. In some more specific embodiments, the monolithic patch has an active surface area of about 180 cm² and about 225 mg of ketamine, e.g., as described herein, which is configured to have a ketamine delivery rate of about 60-110 mg/day.

In some embodiments, the monolithic patch is capable of adhering continuously to the skin of a subject for a period of time ranging from about 8 hours to about 168 hours, such as for about 8 hours, about 12 hours, about 18 hours, about 24 hours, about 2 days, about 3 days, about 4 days, about 5 days, about 6 days, or about 7 days or more. In some embodiments, the monolithic patch is capable of continuously delivering ketamine to the subject during the period of time when the transdermal delivery device adheres to the skin of the subject, for example, at a substantially constant rate to deliver a dose of ketamine for 1 day or up to three days.

The transdermal delivery device (e.g., monolithic patch herein) is typically packaged in unit dose pouches, typically from multilayered polyester, polyethylene, aluminum foil laminated pouch.

Methods of Administering Ketamine

Certain embodiments of the present disclosure are directed to methods of administering ketamine and/or hydroxynorketamine to a subject (e.g., a human subject) in need thereof. In some embodiments, the method is for antagonizing NMDA receptors in the subject. In some embodiments, the method is for enhancing synaptic plasticity in the subject. In some embodiments, the method is for enhancing expression of AMPA receptors in the subject. In some embodiments, the method is for antagonizing NMDA receptors and enhancing expression of AMPA receptors in the subject. In some embodiments, the method is for treating a disease or disorder in the subject, where antagonizing NMDA receptor, enhancing synaptic plasticity, and/or enhancing expression of AMPA receptor is beneficial. In some embodiments, the method is for treating depression, anxiety, and/or pain in the subject. In some embodiments, the subject is characterized as having depression (e.g., a major depressive disorder). In some embodiments, the subject is characterized as having pain (e.g., neuropathic pain). In some embodiments, the disease or disorder is one or more chosen from pain (e.g., neuropathic pain, complex regional pain syndrome (CRPS), chronic pain), depression (major depressive disorder, treatment-resistant depression, bipolar depression), restless legs syndrome, a condition associated with spinal cord injury (e.g., autonomic dysreflexia, immune suppression, chronic central neuropathic pain suffering from spinal cord injury, leukocyte apoptosis, splenic atrophy, leucopenia, or combinations thereof), anxiety, bipolar disorder (e.g., childhood-onset bipolar disorder, bipolar depression), stress-induced disorder (e.g., stress-induced affective disorder, stress-induced psychopathology), post-traumatic stress disorder, Alzheimer's dementia, amyotrophic lateral sclerosis, and suicidality. In some embodiments, the subject is characterized as having pain, e.g., neuropathic pain, complex regional pain syndrome (CRPS), or chronic pain. In some embodiments, the subject is characterized as having depression, such as major depressive disorder, treatment-resistant depression, or bipolar depression. In some embodiments, the subject is characterized as having psychosis, e.g., psychosis associated with Parkinson's disease, Alzheimer's disease, various dementia such as vascular dementia etc.

Ketamine has also been in clinical trials for various conditions. A simple search in clinicaltrial.gov identified that 48 clinical trials with the following conditions are associated with ketamine in phase 2 clinical trials or later in the U.S. since Jan. 1, 2019, (collectively "Ketamine Clinical Conditions"), which include: Mental Disorders; Psychotic Disorders; Pain; Depression; Depressive Disorder; Mood Disorders; Neurologic Manifestations; Behavioral Symptoms; Acute Pain; Emergencies; Self-Injurious Behavior; Suicide; Depressive Disorder, Major; Chemically-Induced Disorders; Disease Attributes; Substance-Related Disorders; Wounds and Injuries; Depression, Postpartum; Fractures, Bone; Genetic Diseases, Inborn; Pain, Postoperative; Pregnancy Complications; Puerperal Disorders; Suicidal Ideation; Syndrome; Anemia; Anemia, Hemolytic; Anemia, Hemolytic, Congenital; Anemia, Sickle Cell; Chronic Pain; Communicable Diseases; Depressive Disorder, Treatment-Resistant; Hematologic Diseases; Hemoglobinopathies; Hemolysis; Infection; Lung Diseases; Musculoskeletal Diseases; Opioid-Related Disorders; Postoperative Complications; Respiration Disorders; Respiratory Tract Diseases; Respiratory Tract Infections; Vascular Diseases; ADNP Syndrome; Acute Lung Injury; Acute Respiratory Distress Syndrome; Alcohol Drinking; Alcohol-Related Disorders; Alcoholism; Bipolar Disorder; Bipolar and Related Disorders; Brain Diseases; Bronchial Diseases; Bronchial Spasm; Central Nervous System Diseases; Cerebrovascular Disorders; Chromosome Aberrations; Chromosome Disorders; Coronaviridae Infections; Coronavirus Infections; Digestive System Diseases; Ear Diseases; Fatigue; Femoral Fractures; Fractures, Closed; Gastrointestinal Diseases; Genetic Diseases, X-Linked; Head and Neck Neoplasms; Hearing Disorders; Hemorrhoids; Heredodegenerative Disorders, Nervous System; Hypertrophy; Infant, Newborn, Diseases;

Infant, Premature, Diseases; Intellectual Disability; Intestinal Diseases; Ischemia; Labor Pain; Lung Injury; Mental Retardation, X-Linked; Muscle Cramp; Muscular Diseases; Musculoskeletal Pain; Neurobehavioral Manifestations; Nidovirales Infections; Otorhinolaryngologic Diseases; Pathological Conditions, Anatomical; Pneumonia; Pneumonia, Aspiration; Premature Birth; Pulmonary Atelectasis; Pulmonary Valve Insufficiency; RNA Virus Infections; Rectal Diseases; Respiratory Aspiration; Respiratory Distress Syndrome, Adult; Respiratory Distress Syndrome, Infant; Respiratory Distress Syndrome, Newborn; Respiratory Insufficiency; Rett Syndrome; Sensation Disorders; Severe Acute Respiratory Syndrome; Sickle Cell Anemia; Spasm; Stress Disorders, Post-Traumatic; Stress Disorders, Traumatic; Stroke; Suicide, Attempted; Tinnitus; Tobacco Use Disorder; Trauma and Stressor Related Disorders; Virus Diseases. In some embodiments, the method described herein can also be for treating a disease or disorder selected from the Ketamine Clinical Conditions. In some embodiments, the method comprises transdermally delivering a therapeutically effective amount of ketamine to a subject in need thereof.

In some embodiments, the method herein comprises applying a transdermal delivery device described herein (such as those described in [1]-[18], [23], or [83] of the Brief Summary, or any of the monolithic patches described herein), to the skin of the subject. In any of the embodiments described herein, the method can deliver to the subject about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine, for example, continuously for a period of time selected from about 8 hours, about 12 hours, about 18 hours, about 24 hours, about 2 days, about 3 days, about 4 days, about 5 days, about 6 days, and about 7 days. In some embodiments, applying the transdermal delivery device provides a therapeutically effective concentration of ketamine and/or hydroxynorketamine for an extended period. In some embodiments, applying the transdermal delivery device provides a lower ketamine $C_{max}$ compared to that of a dose-equivalent intravenous or intranasal formulation.

Typically, for any of the methods described hereinabove, the transdermal delivery device is applied to provide a therapeutically effective concentration of ketamine and/or hydroxynorketamine in the plasma of the subject for a desired period of time. For example, in some embodiments, the subject is characterized as having a depression (e.g., a major depressive disorder), and the therapeutically effective concentration of ketamine and/or hydroxynorketamine can be controlled to achieve an antidepressant effect (e.g., the treatment of MDD). For example, in some embodiments, the plasma concentration of ketamine in the subject having depression can be controlled to range from about 5 ng/ml to about 50 ng/ml, such as from about 10 ng/ml to about 30 ng/ml. In some embodiments, the plasma concentration of hydroxynorketamine in the subject having depression can be controlled to range from about 5 ng/ml to about 50 ng/ml, such as from about 10 ng/ml to about 30 ng/ml. In some embodiments, the subject is characterized as having a pain (e.g., a neuropathic pain, CRPS, or chronic pain), and the therapeutically effective concentration of ketamine and/or hydroxynorketamine can be controlled to achieve an analgesic effect (e.g., the treatment of neuropathic pain, CRPS, or chronic pain). For example, in some embodiments, the plasma concentration of ketamine in the subject having pain can be controlled to range from about 5 ng/ml to about 50 ng/ml, such as from about 10 ng/ml to about 30 ng/ml. In some embodiments, the plasma concentration of hydroxynorketamine in the subject having pain can be controlled to range from about 5 ng/ml to about 50 ng/ml, such as from about 10 ng/ml to about 30 ng/ml.

Methods of Treating Depression

Some embodiments of the present disclosure are directed to methods of treating depression. In some embodiments, the method comprises transdermally administering to a subject in need thereof a therapeutically effective amount of ketamine. Typically, the therapeutically effective amount of ketamine is delivered to the subject by administering a transdermal delivery device (e.g., described herein, such as those described in [1]-[18], [23], or [83] of the Brief Summary, or any of the monolithic patches described herein) to the subject. In some embodiments, the therapeutically effective amount of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours. In some embodiments, the therapeutically effective amount of ketamine is a dose of about 15 mg to about 30 mg of ketamine. In some embodiments, the therapeutically effective amount of ketamine is a dose of about 30 mg to about 60 mg (e.g., about 50 mg) of ketamine. In some embodiments, the therapeutically effective amount of ketamine is a dose of about 60 mg to about 120 mg (e.g., about 100 mg) of ketamine. In some embodiments, the therapeutically effective amount of ketamine is a dose of about 75 mg to about 150 mg of ketamine. Typically, for the methods herein, the dose of ketamine is about 15 mg to about 150 mg and is delivered to the subject over about 24 hours (or 15-150 mg/24 hours), for example, by administration or application of the transdermal delivery device comprising ketamine herein to the subject for a duration of about 24 hours. In some embodiments, the dose of ketamine can be about 40 mg to about 250 mg, which can be delivered over about 1-3 days. In some embodiments, the dose of ketamine can be about 15 mg to about 60 mg, which can be delivered over about 8 hours to 16 hours.

The ketamine dose can be administered at a frequency ranging from once a day to once a week, preferably, 1-3 times every week, more preferably, once in at least 3 days, such as once a week or twice a week. As discussed herein, it was found that administering one single dose of about 15 mg to about 150 mg of ketamine over about 24 hours can have a sustained effect in treating depression for about 2 or 3 days or more, such as a week. Thus, while not precluded, the therapeutically effective amount of ketamine does not need to be administered to a subject in need daily. In other words, the administering of ketamine can have a gap between two consecutive doses. For example, in some embodiments, a first dose of about 15 mg to about 150 mg (e.g., about 15 mg, about 30 mg, about 50 mg, about 60 mg, about 75 mg, about 90 mg, about 100 mg, about 120 mg, about 150 mg, or any ranges between the recited values such as about 15-30 mg, about 30-60 mg, about 60-120 mg, about 75-150 mg, etc.) of ketamine can be transdermally administered to the subject over about 24 hours, which is followed by a gap period of 1-6 days with no ketamine transdermally delivered to the subject, and then a second dose of about 15 mg to about 150 mg (e.g., about 15 mg, about 30 mg, about 50 mg, about 60 mg, about 75 mg, about 90 mg, about 100 mg, about 120 mg, about 150 mg, or any ranges between the recited values such as about 15-30 mg, about 30-60 mg, about 60-120 mg, about 75-150 mg, etc.) of ketamine can be administered to the subject over about 24 hours, which cycle can be repeated during the treatment period. The first and second doses can be the same or different. Thus, as used herein, when it is said that the dosing frequency is once or twice a week, it should be understood that the transdermal delivery device comprising ketamine does not need to be applied to the subject continuously and be replaced right around the time the next dose is applied. Other similar expressions should also be understood similarly. In some preferred embodiments, each dose of ketamine is delivered over about 24 hours, and if the dosing frequency is once in a week or at least 3 days, there would be gaps between two consecutive doses. However, in some embodiments, the present disclosure also include dosing regimens with no gaps between two consecutive doses. In some embodiments, during the gap period, no transdermal delivery device is applied to the subject. In some embodiments, during the gap period, a substantially the same placebo transdermal delivery device (except without ketamine) can be applied to the subject. For example, in some embodiments, the transdermal delivery device comprising ketamine is applied for a duration of about 24 hours, which can be replaced with the substantially the same placebo transdermal delivery device, and after being applied for a duration of about 24 hours, it can be replaced with a new transdermal delivery device comprising ketamine or placebo transdermal delivery device, depending on the dosing frequency of ketamine. In some embodiments, the use of placebo transdermal delivery device can improve patient compliance, which can also enhance the conditional effect as discussed herein.

The transdermal delivery device herein is typically applied to the subject for a duration of about 24 hours (i.e., the patch-on period is 24 hours), although a longer duration such as two days or shorter duration such as about 8-16 hours can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. One or more monolithic patches can be applied to the subject to achieve each dose of the therapeutically effective amount of ketamine.

The depression suitable to be treated by the methods herein are not particularly limited. Such depression includes but is not limited to any of: major depressive disorder, single episode, recurrent major depressive disorder, unipolar depression, seasonal affective disorder-winter depression, bipolar mood disorder-bipolar depression, mood disorder due to a general medical condition with major depressive like episode, or mood disorder due to a general medical condition with depressive features, disruptive mood dysregulation disorder (classified by significant childhood irritability and tantrums), premenstrual dysphoric disorder (PMDD), causing periods of anxiety, depression, or irritability in the week or two before a woman's menstruation, persistent depressive disorder, and postpartum depression (PPD).

There are three types of depression generally characterized in the art, major depression, dysthymic disorder, or dysthymia, and depressive disorder not otherwise specified. Major depression is characterized by peak episodes of extreme depression. During a peak episode, the patient may suffer from depressed mood, and markedly diminished interest or pleasure in activities. Other symptoms include significant weight loss or weight gain, decrease or increase in appetite, insomnia or hypersomnia, psychomotor agitation or retardation, fatigue or loss of energy, feelings of worthlessness or excessive or inappropriate guilt, diminished ability to think or concentrate or indecisiveness, recurrent thoughts of death, suicidal ideation or suicidal attempts. Symptoms last for at least two weeks and cause significant distress or impairment in important areas of functioning.

Dysthymia is characterized by depressed mood for at least 2 years as well as other symptoms like poor appetite or overeating, insomnia or hypersomnia, low energy or fatigue, low self-esteem, poor concentration or difficulty making decisions and feelings of hopelessness. As is recognized in the field of psychiatric arts, depression may also comprise, and/or may also manifest itself in a variety of forms, including but not limited to, seasonal affective disorder, diurnal mood variations, or depression associated with menopause. Diagnostic criteria for dysthymia and major depression, as well as for seasonal affective disorder, diurnal mood variations and depression associated with menopause, are more fully explained in the Diagnostic and Statistical Manual of Mental Disorders, Fifth Edition, (DSM 5) published by the American Psychiatric Association or by the ICD (ICD-10: International Statistical Classification of Diseases and Related Health Problems (10th Revision) or any other psychiatric classification system. The presence and the severity of the depressive state can also be determined with structured and semi-structured interview and questioners such as the Hamilton score that is well known in the art.

In some embodiments, the present disclosure provides a method of treating a subject who has a major depressive disorder (MDD), the method comprising transdermally administering to the subject in need thereof a therapeutically effective amount of ketamine. In some embodiments, the method comprises administering to the subject a transdermal delivery device comprising ketamine (e.g., described herein, such as those described in [1]-[18], [23], or [83] of the Brief Summary, or any of the monolithic patches described herein) to deliver the therapeutically effective amount of ketamine. The dosing amount and dosing regimen include any of those described herein in any combination, e.g., those described in [30]-[39] of the Brief Summary. For example, in some preferred embodiments, the method comprises administering the transdermal delivery device to the subject 1-3 times every week, more preferably, once in at least 3 days, such as once a week or twice a week. Each dose to be administered is typically in the range of about 15 mg to about 150 mg (e.g., exemplified herein) of ketamine. In some embodiments, there is a gap period between two consecutive doses of ketamine. In some embodiments, one or more placebo transdermal delivery devices can be applied to the subject during the gap period as described herein. In some embodiments, there is no gap period between two consecutive doses of ketamine. For each application, the transdermal delivery device is typically applied to the subject for a duration of about 24 hours (i.e., the patch-on period is about 24 hours) to deliver the desired dose of ketamine, although a longer duration such as two days or shorter duration such as about 8-16 hours can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The subject with MDD should be understood as meeting the Diagnostic and Statistical Manual of Mental Disorders, Fifth Edition (DSM-5) criteria for MDD based on the Structured Clinical Interview for DSM-5 (SCID-5). In some embodiments, the subject is characterized as having a Montgomery-Asberg Depression Rating Scale (MADRS) ≥20. The MADRS questionnaire includes questions on the following symptoms 1. Apparent sadness 2. Reported sadness 3. Inner tension 4. Reduced sleep 5. Reduced appetite 6. Concentration difficulties 7. Lassitude 8. Inability to feel 9. Pessimistic thoughts 10. Suicidal thoughts, with each item yields a score of 0-6, with a total score of 60. Typically, a MADRS score of 20-34 is considered having moderate depression and greater than 34 indicates severe depression. In some embodiments, the subject is characterized as having failed at least one antidepressant treatment based on the Massachusetts General Hospital Antidepressant Treatment Response Questionnaire (MGH ATRQ) (Gregory M. Chandler, Dan V. Iosifescu, Mark H. Pollack, Steven D. Targum & Maurizio Fava. Validation of the Massachusetts General Hospital Antidepressant Treatment History Questionnaire (ATRQ). CNS Neuroscience & Therapeutics 16 (2010) 322-325). In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has a single episode major depressive disorder. In some embodiments, the subject has recurrent major depressive disorder. In some embodiments, the subject has chronic major depressive disorder. In some embodiments, the subject is characterized as having treatment resistant depression, which refers to subjects meeting DSM-5 criteria for MDD and in the current depressive episode, and has not responded adequately to at least two different antidepressants of adequate dose and duration. See e.g., Spravato Prescribing Information, 2019. Typically, the method further comprises administering to the subject one or more additional antidepressant treatments, such as oral antidepressants or another ketamine related antidepressant such as intranasal ketamine treatment.

In some embodiments, the present disclosure also provides a method of treating a subject with recurrent or chronic depression, such as recurrent or chronic major depressive disorder, the method comprising transdermally administering to the subject in need thereof a therapeutically effective amount of ketamine. In some embodiments, the method comprises administering to the subject a transdermal delivery device comprising ketamine (e.g., described herein, such as those described in [1]-[18], [23], or [83] of the Brief Summary, or any of the monolithic patches described herein) to deliver the therapeutically effective amount of ketamine. The dosing amount and dosing regimen include any of those described herein in any combination, e.g., those described in [30]-[39] of the Brief Summary. For example, in some preferred embodiments, the method comprises administering the transdermal delivery device to the subject 1-3 times every week, more preferably, once in at least 3 days, such as once a week or twice a week. Each dose to be administered is typically in the range of about 15 mg to about 150 mg (e.g., exemplified herein) of ketamine. In some embodiments, there is a gap period between two consecutive doses of ketamine. In some embodiments, one or more placebo transdermal delivery devices can be applied to the subject during the gap period as described herein. In some embodiments, there is no gap period between two consecutive doses of ketamine. For each application, the transdermal delivery device is typically applied to the subject for a duration of about 24 hours (i.e., the patch-on period is about 24 hours) to deliver the desired dose of ketamine, although a longer duration such as two days or shorter duration such as about 8-16 hours can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. In some embodiments, the subject has a current depressive episode. In some embodiments, the subject does not have a current depressive episode or is in remission. In some embodiments, the therapeutically effective amount of ketamine is transdermally administered to the subject to delay a recurring depressive episode. In some embodiments, the therapeutically effective amount of ketamine is transdermally administered to the subject to alleviate one or more symptoms associated with the major depressive disorder. In some embodiments, the subject is characterized as having sub-optimal response to at least one antidepressant treatment. In some embodiments, the subject is characterized as having treatment resistant depression. Typically, the method further comprises administering to the subject one or more additional antidepressant treatments, such as oral antidepressants or another ketamine related antidepressant such as intranasal ketamine treatment.

In some embodiments, the present disclosure also provides a method of delivering a maintenance dose of ketamine to a subject in need. For example, in some embodiments, the present disclosure provides a method of treating depression in a subject in need thereof, which comprises administering to the subject a transdermal delivery device comprising ketamine to deliver a maintenance dose of ketamine to the subject. In some embodiments, the subject has received a bolus dose of ketamine. The bolus dose of ketamine is not particularly limited, which can be for example, an intravenous dose or an intranasal dose. In some embodiments, the method comprises administering to the subject a transdermal delivery device comprising ketamine (e.g., described herein, such as those described in [1]-[18], [23], or [83] of the Brief Summary, or any of the monolithic patches described herein) to deliver the maintenance dose of ketamine to the subject. In some embodiments, the maintenance dose of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours. In some embodiments, the maintenance dose of ketamine is a dose of about 15 mg to about 30 mg of ketamine. In some embodiments, the maintenance dose of ketamine is a dose of about 30 mg to about 60 mg of ketamine. In some embodiments, the maintenance dose of ketamine is a dose of about 60 mg to about 120 mg of ketamine. In some embodiments, the maintenance dose of ketamine is a dose of about 75 mg to about 150 mg of ketamine. As discussed herein, it was found that administering one single dose of about 15 mg to about 150 mg of ketamine over about 24 hours can have a sustained effect in treating depression for about 2 or 3 days or more such as a week. Without wishing to be bound by theories, it is believed that this prolonged antidepressant effect relates to the prolonged PK exposure of ketamine, norketamine, and hydroxynorketamine achieved by the transdermal delivery device herein. Thus, the transdermal delivery device can be suited for dosing regimen with a dosing frequency ranging from once a day to once every week, which is believed to be advantageous for use as a maintenance dose for treating depression. While not preferred, the maintenance dose of ketamine can also in some embodiment administered to a subject in need daily. In some preferred embodiments, the method comprises administering the transdermal delivery device to the subject 1-3 times every week, more preferably, once in at least 3 days, such as once a week or twice a week. In some embodiments, the administering can have a gap between two consecutive maintenance doses. For example, in some embodiments, a first maintenance dose of about 15 mg to about 150 mg (e.g., about 15 mg, about 30 mg, about 50 mg, about 60 mg, about 75 mg, about 90 mg, about 100 mg, about 120 mg, about 150 mg, or any ranges between the recited values such as about 15-30 mg, about 30-60 mg, about 60-120 mg, about 75-150 mg, etc.) of ketamine can be administered to the subject over about 24 hours, which is followed by a gap period of 1-6 days with no ketamine transdermally delivered to the subject, and then a second maintenance dose of about 15 mg to about 150 mg (e.g., about 15 mg, about 30 mg, about 50 mg, about 60 mg, about 75 mg, about 90 mg, about 100 mg, about 120 mg, about 150 mg, or any ranges between the recited values such as about 15-30 mg, about 30-60 mg, about 60-120 mg, about 75-150 mg, etc.) of ketamine can then be administered to the subject over about 24 hours, which cycle can be repeated during the treatment period. The first and second maintenance doses can be the same or different. In some embodiments, the administering does not have a gap between two consecutive maintenance doses. In some embodiments, during the gap period, a substantially the same placebo transdermal delivery device (except without ketamine) can be applied to the subject. For example, in some embodiments, the transdermal delivery device comprising ketamine is applied for a duration of about 24 hours to deliver the maintenance dose, which can be replaced with the substantially the same placebo transdermal delivery device, and after being applied for a duration of about 24 hours, it can be replaced with a new transdermal delivery device comprising ketamine or placebo transdermal delivery device, depending on the dosing frequency.

For each application, the transdermal delivery device is typically applied to the subject for a duration of about 24 hours (i.e., the patch-on period is about 24 hours) to deliver the desired dose of ketamine, although a longer duration such as two days or shorter duration such as about 8-16 hours can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The subject needing the maintenance dose is not particularly limited and includes any of those described herein having a depression, typically recurrent or chronic depression. For example, in some embodiments, the subject is characterized as having a MDD. In some embodiments, the subject is characterized as having a MADRS≥20. In some embodiments, the subject is characterized as having failed at least one antidepressant treatment based on the MGH ATRQ. In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has recurrent major depressive disorder. In some embodiments, the subject has chronic major depressive disorder. In some embodiments, the subject is characterized as having sub-optimal response to at least one antidepressant treatment. In some embodiments, the subject is characterized as having treatment resistant depression. In some embodiments, the subject is in remission, for example, from the bolus ketamine treatment and/or additional antidepressant treatments. In some embodiments, the method further comprises administering to the subject one or more additional antidepressant treatments during the maintenance treatment period, such as oral antidepressants or another ketamine related antidepressant such as intranasal ketamine treatment.

In any of the embodiments described herein, the method of treating depression can also be characterized in that the treated subject has no or minimal adverse effects associated with ketamine, including no or minimal dizziness, sedation, dissociative effects, blood pressure elevations. In other words, the method does not cause the subject to suffer from such adverse effects associated with ketamine. Typically, the method is also characterized in that the method is carried out without a risk evaluation and mitigation strategy (REMS) program, e.g., it is not necessary to ensure that the ketamine patch herein is only dispensed and administered to patients in a medically supervised healthcare setting that monitors these patients; it is not necessary to ensure pharmacies and healthcare settings that dispense the ketamine patch herein are certified; it is not necessary to ensure that each patient is informed about the serious adverse outcomes resulting from sedation and dissociation and need for monitoring; it is not necessary to ensure enrollment of all patients in a registry to further characterize the risks and support safe use. In some embodiments, the method herein does not require close monitoring of the subject in a medically supervised healthcare setting.

PK/PD of Ketamine Patches

Some embodiments of the present disclosure are based at least in part on the novel pharmacokinetic (PK) profile achieved herein as well as the associated pharmacodynamics (PD) effect.

Figure 5:
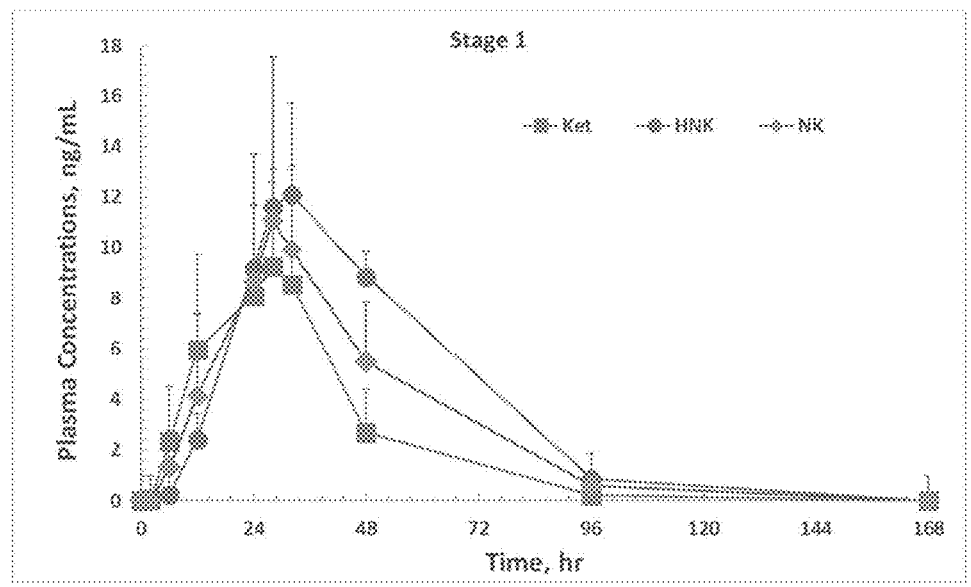
FIG. 5 presents a graph showing the mean concentrations of ketamine, hydroxynorktemine (HNK) and norketamine vs. time profile observed for stage 1 of the clinical study herein.

As detailed herein, the PK parameters of ketamine and its two metabolites (norketamine (NK) and hydroxylnorketamine (HNK)) were determined by a non-compartmental analysis method and are summarized in FIG. 5 and Table 2C. The PK profiles of ketamine, norketamine and hydroxynorketamine from the tested ketamine patches showed slow-rising plasma concentrations, low $C_{max}$ and prolonged exposure. Compared to the values reported previously for a typical 40-min intravenous infusion at 0.5 mg/kg (Clements, et al., 1982; Shaffer 2014), the $C_{max}$ values of ketamine for the tested ketamine patch were about 15-20 fold lower, while the AUC values of ketamine were comparable (about 500 ng/mL·hr). The concentrations of ketamine declined to minimal values at 96 hours and below quantification limit at 168 hours post dose. Generally, the AUC values followed the ascending order of ketamine, norketamine and hydroxylnorketamine. The mean AUC ratio of hydroxynorketamine over ketamine was about 1.40 at Stages 3 and 1.54 at Stage 1.

Figure 4:
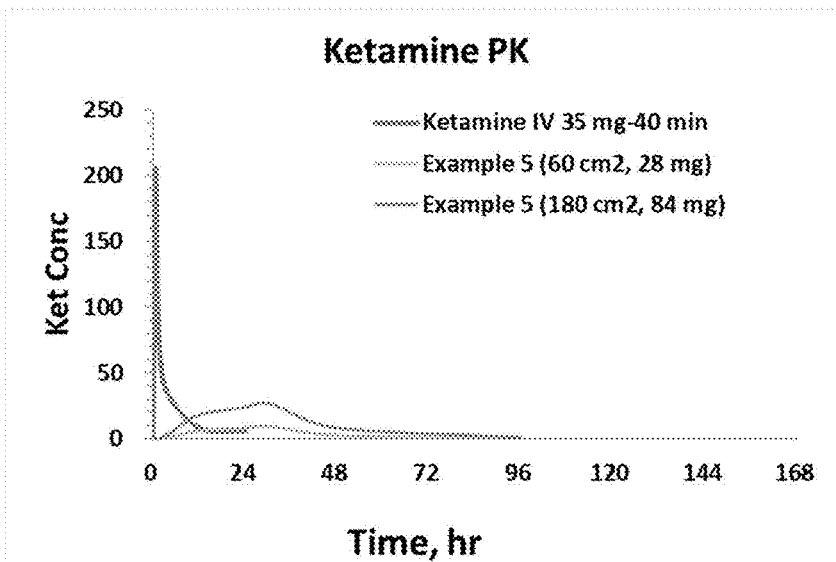
FIG. 4 presents a graph comparing ketamine plasma PK among the following treatments: the typical 40-min infusion of 35 mg of ketamine, ketamine transdermal patch of 60 cm$^2$ (actually observed, labeled as Example 5, 60 cm$^2$, 28 mg) applied for a duration of about 24 hours, and ketamine transdermal patch of 180 cm$^2$ (predicted, labeled as Example 5, 180 cm$^2$, 84 mg) applied for a duration of about 24 hours.

The comparison of PK profiles of ketamine between the typical 40-min intravenous infusion at 0.5 mg/kg and the tested ketamine patch (60 cm$^2$ and 180 cm$^2$) is shown in FIG. 4. It is clear that the time-course profiles are substantially different. The 40-min infusion showed a rapid rising phase and reached a very high peak concentration, whereas the tested ketamine patch demonstrated a slow rising and pronged exposure even after 24 hour when the patch was removed. The PK profile for the 60 cm$^2$ patch was observed, and PK profile for the 180 cm$^2$ patch is estimated by assuming PK linearity with patch sizes. The PK profiles are completely different between tested ketamine patch and commonly used dose method.

Importantly, the relationship between metabolites and parent drug ketamine is completely changed as well. The most notable is the relationship between hydroxynorketamine (HNK) and ketamine. There has been very limited data on monitoring HNK pharmacokinetics in humans in a robust approach. Zarate et al reported some PK data of ketamine and HNK in MDD patients with limited sampling points following a typical 40-min IV infusion of 35 mg of ketamine (Zarate et al. Biol Psychiatry. 2012 Aug. 15; 72(4): 331-338). Digitization of the limited data set and estimation of basic parameters of ketamine and HNK showed that the ratios of AUC of HNK/Ketamine 0.522, and the ratios of $C_{max}$ of HNK/ketamine was about 0.113. The corresponding ratio for the tested ketamine patch were 2.23 and 1.19, respectively. Additionally, as shown in details in the Examples section, it was discovered that by applying the tested ketamine patch to human patents for a duration of 24 hours which delivered about 28 mg or 51 mg of ketamine, a unique PK profile was obtained. For example, the PK profile is characterized by a prolonged exposure of hydroxynorketamine (HNK), with a plasma concentration of about 10 ng/ml at 48 hours post application of the tested ketamine patch at 28 mg dose, and about 6 ng/ml even at 72 hours post application. Therefore, the novel delivery method of the tested ketamine patch completely changes the drug disposition and metabolism of ketamine. It is important to note that many preclinical studies showed that HNK may be the major or only antidepressant entity from dosing ketamine. Also HNK was shown preclinically to have lower potential of AEs. In a similar manner, the relationship between norketamine and ketamine changed significantly as well. The ratio of AUC of NK/Ketamine 0.989, and the ratio of $C_{max}$ of NK/ketamine was about 0.362. The corresponding ratio for the tested ketamine patch were 1.40 and 1.08, respectively. NK is less potent towards NMDAR than ketamine, therefore, increased ratio of NK to ketamine may lower the potential of AE as well. In summary, the tested ketamine patch delivered ketamine in a unique manner, resulting in a completely novel drug disposition of ketamine and metabolites (especially HNK), which offers excellent pharmacological profiles by significantly lowering the peak concentrations, thus reducing AEs.

This unique PK profile is achieved in part due to the continuously high flux of ketamine from the transdermal patches herein. For example, the in vitro permeation studies show that the transdermal patches can maintain a high flux for at least 48 hours, see e.g., FIG. 2. Residual drug analysis from the worn patched also showed that the dose absorbed into body from a 60 cm$^2$ patch at Stage 1 is about 28 mg in 24 hours. This result is anticipated based on in vitro permeability data (24 mg in 24 hour as predicted). The 60 cm$^2$ can be used for up to 72 hours, which can deliver about 84 mg. The residual drug analysis for 20 and 60 cm$^2$ patches at Stage 3 showed slightly higher (about 30%) absorption of ketamine per cm$^2$ per day comparing to that at Stage 1. At a commercial viable size of 180 cm$^2$, various total doses can be delivered to a subject, such as 84 to 100 mg in 24 hours, or 252-300 mg in 72 hours. In the transdermal field, delivery of drugs over 40 mg is rare, because the skin is a strong protective natural barrier. Typical delivery dose with transdermal products is below 10 mg.

Figure 6:
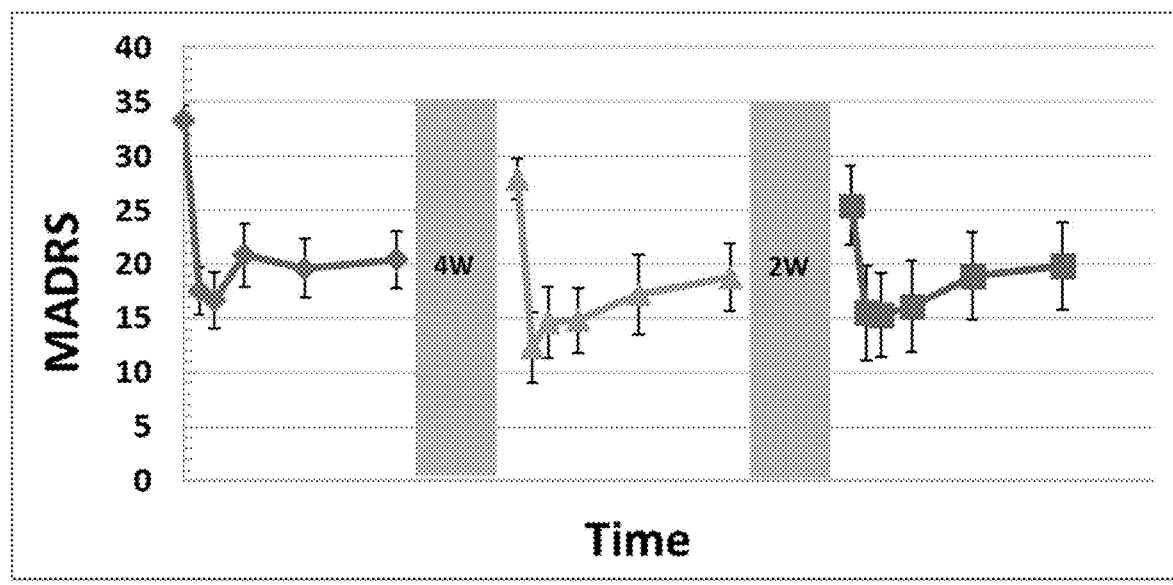
FIG. 6 presents a graph showing the mean Montgomery-Asberg Depression Rating Scale (MADRS) total score at three stages of the clinical study herein.
Figure 9:
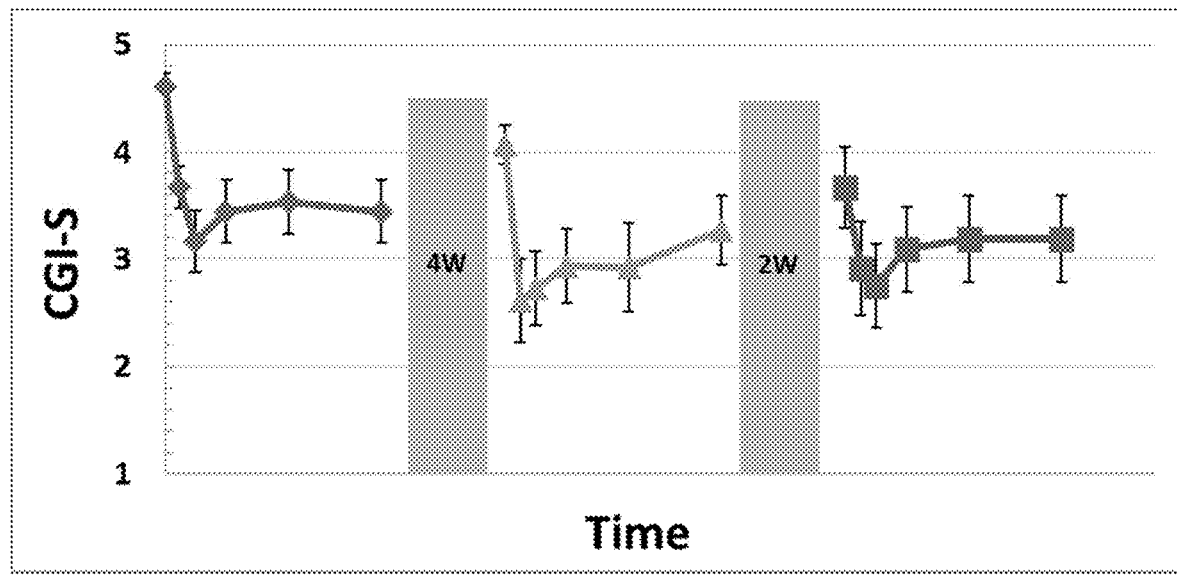
FIG. 9 presents a graph showing the mean Clinical Global Impressions-Severity (CGI-S) total score at three stages of the clinical study herein.

Further, it was discovered that the observed unique PK profile is associated with PD effect. Ad discussed herein, exploratory pharmacodynamic assessment of ketamine transdermal patch included assessment of treatment response based on the Montgomery-Asberg Depression Rating Scale (MADRS), Clinical Global Impressions-Severity (CGI-S), and Symptoms of Depression Questionnaire (SDQ) scores. The mean MADRS scores across the three study stages are shown in FIG. 6. The changes (least square means) of CGI-S at each stage are shown in FIG. 9. Substantial reductions in MADRS from baseline were observed in all three stages. Survey was conducted to collect ALL studies with the MADRS scale assessed after a single dose of ketamine or esketamine. These reductions are substantial and in comparable or greater magnitude than the other ketamine or esketamine studies with other dosing methods (IV infusion or intranasal).

Figure 7:
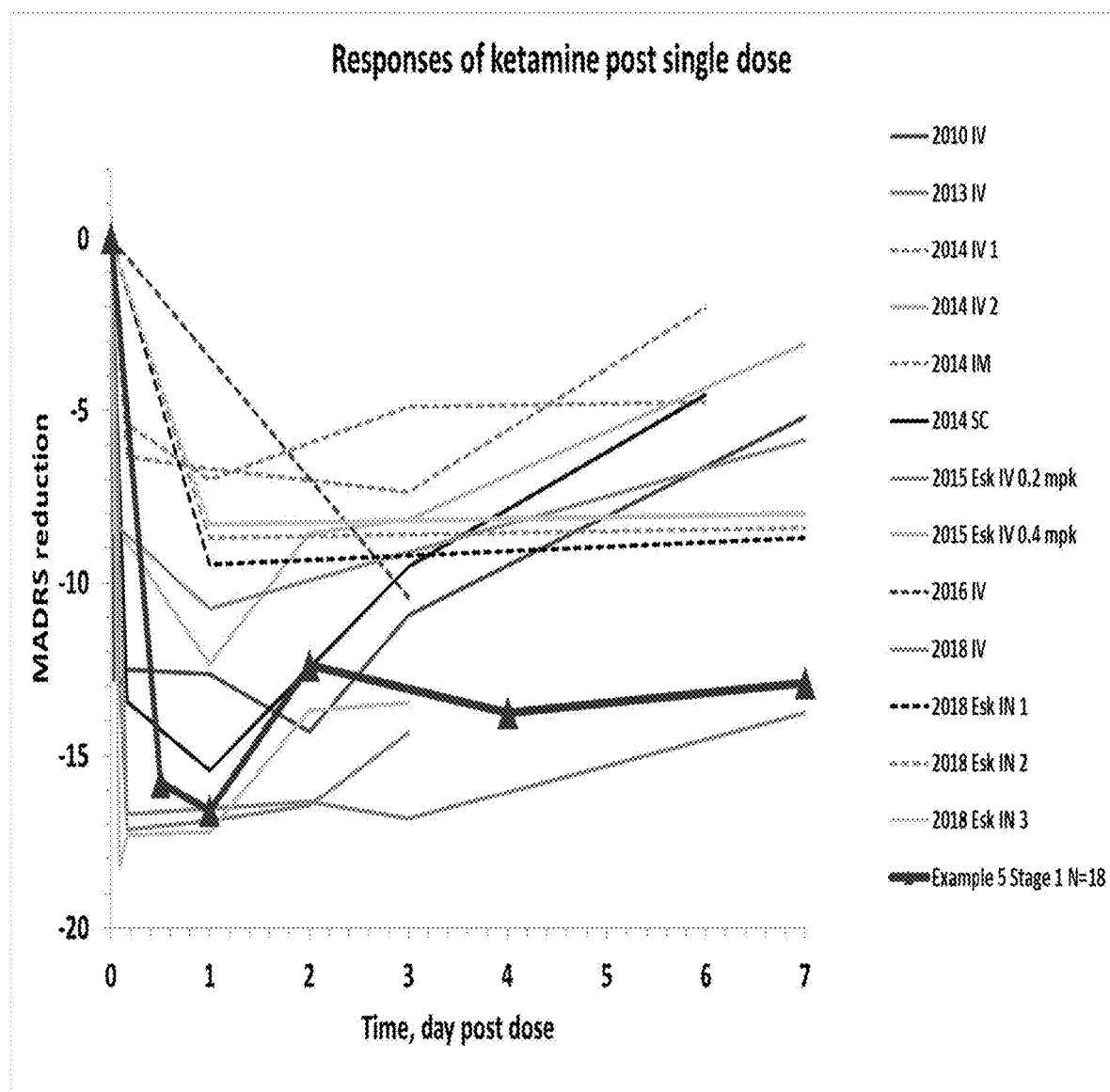
FIG. 7 presents a graph comparing antidepressant effects (MADRS total score changes) of a single dose of the tested ketamine transdermal patch vs other studies with MADRS data after a single dose of ketamine or esketamine.
Figure 8:
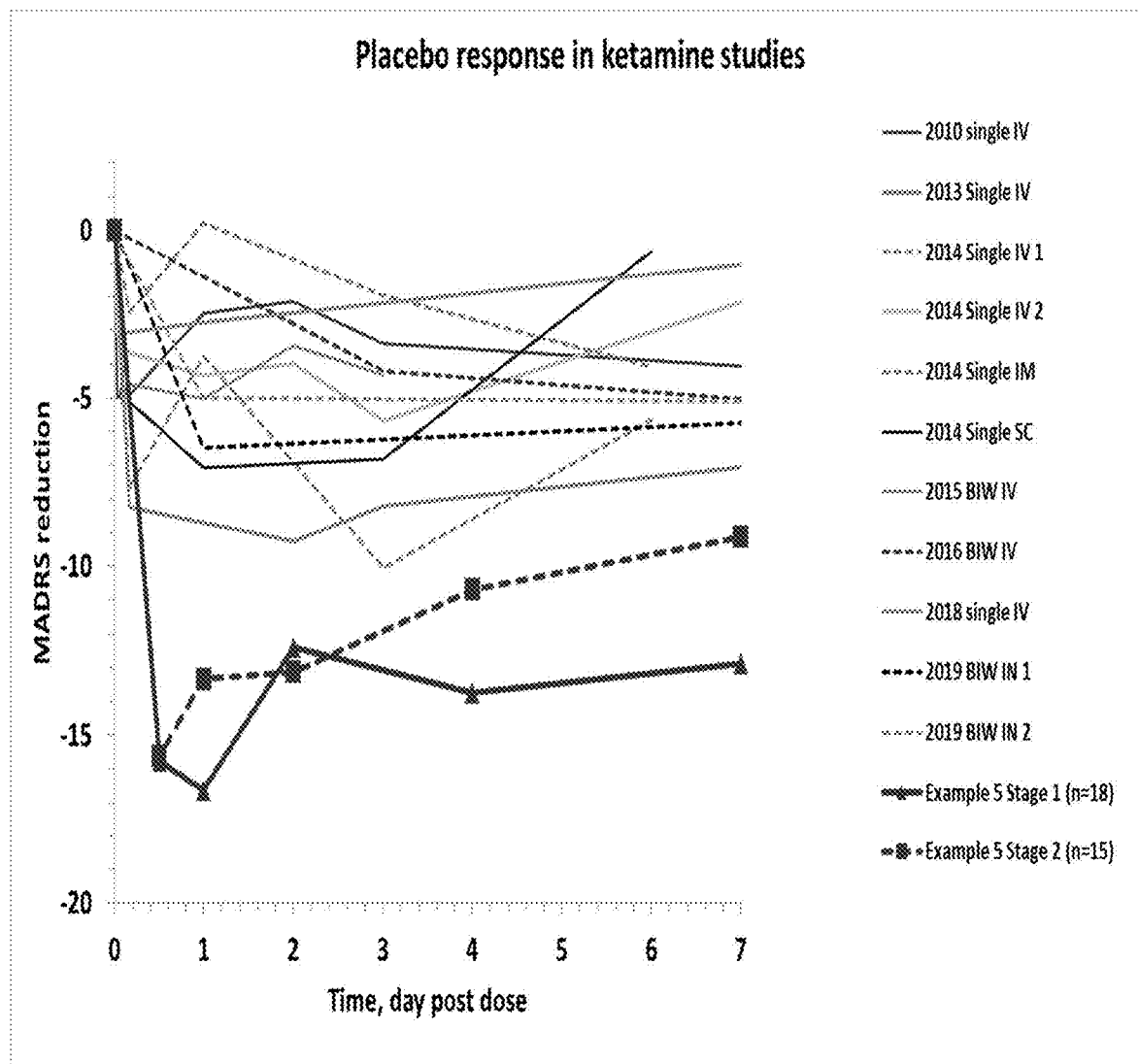
FIG. 8 presents a graph comparing placebo effects (MADRS total score changes) observed in the clinical study herein vs other studies with MADRS data after placebo treatments.

Specifically, antidepressant effects were observed in all stages, and such effects were larger comparing to those typically seen in other ketamine studies (FIGS. 7 and 8). Placebo stage (stage 2) also showed substantial decreases in MADRS (FIG. 8). Placebo effect in depression study is very normal. The large placebo drop in this study were much larger than those from other studies as surveyed (FIG. 8). The explanation was called conditioned effect (on Stage 1). This study was done in a sequential manner, with a low dose (28 mg) at Stage 1, followed by placebo (Stage 2), and then a high dose (about 53 mg) at Stage 3. The study was blinded to patients, meaning that patients did not know if they receive a ketamine patch or a placebo patch. The significant antidepressant effect exerted at Stage 1 can bleed into Stage 2; in other words, the patients have experienced the antidepressant effects from Stage 1, therefore, the patients have the expectation that they received the ketamine dose as well, thus psychologically approved their mood etc. This phenomenon is common in psychiatry field. Such conditioning effect has been found with ketamine in animal studies (Samuel R. Krimmel, Panos Zanos, Polymnia Georgiou Luana Colloca, Todd D. Gould. Classical conditioning of antidepressant placebo effects in mice, Psychopharmacology. August 2019). Importantly, the antidepressant effects were observed in a relative prolonged manner for the entire week (see FIG. 7). Typically after single dose of ketamine by IV infusion or intranasal spray, the antidepressant effect only lasted for about 3 days, and at the end of the week, the effect typically returns to baseline. The prolonged antidepressant effect is presumably due to the prolonged PK exposure of ketamine and HNK from dosing the tested ketamine patch. Further, importantly, the baseline dropped from Stage 1 to Stages 2 and 3 (FIG. 6). This indicated that the antidepressant effects were a long-term effect, even after ketamine or metabolites are completely cleared in the body. This also supports the antidepressant efficacy of the tested ketamine patch, since the baseline effect already existed (prolonged from Stage 1 active dose) before the placebo was administered. CGI-S as another scale measuring antidepressant effect showed the similar effect as MADRS, including large drop from baseline, decreasing baseline from Stages 1 to 2 and 3.

Figure 10:
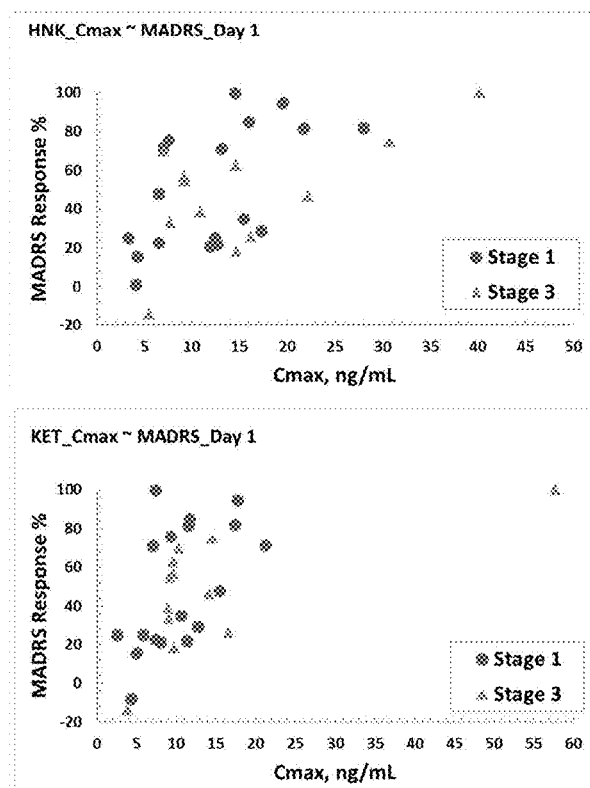
FIG. 10 shows plots of MADRS response percentages vs. $C_{max}$ of HNK or Ketamine observed at stages 1 and 3 of the clinical study herein. This figure shows the pharmacokinetic and pharmacodynamics (antidepressant effects in MADRS change) following a single dose of ketamine transdermal patch on Day 1 when the concentration reached around $T_{max}$ (around 24 hours post the application of the transdermal ketamine patch).

Moreover, individual concentration vs the antidepressant effect around the $T_{max}$ demonstrated PK/PD correlation, which indicated that the antidepressant effects can be further strengthened when the dose or concentration of ketamine and/or HNK increases (FIG. 10). The relationship showed that when the concentration of ketamine and/or HNK increases to 20-30 ng/mL, the MADRS response reaches about the near maximal effects with dosing the tested ketamine patch. Thus, delivery about 100 mg dose by a ketamine transdermal delivery device, which will result a $C_{max}$ around 30 ng/mL for ketamine and HNK with prolonged exposure over 24 hours or more, can further enhance the antidepressant effects.

Based in part on the observed PK and PD associated with ketamine patches, the present disclosure also provides various novel methods of treating depression (e.g., major depressive disorder, treatment resistant depression, or bipolar depression) in a subject in need thereof. In some embodiments, the method comprises administering to the subject a therapeutically effective plasma concentration of ketamine, hydroxynorketamine, and norketamine. In some embodiments, the method comprises administering to the subject a transdermal delivery device comprising ketamine, and administering to the subject a placebo transdermal delivery device, wherein the placebo transdermal delivery device is substantially the same as the transdermal delivery device comprising ketamine, except that the placebo transdermal delivery device does not contain ketamine. In some embodiments, the method comprises administering to the subject a transdermal delivery device comprising ketamine to transdermally deliver a dose of about 60 mg to about 120 mg of ketamine, such as about 100 mg of ketamine to the subject. In some embodiments, the method comprises administering to the subject a transdermal delivery device comprising ketamine to transdermally deliver a sufficient amount of ketamine to the subject to achieve a $C_{max}$ of ketamine of about 5-50 ng/mL such as about 10-30 ng/ml and/or a $C_{max}$ of hydroxynorketamine of about 5-50 ng/mL such as about 10-30 ng/ml.

For example, in some embodiments, the present disclosure provides a method of treating depression in a subject in need thereof, the method comprising administering to the subject a therapeutically effective plasma concentration of ketamine, hydroxynorketamine, and norketamine. As used herein, a therapeutically effective plasma concentration of ketamine, hydroxynorketamine, and norketamine does not require that ketamine, hydroxynorketamine and norketamine each independently be effective in treating depression. It suffices that the combined plasma exposure of ketamine, hydroxynorketamine and norketamine is effective in treating depression. In some embodiments, the therapeutically effective plasma concentration of ketamine, hydroxynorketamine, and norketamine, when observed from 0-96 hours, can be characterized by (1) a $C_{max}$ of ketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml and/or a $C_{max}$ of hydroxynorketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml; (2) a ratio of area under the curve from 0-96 hours ($AUC_{0-96}$) of hydroxynorketamine to ketamine ranging from about 1 to about 3, such as about 1, about 1.5, about 2, about 2.5, or about 3, or any range between the recited value such as about 1-2 or about 1.5-2.5, etc.; (3) a ratio of area under the curve from 0-96 hours ($AUC_{0-96}$) of norketamine to ketamine ranging from about 1 to about 2, such as about 1, about 1.2, about 1.5, about 1.8, or about 2, or any range between the recited value, such as about 1-1.5 or 1-1.8, etc.; (4) a ratio of $C_{max}$ of hydroxynorketamine to ketamine during 0-96 hours ranging from about 0.7 to about 1.5, such as about 0.8, about 1, about 1.2, about 1.5, or any ranges between the recited values, such as about 0.8-1.5 or about 1-1.5, etc.; (5) a ratio of $C_{max}$ of norketamine to ketamine during 0-96 hours ranging from about 0.7 to about 1.5, such as about 0.8, about 1, about 1.2, about 1.5, or any ranges between the recited values, such as about 0.8-1.5 or about 1-1.5, etc.; or (6) any combination of (1)-(5), such as (1), (2) and (4), (1), (3), and (5), (1) and (2), (1) and (4), (1) and (3), (1) and (5), (1), (2), and (3), (1), (4), and (5), or all of (1)-(5). The term "0-96" hours should be understood as from the initial point of administration of ketamine, hydroxyketamine, and/or norketamine until 96 hours after. For example, in the case of administering a transdermal patch, "0-96" hours should be understood as from the initial applying of the patch until 96 hours post application, the patch however may be removed for example around 24 hours post application. In some embodiments, the therapeutically effective plasma concentration of ketamine, hydroxynorketamine, and norketamine can be effective in delaying a recurring depressive episode. In some embodiments, the therapeutically effective plasma concentration of ketamine, hydroxynorketamine, and norketamine can be effective in alleviating one or more symptoms associated with the depression (e.g., major depressive disorder). In some embodiments, the therapeutically effective plasma concentration of ketamine, hydroxynorketamine, and norketamine can be effective in reducing the MADRS score, CGI-S score, and/or SDQ score.

Typically, the therapeutically effective plasma concentration of ketamine, hydroxynorketamine, and norketamine can be achieved through administering a transdermal delivery device, such as a transdermal delivery device comprising ketamine. In some embodiments, the transdermal delivery device can be free of hydroxynorketamine. In some embodiments, the transdermal delivery device can be free of norketamine. In some embodiments, the transdermal delivery device can be free of hydroxynorketamine and norketamine. In some embodiments, the therapeutically effective plasma concentration of ketamine, hydroxynorketamine, and norketamine can be achieved through administering a transdermal delivery device comprising ketamine (e.g., described herein, such as those described in [1]-[18], [23], or [83] of the Brief Summary, or any of the monolithic patches described herein). In some embodiments, the transdermal delivery device comprising ketamine is applied to deliver ketamine to the subject at a dose of about 15 mg to about 150 mg of ketamine, such as about 15 mg to about 30 mg, about 30 mg to about 60 mg (e.g., about 50 mg), about 60 mg to about 120 mg (e.g., about 100 mg), or about 75 mg to about 150 mg, over a period of time ranging from about 8 hours to about 72 hours, preferably, about 24 hours to about 48 hours, such as about 24 hours or about 48 hours. In some embodiments, the transdermal delivery device is administered with a dosing frequency ranging from once a day to once every week. In some preferred embodiments, the method comprises administering the transdermal delivery device to the subject 1-3 times every week, more preferably, once in at least 3 days, such as once a week or twice a week. In some embodiments, there is a gap period between two consecutive doses of ketamine. In some embodiments, one or more placebo transdermal delivery devices can be applied to the subject during the gap period as described herein. In some embodiments, there is no gap period between two consecutive doses of ketamine. For each application, the transdermal delivery device is typically applied to the subject for a duration of about 24 hours (i.e., the patch-on period is about 24 hours) to deliver the desired dose of ketamine, although a longer duration such as two days or shorter duration such as about 8-16 hours can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The subject is not particularly limited and includes any of those described herein having a depression, typically recurrent or chronic depression. For example, in some embodiments, the subject is characterized as having a MDD. In some embodiments, the subject is characterized as having a MADRS≥20. In some embodiments, the subject is characterized as having failed at least one antidepressant treatment based on the MGH ATRQ. In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has recurrent major depressive disorder. In some embodiments, the subject does not have a current depressive episode or is in remission. In some embodiments, the subject has chronic major depressive disorder. In some embodiments, the subject is characterized as having treatment resistant depression. In some embodiments, the method further comprises administering to the subject one or more additional antidepressant treatments, such as oral antidepressants or another ketamine related antidepressant such as intranasal ketamine treatment.

In some embodiments, a method is provided for treating depression in a subject in need thereof, the method comprising administering to the subject a transdermal delivery device comprising ketamine, and administering to the subject a placebo transdermal delivery device. Typically, the placebo transdermal delivery device is substantially the same as the transdermal delivery device comprising ketamine, except that the placebo transdermal delivery device does not contain ketamine. As used herein, a placebo transdermal delivery device is considered substantially the same as the transdermal delivery device comprising ketamine other than not containing ketamine, when the placebo transdermal delivery device has the same other ingredients in the same proportions and has the same size, within experimental errors. For example, a 20 cm$^2$ placebo patch of Example 1B is considered substantially the same as a 20 cm$^2$ ketamine patch of Example 1A except that the placebo transdermal delivery device does not contain ketamine.

Typically, the first administration is an administration of the transdermal delivery device comprising ketamine (e.g., described herein, such as those described in [1]-[18], [23], or [83] of the Brief Summary, or any of the monolithic patches described herein). In some embodiments, the first administration can be administering the transdermal delivery device comprising ketamine to deliver ketamine to the subject at a dose of about 15 mg to about 150 mg (such as about 15 mg to about 30 mg, about 30 mg to about 60 mg (e.g., about 50 mg), about 60 mg to about 120 mg (e.g., about 100 mg), or about 75 mg to about 150 mg) over a period of time ranging from about 8 hours to about 72 hours, preferably about 24 hours or 48 hours. In some embodiments, the transdermal delivery device comprising ketamine and placebo transdermal delivery device are administered at a frequency ranging from once a day to once a week, preferably, 1-3 times a week, more preferably, once in at least 3 days such as once a week or twice a week, wherein each administration is independently an administration of the transdermal delivery device comprising ketamine or the placebo transdermal delivery device. In some embodiments, the dosing regimen can also include a no treatment (no ketamine and no placebo patch) period. For example, in some embodiments, the subject can be administered a transdermal delivery device comprising ketamine, followed by no treatment (no ketamine and no placebo patch) for a period ranging from 1 week to 6 weeks, before administering the next transdermal delivery device, which can also be either a substantially the same transdermal delivery device comprising ketamine or a substantially the same placebo transdermal delivery device (except without ketamine). Preferably, in such regimen, it is preferred that the next transdermal delivery device after the no treatment period is not a placebo treatment. For each application, the transdermal delivery device comprising ketamine or the placebo transdermal delivery device is typically applied to the subject for a duration of about 24 hours (i.e., the patch-on period is about 24 hours), although a longer duration such as two days or shorter duration such as about 8-16 hours can also be used in some cases. Typically, during the patch-on period, the transdermal delivery device comprising ketamine delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The method is not particularly limited to any particular sequence of administering. For example, for a once a week administration frequency, the first week can be an administration of a transdermal delivery device comprising ketamine, the second week can be an administration of a transdermal delivery device comprising ketamine or a placebo transdermal delivery device, the third week can be an administration of a transdermal delivery device comprising ketamine or a placebo transdermal delivery device, etc. In some embodiments, one or two administration of the placebo transdermal delivery device is followed after every one or two administrations of the transdermal delivery device comprising ketamine. In some embodiments, every administration of a transdermal delivery device comprising ketamine can be followed by an administration of a placebo transdermal delivery device. In some embodiments, every 2, 3, or 4 administrations of a transdermal delivery device comprising ketamine can be followed by an administration of a placebo transdermal delivery device. In some embodiments, every administration of a transdermal delivery device comprising ketamine can be followed by 2, 3, or 4 administrations of a placebo transdermal delivery device. In some embodiments, every 2, 3, or 4 administrations of a transdermal delivery device comprising ketamine can be followed by 2, 3, or 4 administration of a placebo transdermal delivery device. Other dosing arrangements can also be suitable.

In some embodiments, the method of administering both ketamine and placebo transdermal delivery device can also have no gap period, i.e., the subject wears a ketamine or a placebo patch in a substantial continuous fashion. For example, in some embodiments, the transdermal delivery device comprising ketamine is applied for a duration of about 24 hours, which can be replaced with the substantially the same placebo transdermal delivery device, and after being applied for a duration of also about 24 hours, it can be replaced with a new transdermal delivery device comprising ketamine or placebo transdermal delivery device, depending on the ketamine dosing frequency.

The subject is not particularly limited and includes any of those described herein having a depression, typically recurrent or chronic depression. For example, in some embodiments, the subject is characterized as having a MDD. In some embodiments, the subject is characterized as having a MADRS≥20. In some embodiments, the subject is characterized as having failed at least one antidepressant treatment based on the MGH ATRQ. In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has recurrent major depressive disorder. In some embodiments, the subject does not have a current depressive episode or is in remission. In some embodiments, the subject has chronic major depressive disorder. In some embodiments, the subject is characterized as having treatment resistant depression. In some embodiments, the method further comprises administering to the subject one or more additional antidepressant treatments, such as oral antidepressants or another ketamine related antidepressant such as intranasal ketamine treatment.

In some embodiments, a method is provided for treating depression in a subject in need thereof, the method comprising administering to the subject a transdermal delivery device comprising ketamine to transdermally deliver a dose of about 60 mg to about 120 mg of ketamine, such as about 100 mg of ketamine to the subject. In some embodiments, the transdermal delivery device comprising ketamine can be those described herein, such as those described in [1]-[18], [23], or [83] of the Brief Summary, or any of the monolithic patches described herein. In some embodiments, the transdermal delivery device is administered with a dosing frequency ranging from once a day to once every week. In some preferred embodiments, the method comprises administering the transdermal delivery device to the subject 1-3 times every week, more preferably, once in at least 3 days, such as once a week or twice a week. In some embodiments, there is a gap period between two consecutive doses of ketamine. In some embodiments, one or more placebo transdermal delivery devices can be applied to the subject during the gap period as described herein. In some embodiments, there is no gap period between two consecutive doses of ketamine. For each application, the transdermal delivery device is typically applied to the subject for a duration of about 24 hours (i.e., the patch-on period is about 24 hours) to deliver the desired dose of ketamine, although a longer duration such as two days or shorter duration such as about 8-16 hours can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The subject is not particularly limited and includes any of those described herein having a depression, typically recurrent or chronic depression. For example, in some embodiments, the subject is characterized as having a MDD. In some embodiments, the subject is characterized as having a MADRS≥20. In some embodiments, the subject is characterized as having failed at least one antidepressant treatment based on the MGH ATRQ. In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has recurrent major depressive disorder. In some embodiments, the subject does not have a current depressive episode or is in remission. In some embodiments, the subject has chronic major depressive disorder. In some embodiments, the subject is characterized as having treatment resistant depression. In some embodiments, the method further comprises administering to the subject one or more additional antidepressant treatments, such as oral antidepressants or another ketamine related antidepressant such as intranasal ketamine treatment.

In some embodiments, a method is provided for treating depression in a subject in need thereof, the method comprising administering to the subject a transdermal delivery device comprising ketamine to transdermally deliver sufficient amount of ketamine to the subject to achieve a $C_{max}$ of ketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml and/or a $C_{max}$ of hydroxynorketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml. In some embodiments, the transdermal delivery device comprising ketamine can be any of those described herein, such as those described in [1]-[18], [23], or [83] of the Brief Summary, or any of the monolithic patches described herein. In some embodiments, the transdermal delivery device comprising ketamine is applied to deliver a dose of ketamine to the subject of about 60 mg to about 120 mg or about 75 mg to about 150 mg of ketamine, to achieve the $C_{max}$ of ketamine of about 5-50 ng/mL and/or the $C_{max}$ of hydroxynorketamine of about 5-50 ng/mL. In some embodiments, the transdermal delivery device is administered with a dosing frequency ranging from once a day to once every week. In some preferred embodiments, the method comprises administering the transdermal delivery device to the subject 1-3 times every week, more preferably, once in at least 3 days, such as once a week or twice a week. In some embodiments, there is a gap period between two consecutive doses of ketamine. In some embodiments, there is no gap period between two consecutive doses of ketamine. For each application, the transdermal delivery device is typically applied to the subject for a duration of about 24 hours (i.e., the patch-on period is about 24 hours), although a longer or shorter duration can also be used in some cases. Typically, during the patch-on period, the transdermal delivery device delivers ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The subject is not particularly limited and includes any of those described herein having a depression, typically recurrent or chronic depression. For example, in some embodiments, the subject is characterized as having a MDD. In some embodiments, the subject is characterized as having a MADRS≥20. In some embodiments, the subject is characterized as having failed at least one antidepressant treatment based on the MGH ATRQ. In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has recurrent major depressive disorder. In some embodiments, the subject does not have a current depressive episode or is in remission. In some embodiments, the subject has chronic major depressive disorder. In some embodiments, the subject is characterized as having treatment resistant depression. In some embodiments, the method further comprises administering to the subject one or more additional antidepressant treatments, such as oral antidepressants or another ketamine related antidepressant such as intranasal ketamine treatment.

In some embodiments, a method is provided for screening or selecting a candidate transdermal delivery device for treating a disease or disorder described herein, such as depression or pain, the method comprising (1) determining a ketamine flux profile of the candidate transdermal delivery device, (2) optionally administering the candidate transdermal delivery device to a subject, and (3) optionally selecting the candidate transdermal delivery device that provides any of the ketamine flux profile and/or PK profile described herein, such as a mean $C_{max}$ of ketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml and/or a $C_{max}$ of hydroxynorketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml. In some embodiments, the method comprises selecting a candidate transdermal delivery device that provides an in vitro permeation profile characterized by a ketamine permeation rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine, which can be substantially constant for a period of time ranging from about 8 hours to about 72 hours, such as up to 48 hours or up to 72 hours, when tested in vitro with human cadaver skin. In some embodiments, the method comprises selecting a candidate transdermal delivery device that provides a PK profile characterized by (1) a $C_{max}$ of ketamine of about 5-50 ng/mL such as about 10-30 ng/ml and/or a $C_{max}$ of hydroxynorketamine of about 5-50 ng/mL such as about 10-30 ng/ml; (2) a ratio of area under the curve from 0-96 hours ($AUC_{0-96}$) of hydroxynorketamine to ketamine ranging from about 1 to about 3, such as about 1, about 1.5, about 2, about 2.5, or about 3, or any range between the recited value such as about 1-2 or about 1.5-2.5, etc.; (3) a ratio of area under the curve from 0-96 hours ($AUC_{0-96}$) of norketamine to ketamine ranging from about 1 to about 2, such as about 1, about 1.2, about 1.5, about 1.8, or about 2, or any range between the recited value, such as about 1-1.5 or 1-1.8, etc.; (4) a ratio of $C_{max}$ of hydroxynorketamine to ketamine during 0-96 hours ranging from about 0.7 to about 1.5, such as about 0.8, about 1, about 1.2, about 1.5, or any ranges between the recited values, such as about 0.8-1.5 or about 1-1.5, etc.; (5) a ratio of $C_{max}$ of norketamine to ketamine during 0-96 hours ranging from about 0.7 to about 1.5, such as about 0.8, about 1, about 1.2, about 1.5, or any ranges between the recited values, such as about 0.8-1.5 or about 1-1.5, etc.; or (6) any combination of (1)-(5), such as (1), (2) and (4), (1), (3), and (5), (1) and (2), (1) and (4), (1) and (3), (1) and (5), (1), (2), and (3), (1), (4), and (5), or all of (1)-(5). In some embodiments, the method comprises selecting a candidate transdermal delivery device that provides both an in vitro permeation profile described herein and a PK profile described herein. The candidate transdermal delivery device is not particularly limited. For example, the candidate transdermal delivery device can be any of those described herein such as those described in [1]-[18], [23], or [83] of the Brief Summary, or any of the monolithic patches described herein, or those described in or can be prepared from U.S. Patent Application Publication Nos. 2018/0353437 and 2020/0030251, the content of each of which is herein incorporated by reference in its entirety. In some embodiments, the present disclosure also provides a method of treating a disease or disorder herein, such as depression or pain, comprising administering to a subject in need thereof the selected candidate transdermal delivery device herein, such as those selected that provide either or both of an in vitro permeation profile described herein and a PK profile described herein.

In some embodiments, the present disclosure also provides a method of treating depression comprising administering to a subject in need thereof one or more monolithic patches herein. The one or more monolithic patches are typically selected to deliver a therapeutically effective amount of ketamine to the subject. In some embodiments, the therapeutically effective amount of ketamine is a dose of about 15 mg to about 250 mg of ketamine, wherein the dose is delivered to the subject over a period of time ranging from about 8 hours to about 72 hours, preferably, about 24 hours to about 48 hours, such as about 24 hours or about 48 hours. In some embodiments, the therapeutically effective amount of ketamine is a dose of about 15 mg to about 30 mg of ketamine. In some embodiments, the therapeutically effective amount of ketamine is a dose of about 30 mg to about 60 mg of ketamine (e.g., about 50 mg). In some embodiments, the therapeutically effective amount of ketamine is a dose of about 60 mg to about 120 mg (e.g., about 100 mg) of ketamine. In some embodiments, the therapeutically effective amount of ketamine is a dose of about 75 mg to about 150 mg of ketamine.

Various combinations of monolithic patches can be used to deliver the therapeutically effective amount of ketamine to the subject. Typically, the desired combination will take into consideration the patch size, the ketamine delivery rate of the monolithic patch, the desired total dose to achieve a therapeutically effect, and other considerations known to those skilled in the art. In some embodiments, a single patch with a size up to 180 cm$^2$ can be used to deliver a desired dose. As detailed herein, the monolithic patches herein can individually deliver up to at least about 60-110 mg/day. In some embodiments, the desired dose can be achieved by combining several, such as 2 or 3 smaller patches, such as those having an active surface area of about 20 cm$^2$ to about 100 cm$^2$, such as about 20 cm$^2$, about 30 cm$^2$, about 40 cm$^2$, about 50 cm$^2$, about 60 cm$^2$, about 70 cm$^2$, about 80 cm$^2$, about 90 cm$^2$, or about 100 cm$^2$.

In some embodiments, the method comprises applying a monolithic patch having an active surface area of about 20 cm$^2$ to about 180 cm$^2$ such as a monolithic patch having an active surface area of about 20 cm$^2$ and about 24.7 mg of ketamine, an active surface area of about 40 cm$^2$ and about 49.6 mg of ketamine, an active surface area of about 60 cm$^2$ and about 87.3 mg of ketamine, an active surface area of about 80 cm$^2$ and about 100 mg of ketamine, an active surface area of about 90 cm$^2$ and about 112.5 mg of ketamine, an active surface area of about 100 cm$^2$ and about 124.7 mg of ketamine, an active surface area of about 120 cm$^2$ and about 150 mg of ketamine, or an active surface area of about 180 cm$^2$ and about 225 mg of ketamine, wherein the monolithic patch includes a) a backing layer (e.g., described herein); b) a drug-in-adhesive layer, which comprises i) ketamine in an amount of about 14-17% by weight; ii) oleyl oleate and levulinic acid, each in an amount of about 4-7% by weight; iii) a polyvinyl pyrrolidone-co-vinyl acetate in an amount of about 15-25% by weight; iv) a polyacrylate adhesive, such as a carboxylate-functionalized polyacrylate-vinylacetate copolymer in an amount of about 45-55% by weight; and v) an antioxidant in an amount of about 0.01-1% by weight; and c) a release liner (e.g., described herein). In some embodiments, the ketamine is in an amount of about 14%, about 15%, about 16%, or about 17% by weight of the DIA layer. In some embodiments, each of the oleyl oleate and levulinic acid is independently present in an amount of about 4%, about 5%, about 6%, or about 7% by weight of the DIA layer. In some embodiments, the polyvinyl pyrrolidone-co-vinyl acetate, such as Kollidon VA-64, can be present in an amount of about 15%, about 16%, about 17%, about 18%, about 19%, about 20%, about 21%, about 22%, about 23%, about 24%, about 25%, or any range between the recited value such as about 20-25%, by weight of the DIA layer. In some embodiments, the polyacrylate adhesive is a carboxylate-functionalized polyacrylate-vinylacetate copolymer, such as Duro Tak 87-2677, which can be in an amount of about 45%, about 50%, about 55%, or any range between the recited values by weight of the DIA layer. In some embodiments, the DIA layer comprises the antioxidant. In some embodiments, the antioxidant can be a phenol antioxidant, such as butylated hydroxytoluene. In some embodiments, the antioxidant can be present in an amount of about 0.01%, about 0.1%, about 0.2%, about 0.3%, about 0.4%, about 0.5%, about 0.6%, about 0.7%, about 0.8%, about 0.9%, about 1%, or any ranges between the recited value such as about 0.1-1%, about 0.3-0.7%, about 0.5-1.5%, etc. by weight of the DIA layer. In some embodiments, the DIA layer is free of DMSO.

In some embodiments, the method comprises applying a monolithic patch having an active surface area of about 20 cm² to about 180 cm² such as a monolithic patch having an active surface area of about 20 cm² and about 24.7 mg of ketamine, an active surface area of about 40 cm² and about 49.6 mg of ketamine, an active surface area of about 60 cm² and about 87.3 mg of ketamine, an active surface area of about 80 cm² and about 100 mg of ketamine, an active surface area of about 90 cm² and about 112.5 mg of ketamine, an active surface area of about 100 cm² and about 124.7 mg of ketamine, an active surface area of about 120 cm² and about 150 mg of ketamine, or an active surface area of about 180 cm² and about 225 mg of ketamine, wherein the monolithic patch includes a) a backing layer (e.g., described herein); b) a drug-in-adhesive layer, which comprises i) ketamine in an amount of about 15-16%, such as about 15.7% by weight; ii) oleyl oleate and levulinic acid, each in an amount of about 5-6% by weight; iii) a polyvinyl pyrrolidone-co-vinyl acetate in an amount of about 20-25% by weight; iv) a carboxylate-functionalized polyacrylate-vinylacetate copolymer in an amount of about 50-55% by weight; and v) an antioxidant in an amount of about 0.3-0.7%, such as about 0.5% by weight; and c) a release liner (e.g., described herein). In some embodiments, each of the oleyl oleate and levulinic acid is independently present in an amount of about 5%, about 5.5%, or about 6% by weight of the DIA layer. In some embodiments, the polyvinyl pyrrolidone-co-vinyl acetate, such as Kollidon VA-64, can be present in an amount of about 20%, about 21%, about 22%, about 23%, about 24%, about 25%, or any range between the recited value such as about 20-22%, by weight of the DIA layer. In some embodiments, the carboxylate-functionalized polyacrylate-vinylacetate copolymer, such as Duro Tak 87-2677, can be in an amount of about 50%, about 51%, about 52%, about 53%, about 54%, about 55%, or any range between the recited values by weight of the DIA layer. In some embodiments, the antioxidant can be a phenol antioxidant, such as butylated hydroxytoluene. In some embodiments, the DIA layer is free of DMSO.

In some more specific embodiments, the method comprises applying a monolithic patch having an active surface area of about 20 cm² to about 180 cm² such as a monolithic patch having an active surface area of about 20 cm² and about 24.7 mg of ketamine, an active surface area of about 40 cm² and about 49.6 mg of ketamine, an active surface area of about 60 cm² and about 87.3 mg of ketamine, an active surface area of about 80 cm² and about 100 mg of ketamine, an active surface area of about 90 cm² and about 112.5 mg of ketamine, an active surface area of about 100 cm² and about 124.7 mg of ketamine, an active surface area of about 120 cm² and about 150 mg of ketamine, or an active surface area of about 180 cm² and about 225 mg of ketamine, wherein the monolithic patch includes a) a backing layer (e.g., Scotchpak 9723); b) a drug-in-adhesive layer, with ingredients shown in Table A of Example 1A or prepared by the method according to Example 1A; and c) a release liner (e.g., Loparex).

In some embodiments, the method comprises applying one or more monolithic patches independently selected from a monolithic patch having an active surface area of about 20 cm² to about 180 cm² such as a monolithic patch having an active surface area of about 20 cm² and about 24.7 mg of ketamine, e.g., as described herein, which is configured to have a ketamine delivery rate of about 6-16 mg/day; a monolithic patch having an active surface area of about 40 cm² and about 49.6 mg of ketamine, e.g., as described herein, which is configured to have a ketamine delivery rate of about 10-30 mg/day; a monolithic patch having an active surface area of about 60 cm² and about 87.3 mg of ketamine, e.g., as described herein, which is configured to have a ketamine delivery rate of about 20-40 mg/day; a monolithic patch having an active surface area of about 80 cm² and about 100 mg of ketamine, e.g., as described herein, which is configured to have a ketamine delivery rate of about 25-50 mg/day; a monolithic patch having an active surface area of about 90 cm² and about 112.5 mg of ketamine, e.g., as described herein, which is configured to have a ketamine delivery rate of about 30-60 mg/day; a monolithic patch having an active surface area of about 100 cm² and about 124.7 mg of ketamine, e.g., as described herein, which is configured to have a ketamine delivery rate of about 35-70 mg/day; a monolithic patch having an active surface area of about 120 cm² and about 149.6 mg of ketamine, e.g., as described herein, which is configured to have a ketamine delivery rate of about 40-80 mg/day; and a monolithic patch having an active surface area of about 180 cm² and about 225 mg of ketamine, e.g., as described herein, which is configured to have a ketamine delivery rate of about 60-110 mg/day, to deliver to the subject a total dose of about 15 mg to about 150 mg (e.g., about 15 mg, about 30 mg, about 50 mg, about 60 mg, about 75 mg, about 90 mg, about 100 mg, about 120 mg, about 150 mg, or any ranges between the recited values such as about 15-30 mg, about 30-60 mg, about 60-120 mg, about 75-150 mg, etc.) of ketamine/day, e.g., for about 24 hours to about 48 hours, such as about 24 hours or about 48 hours. In some embodiments, the method comprises applying the one or more monolithic patches to achieve any one or more of the PK profile described herein in any combination, such as a $C_{max}$ of ketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml and/or a $C_{max}$ of hydroxynorketamine of about 5-50 ng/mL (e.g., about 5 ng/ml, about 10 ng/ml, about 15 ng/ml, about 20 ng/ml, about 30 ng/ml, about 40 ng/ml, about 50 ng/ml, or any range between the recited values, such as about 10-50 ng/ml, about 20-50 ng/ml, about 20-30 ng/ml, etc.) such as about 10-30 ng/ml.

The dosing amount and dosing regimen include any of those described herein in any combination, e.g., those described in [85]-[92] of the Brief Summary. For example, in some preferred embodiments, the method comprises administering the one or more monolithic patches to the subject at a dosing frequency ranging from once a day to once a week, preferably, 1-3 times every week, more preferably, once in at least 3 days, such as once a week or twice a week. In some embodiments, there is a gap period between two consecutive ketamine doses. In some embodiments, one or more placebo transdermal delivery devices can be applied to the subject during the gap period as described herein. In some embodiments, there is no gap period between two consecutive ketamine doses. The one or more monolithic patches are typically applied to the subject for a duration of about 24 hours (i.e., the patch-on period is about 24 hours to deliver the desired dose of ketamine, although a longer duration such as two days or shorter duration such as about 8-16 hours can also be used in some cases. Typically, during the patch-on period, the one or more monolithic patches deliver ketamine to the subject at a substantially constant rate, for example, at a rate ranging from about 0.1 mg/cm$^2$/day to about 1 mg/cm$^2$/day, such as about 0.1 mg/day/cm$^2$, about 0.2 mg/day/cm$^2$, about 0.3 mg/day/cm$^2$, about 0.4 mg/day/cm$^2$, about 0.5 mg/day/cm$^2$, or about 1 mg/day/cm$^2$ of ketamine. The subject is not particularly limited and includes any of those described herein having a depression, typically recurrent or chronic depression. For example, in some embodiments, the subject is characterized as having a MDD. In some embodiments, the subject is characterized as having a MADRS≥20. In some embodiments, the subject is characterized as having failed at least one antidepressant treatment based on the MGH ATRQ. In some embodiments, the subject is characterized as having sub-optimal response to at least one antidepressant treatment. For example, the subject has <50% response to at least one antidepressant treatment (≥8 weeks at an adequate and stable dose for at least 4 weeks) per the MGH ATRQ. In some embodiments, the subject has recurrent major depressive disorder. In some embodiments, the subject has chronic major depressive disorder. In some embodiments, the subject is characterized as having treatment resistant depression. In some embodiments, the subject is in remission, for example, from the bolus ketamine treatment and/or additional antidepressant treatments. In some embodiments, the method further comprises administering to the subject one or more additional antidepressant treatments during the maintenance treatment period, such as oral antidepressants or another ketamine related antidepressant such as intranasal ketamine treatment.

In some specific embodiments, the present disclosure provides a method of treating a subject, who meets the DSM-5 criteria for MDD based on the Structured Clinical Interview for DSM-5 (SCID-5), the method comprising administering to the subject a transdermal delivery device herein (e.g., such as those described in [1]-[18], [23], or [83] of the Brief Summary, or any of the monolithic patches described herein). In some embodiments, the subject failed >1 and <8 trials in the current episode per the MGH ATRQ and/or has sub-optimal response defined as <50% response to current antidepressant treatment (≥8 weeks at an adequate and stable dose for at least 4 weeks) per the MGH ATRQ. In some embodiments, the transdermal delivery device is applied to the subject for a duration of about 24 hours. In some embodiments, the subject is administered a dose of ketamine of about 15 mg to about 100 mg per day, such as about 20 mg, about 40 mg, about 50 mg, about 60 mg, about 80 mg, or about 100 mg, which can be supplied by one or more monolithic patches herein, e.g., those having a patch size of about 20 cm$^2$-about 90 cm$^2$.

In some embodiments, the subject is treated chronically with the transdermal delivery device. The transdermal delivery devices are typically applied to the subject once or twice a week, with the duration of each application about 24 hours, or in some cases can be up to 48 or 72 hours. In some embodiments, the subject can be administered placebo transdermal delivery device (e.g., described herein) in between the transdermal delivery device comprising ketamine. Using a once a week dosing regimen as an example, the subject can be treated with a first ketamine transdermal patch for 24 hours on day 1, after which, the first ketamine transdermal patch is removed, which is followed by no treatment until a week later, on day 8, either a substantially the same ketamine transdermal patch or a substantially the same placebo patch (except without the ketamine) is applied to the patient for 24 hours, and so on. In some embodiments, the subject can be administered a ketamine transdermal patch, followed by no treatment (no ketamine or placebo patch) for a period ranging from 1 week to 6 weeks, before administering the next treatment, which can also be either a substantially the same ketamine transdermal patch or a substantially the same placebo patch (except without the ketamine), although in such dosing regimen, it is preferred not to use placebo patches after the no treatment period. In some embodiments, the transdermal delivery devices comprising ketamine are applied to the subject once or twice a week, with the duration of each application about 24 hours. In such embodiments, during the period of no ketamine treatment (i.e., no ketamine transdermal delivery), the subject can be treated with substantially the same placebo patches (except without the ketamine), with each application also about 24 hours, thus the overall application is once a day.

While many of the specific embodiments described herein are directed to methods of treating depression, the present disclosure is not so limited. For example, in some embodiments, the present disclosure also provides a method of treating pain in a subject in need thereof, such as neuropathic pain, complex regional pain syndrome (CRPS), chronic pain, etc. In some embodiments, the method comprises administering to the subject a transdermal delivery device comprising ketamine (such as those described in [1]-[18], [23], or [83] of the Brief Summary, or any of the monolithic patches described herein) to transdermally deliver a sufficient amount of ketamine to the subject having pain to achieve a $C_{max}$ of ketamine of about 5-50 ng/mL such as about 20-30 ng/ml and/or a $C_{max}$ of hydroxynorketamine of about 5-50 ng/mL such as about 20-30 ng/ml. In some embodiments, the method comprises administering to the subject a transdermal delivery device described herein (such as those described in [1]-[18], [23], or [83] of the Brief Summary, or any of the monolithic patches described herein) to deliver a therapeutically effective dose of ketamine to the subject. In some embodiments, the therapeutically effective dose of ketamine is a dose of about 15 mg to about 150 mg, which is delivered to the subject over about 24 hours (or 15-150 mg/24 hours), for example, by administration or application of the transdermal delivery device comprising ketamine herein to the subject for a duration of about 24 hours. In some embodiments, the dose of ketamine can be about 40 mg to about 250 mg, which can be delivered over about 1-3 days. In some embodiments, the dose of ketamine can be about 15 mg to about 60 mg, which can be delivered over about 8 hours to 16 hours. The ketamine dose can be administered at a frequency ranging from once a day to once a week, preferably, 1-3 times every week, more preferably, once in at least 3 days, such as once a week or twice a week.

In some embodiments, the present disclosure also provides a method of treating psychosis, e.g., psychosis associated with Parkinson's disease, Alzheimer's disease, various dementia such as vascular dementia etc. In some embodiments, the method comprises transdermally deliver a therapeutically effective amount of ketamine to a subject in need thereof. In some embodiments, the method comprises applying a transdermal delivery device described herein (such as those described in [1]-[18], [23], or [83] of the Brief Summary, or any of the monolithic patches described herein) the subject.

In some embodiments, the present disclosure also provides a method of treating any one or more of the Ketamine Clinical Conditions in a subject in need thereof. In some embodiments, the method comprises transdermally deliver a therapeutically effective amount of ketamine to a subject in need thereof. In some embodiments, the method comprises applying a transdermal delivery device described herein (such as those described in [1]-[18], [23], or [83] of the Brief Summary, or any of the monolithic patches described herein) the subject.

Kits

In some embodiments, the present disclosure also provides a kit comprising one or more transdermal delivery devices herein. In some embodiments, the kit comprises:
 (a) one or more transdermal delivery devices, such as substantially the same transdermal delivery devices, comprising ketamine; and optionally
 (b) one or more substantially the same placebo transdermal delivery device.

In some embodiments, the one or more transdermal delivery devices comprising ketamine are substantially the same transdermal delivery device, which can be any of those described herein, e.g., those described in [1]-[18], [23], or [83] of the Brief Summary, or any of the monolithic patches described herein. In some embodiments, each of the placebo transdermal delivery devices is substantially the same as each of the transdermal delivery devices comprising ketamine, except that the placebo transdermal delivery device does not contain ketamine. In some embodiments, the kit can be especially useful for treating a subject in need thereof for a treatment period of one month or more, wherein the kit includes four or more transdermal delivery devices, wherein each transdermal delivery device is independently the transdermal delivery device comprising ketamine or placebo transdermal delivery device, wherein each transdermal delivery device is labeled or organized according to its sequence of administration during the treatment period, typically, the first administration is an administration of the transdermal delivery device comprising ketamine. In some embodiments, the second administration is an administration of the placebo transdermal delivery device. In some embodiments, the sequence of administration during the treatment period comprises one or two administrations of the placebo transdermal delivery devices after every one or two administrations of the transdermal delivery device comprising ketamine. Other suitable dosing sequences include any of those described herein.

In some embodiments, the kit can comprise one or more transdermal delivery devices, such as substantially the same transdermal delivery devices, comprising ketamine; and one or more substantially the same placebo transdermal delivery devices. In some embodiments, each transdermal delivery device comprising ketamine can be used to deliver a therapeutically effective amount ketamine to a subject (e.g., for treating depression), and the dosing schedule includes a gap period when no ketamine is transdermally delivered to the subject. In some embodiments, during the gap period, one or more substantially the same placebo transdermal delivery devices are applied to the subject. In some embodiments, the kit arranges the transdermal delivery devices comprising ketamine and the substantially the same placebo transdermal delivery devices according to the dosing schedule. For example, for a once a week dosing frequency, the $1^{st}$ patch can contain ketamine, applied for about 24 hours, which is followed by 6 placebo patches, each applied for about 24 hours, and then another ketamine patch, and so forth. Other suitable dosing sequences include any of those described herein.

In some embodiments, a kit comprising two or more different sized monolithic patches comprising ketamine as described herein is provided. For example, in some embodiments, for each dosing, the treatment methods use two different sized monolithic ketamine patches to deliver a therapeutically effective amount of ketamine. In some embodiments, the kit can include the two different sized monolithic patches as a unit, such that the user can readily identify that the whole unit is to be used for each dosing. In some embodiments, the kit can include multiple such units. In some embodiments, the kit can also include placebo transdermal delivery devices, which can be convenient for certain treatment regimen described herein.

Ketamine Analogs and Metabolites

Ketamine can be extensively metabolized with the major metabolites being norketamine and hydroxyketamines, dehydronorketamine, and hydroxynorketamines. See e.g., Zanos, P. et al., "NMDAR inhibition—independent antidepressant actions of ketamine metabolites," *Nature,* 533 (7604):481-6(2016), and U.S. Pat. No. 9,650,352. Further, deuterated ketamines (e.g., with at least one of the hydrogen atoms in ketamine being substituted by deuterium above its natural abundance, e.g., greater than 10% deuterium, or more than 90% deuterium) and deuterated norketamines (e.g., with at least one of the hydrogen atoms in norketamine being substituted by deuterium above its natural abundance, e.g., greater than 10% deuterium, or more than 90% deuterium) have been synthesized. See e.g., WO 2017/180589, US Pub. No. 2017/0355663, and U.S. Pat. No. 7,638,651.

In some embodiments, the present disclosure also provides a ketamine metabolite transdermal delivery device comprising one or more metabolites chosen from norketamine, hydroxyketamines, dehydronorketamine, and hydroxynorketamines. In some embodiments, the ketamine metabolite transdermal delivery device can be essentially the same as any of the respective ketamine transdermal delivery device described herein, except that the ketamine is substituted in part or in whole with one or more metabolites chosen from norketamine, hydroxyketamines, dehydronorketamine, and hydroxynorketamines. For example, in some embodiments, the ketamine metabolite transdermal delivery device can be a drug-in-adhesive patch. In some embodiments, the active ingredient in the ketamine metabolite transdermal delivery device comprises, consists essentially of, or consists of hydroxynorketamine ("HNK"). In some embodiments, the HNK can be in the form of 2R,6R-isomer, 2S,6S-isomer, or any mixtures thereof. In some embodiments, the ketamine metabolite transdermal delivery device comprises a therapeutically effective amount of 2R,6R-hydroxynorketamine and is substantially free of 2S,6S-hydroxynorketamine (e.g., the ratio of the 2R,6R-isomer to the 2S,6S-isomer is more than 10:1, more than 20:1, or above). In some embodiments, the ketamine metabolite transdermal delivery device can also be used for the treatment of any of the diseases or disorders described herein, for example, depression (e.g., major depressive disorder, treatment-resistant depression, bipolar depression), anxiety, pain (e.g., neuropathic pain, complex regional pain syndrome (CRPS), chronic pain), psychosis, e.g., psychosis associated with Parkinson's disease, Alzheimer's disease, various dementia such as vascular dementia etc. In some embodiments, the ketamine metabolite transdermal delivery device can also be used for the treatment of any one or more of the Ketamine Clinical Conditions.

In some embodiments, the present disclosure also provides a deuterated ketamine transdermal delivery device comprising one or more of the deuterated analogs chosen from deuterated ketamines and deuterated norketamines. In some embodiments, the deuterated ketamine transdermal delivery device is essentially the same as any of the respective ketamine transdermal delivery device described herein, except that the ketamine is substituted in part or in whole with one or more of the deuterated analogs chosen from deuterated ketamines and deuterated norketamines. For example, in some embodiments, the deuterated ketamine transdermal delivery device can be a drug-in-adhesive patch. In some embodiments, the active ingredient in the deuterated ketamine transdermal delivery device comprises, consists essentially of, or consists of a deuterated ketamine. In some embodiments, the deuterated ketamine transdermal delivery device can also be used for the treatment of any of the diseases or disorders described herein, for example, depression (e.g., major depressive disorder, treatment-resistant depression, bipolar depression), anxiety, pain (e.g., neuropathic pain, complex regional pain syndrome (CRPS), chronic pain), psychosis, e.g., psychosis associated with Parkinson's disease, Alzheimer's disease, various dementia such as vascular dementia etc. In some embodiments, the deuterated ketamine transdermal delivery device can also be used for the treatment of any one or more of the Ketamine Clinical Conditions.

Definitions

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the term "cumulative drug permeated" refers to the total amount of drug permeated per square centimeter during a given period of time. Unless otherwise obvious from context, "cumulative drug permeated" at a given time (e.g., at 24 hours post administration) refers to the total amount of drug permeated per square centimeter from time 0 (i.e., time of administration) to the given time. Unless otherwise obvious from context, "cumulative drug permeated" refers to the arithmetic mean value measured and/or calculated according to the methods described herein. The term "mean value" as used herein, when not specified, also refers to arithmetic mean value, unless contradictory to common practice in the field.

As used herein, the term "flux" refers to the quantity of the drug permeated skin per unit area per unit time. As used herein, the term "average flux" refers to the total amount of drug permeated per square centimeter during a given period of time divided by the time duration. For example, an average flux from 12 hours to 24 hours post application would be calculated based on the total amount of drug permeated per square centimeter from 12 hours to 24 hours post application divided by 12 hours. As used herein, the term "steady state flux" refers to the flux observed during a period of time where the flux is substantially constant across the period (e.g., fluctuate within ±50% of the mean value observed for that period). Unless otherwise obvious from context, "flux", "average flux", or "steady state flux" refers to the arithmetic mean value measured and/or calculated according to the methods described herein. A typical unit of flux is milligram per square centimeter per hour.

Flux rate as referenced in this patent application can mean that measured by either in vivo or in vitro methods. One way to measure flux is to place the transdermal delivery device or formulation on a known skin area of a human volunteer and measure how much drug can permeate across skin within certain time constraints. In some embodiments, when specifically referenced as measured by in vitro method using human cadaver skin, the flux rate is measured in accordance with the method described in Example 2A. Although an in vitro method uses human epidermal membrane obtained from a cadaver, rather than measure drug flux across the skin using human volunteers, it is generally accepted by those skilled in the art that results from a properly designed and executed in vitro test can be used to estimate or predict the results of an in vivo test with reasonable reliability.

As used herein, the term "ketamine" refers to the base form, i.e., ketamine base, although it should be apparent to those skilled in the art that upon mixing with other ingredient(s), ketamine can become protonated. To be clear, in embodiments herein, the transdermal delivery device or the ketamine adhesive composition comprising ketamine in a recited amount should be understood such that the total amount of ketamine, regardless of its protonation state, is present in the recited amount when expressed as the equivalent amount of ketamine base. For example, in any of the embodiments described herein, the transdermal delivery device or the ketamine adhesive composition comprising ketamine in a recited amount can be prepared by a method comprising mixing directly or indirectly ketamine base in the recited amount with other ingredients/components, see e.g., Example 1A. Further, ketamine concentration, flux, and the alike as referenced herein should be understood as those measured and/or calculated in accordance with the methods described herein, with the final numeric value expressed as the equivalent value for ketamine base. For example, a ketamine flux of 1 mg/day/cm$^2$ should be understood as the total amount of ketamine permeated per day per cm$^2$, regardless of its protonation state, measured and/or calculated to be 1 mg when expressed as the equivalent value of ketamine base.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated.

The term "therapeutically effective amount," as used herein, refers to that amount of a therapeutic agent (e.g., ketamine) sufficient to result in amelioration of one or more symptoms of a disorder or condition (e.g., pain, depression), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment.

EXAMPLES

Example 1A. Ketamine Patch Preparation

This example describes an exemplary procedure for preparation of a ketamine patch formulation and transdermal delivery device. The drug substance (active ingredient) is directly loaded into the pressure sensitive adhesive (PSA) polymer matrix. The monolithic DIA design configuration is shown in FIG. 1. In this configuration, the adhesive matrix provides several functions, including skin adhesion, storage of the drug, and control over drug/enhancer delivery rate, and it also governs their partitioning into the stratum corneum. As shown in FIG. 1, the DIA matrix (2) is supported on the topside by an impermeable backing film (1) and on the side that faces the skin, it is laminated with a removable release liner (3). Patch backing film (1): Scotchpak 9723 (3M Drug Delivery Systems), pigmented polyethylene and polyester laminated film, 1.7 mil. Protective release liner (3): Loparex. The adhesive matrix (2) thickness is about 3.2 mils. Ketamine transdermal drug delivery system (patch) is packed in a unit dose pouches constructed of Multi-layered Polyester/Polyethylene/Aluminum foil laminated pouch.

The ingredients of the ketamine patch formulation (used for the adhesive matrix) of this example are shown in Table A below:

TABLE A

| Ingredient Function | Ingredient | Dry Weight % |
| --- | --- | --- |
| Active Ingredient | Ketamine Free Base | 15.7% |
| Pressure Sensitive Adhesive | Duro Tak 87-2677 | 51.2% |
| Skin permeation enhancer | Oleyl Oleate | 5.7% |

TABLE A-continued

| Ingredient Function | Ingredient | Dry Weight % |
| --- | --- | --- |
| Skin permeation enhancer | Levulinic acid | 5.2% |
| Anti-Oxidant | Butylated hydroxytoluene | 0.5% |
| Crystallization inhibitor | Polyvinyl pyrrolidone-co-vinyl acetate (Kollidon VA 64) | 21.7% |
| Total | | 100% |

The manufacture of ketamine transdermal patch is based on the principle of solution-casting method for fabricating thin adhesive matrix films, follows by drying of wet casting, and finally, lamination of the dried adhesives to support release liner film. The overall solvent-casting fabrication process is described below: 1) prepare wet casting solution: Mix and dissolve the active ingredient with the adhesive polymers, skin permeation enhancers, crystallization inhibitors, and other ingredients in an organic solvent (e.g. ethyl acetate) to form a homogenous casting solution; 2) Cast wet film: Uniformly coat (cast) the homogenous coating solution onto a backing film with predetermined thickness (e.g. 15 mils, wet film thickness) with a casting apparatus or machine; 3) Dry film: Dry the cast coating in air at room temperature for 16-24 hrs. (The coating can also be dried by air dry for 10 min, and then dry it in a forced-air oven at 85° C. for 10 min.) 4) Laminate to release liner film: Laminate the dried adhesives to polyester release liner film to produce a 3-layered patch construction. 5) Die-cut the film: Die-cut the dried film into desired shape and sizes (e.g., 20 cm$^2$ or 60 cm$^2$ square) of dosage units (individual unit-dose squares). 6) Pouch finished films: Pouch the unit dosage films by sealing the pre-cut pouching stock material. The final patches are individually packaged in single pouches as single unit doses.

Example 1B. Placebo Patch Preparation

This example describes an exemplary procedure for preparation of a placebo patch formulation and transdermal delivery device. The configuration of the placebo patch is the same as that of the ketamine patch shown in Example 1A, except that the adhesive matrix layer does not include any active ingredient ketamine. The same container closure system was used to package the placebo product. Same preparation as described above for the ketamine patches (Example 1A) except there is no Ketamine to be added to the batch.

The ingredients of the placebo patch formulation of this example are shown in Table B below:

TABLE B

| Ingredient Function | Ingredient | Dry Weight % |
| --- | --- | --- |
| Active Ingredient | Ketamine Free Base | 0% |
| Pressure Sensitive Adhesive | Duro Tak 87-2677 | 60.8% |
| Skin permeation enhancer | Oleyl Oleate | 6.7% |
| Skin permeation enhancer | Levulinic acid | 6.2% |
| Anti-Oxidant | Butylated hydroxytoluene | 0.6% |

TABLE B-continued

| Ingredient Function | Ingredient | Dry Weight % |
| --- | --- | --- |
| Crystallization inhibitor | Polyvinyl pyrrolidone-co-vinyl acetate (Kollidon VA 64) | 25.7% |
| Total | | 100% |

Example 2A. Ketamine Patch Permeability Evaluation

The in vitro permeability of two ketamine formulations was evaluated in human cadaver skin in a Franz Cell model.

The tested formulations DIA-2E prepared according to Example 1A has a formulation shown in Table A of Example 1A. DIA-3E have the following ingredients by weight: ketamine free base (about 15.6%), DMSO (about 5.1%), Oleyl Oleate (about 5%), Levulinic acid (about 4.9%), Kollidon VA 64 (about 20.3%), and Duro Tak 87-2677 (about 49.1%).

The permeation equipment used was FDC-6 Franz Cell System, manufactured by Logan Instruments, Somerset, N.J. Human cadaver skin (white, male, section, left posterior leg) was dermatomed and supplied by New York firefighters Skin Bank, N.Y.

Samples were cut into circular discs with 1 inch in diameter. Dose area is 1.767 cm$^2$. Medium for the permeation study was phosphate buffer solution (pH 7.4, 10 PBS tablets manufactured from MP Biomedicals LLC in 1 L deionized water). Other operational parameters were: for each formulation, four patches (circle with 1 inch in diameter) applied to surface of the human cadaver skin as donor, receptor volume=12 mL, medium temperature=37° C., stirring speed=120 rpm (revolutions per min). Samples were collected at 2 h, 4 h, 8 h, 24 h, and 48 h. Sample method: At time point of 2 h and 4 h, withdraw 0.3 ml medium from the receptors for HPLC analysis, and replace the aliquots withdrawn for analysis with equal volumes of fresh medium. At time point of 8 h, 24 h and 48 h, withdraw 1 ml of receptor medium as the samples, then suction all the medium out of receptor, replace with 12 ml of fresh medium.

Drug assay of receptor media was determined by Agilent HPLC/UV system equipped with ChemStation. A Phenomenex Gemini-C18 column (150*4.6 mm, 5 μm) was used. An isocratic elution method with mobile phase of a mixture of PBS buffer solution (2.72 g/L KH$_2$PO4, 50 μL of 1N NaOH solution) and acetonitrile (84:16) was used. Measure wavelength was set at 210 nm.

The permeation (mg/cm$^2$), along with standard deviation and relative standard deviation (RSD), for the three formulations tested at the preselected sampling times are given in the following Table 1A.

TABLE 1A

The in vitro cumulative permeability of DIA-3E (117-171225A) and DIA-2E (117-180101) with Human skin in Franz Cell Model. (N = 4)

| | Batch No. | | | | | |
| --- | --- | --- | --- | --- | --- | --- |
| | 117-171225A (DIA-3E) | | | 117-180101 (DIA-2E) | | |
| Time, hr | Cum. mean. mg/cm$^2$ | SD, mg/cm2 | RSD % | Cum. mean, mg/cm$^2$ | SD, mg/cm$^2$ | RSD% |
| 2 | 0.00171 | 0.00050 | 29.3 | 0.00516 | 0.00437 | 84.7 |
| 4 | 0.0247 | 0.0079 | 32.0 | 0.0398 | 0.0268 | 67.5 |
| 8 | 0.075 | 0.013 | 17.5 | 0.102 | 0.052 | 50.9 |
| 24 | 0.245 | 0.043 | 17.7 | 0.286 | 0.073 | 25.6 |
| 48 | 0.656 | 0.112 | 17.1 | 0.713 | 0.123 | 17.2 |

Example 2B. Ketamine Patch Permeability Evaluation

The in vitro permeability of two ketamine patches prepared according to Example 1A, 20 cm$^2$ (total ketamine base 24.7 mg) and 60 cm$^2$ (total ketamine base 87.3 mg), was evaluated in human cadaver skin in a Franz Cell model, following the procedures shown in Example 2A.

In vitro permeability from the skin of two human donors (each was repeated 12 times) was obtained. The mean data were used to estimate the in vitro permeation rates at the steady state, and used for in vivo PK predictions in humans. Several publications on ketamine human IV PK were obtained by searching the PubMed and re-analyzed to determine the appropriate PK data to use for prediction of human PK. The in vivo PK was calculated by the convolution method based on in vitro permeability and IV PK (Phoenix version 64 (Pharsight™, Certara L.P.). The input function was set as the derivative of linear spline function of cumulative input.

Figure 2:
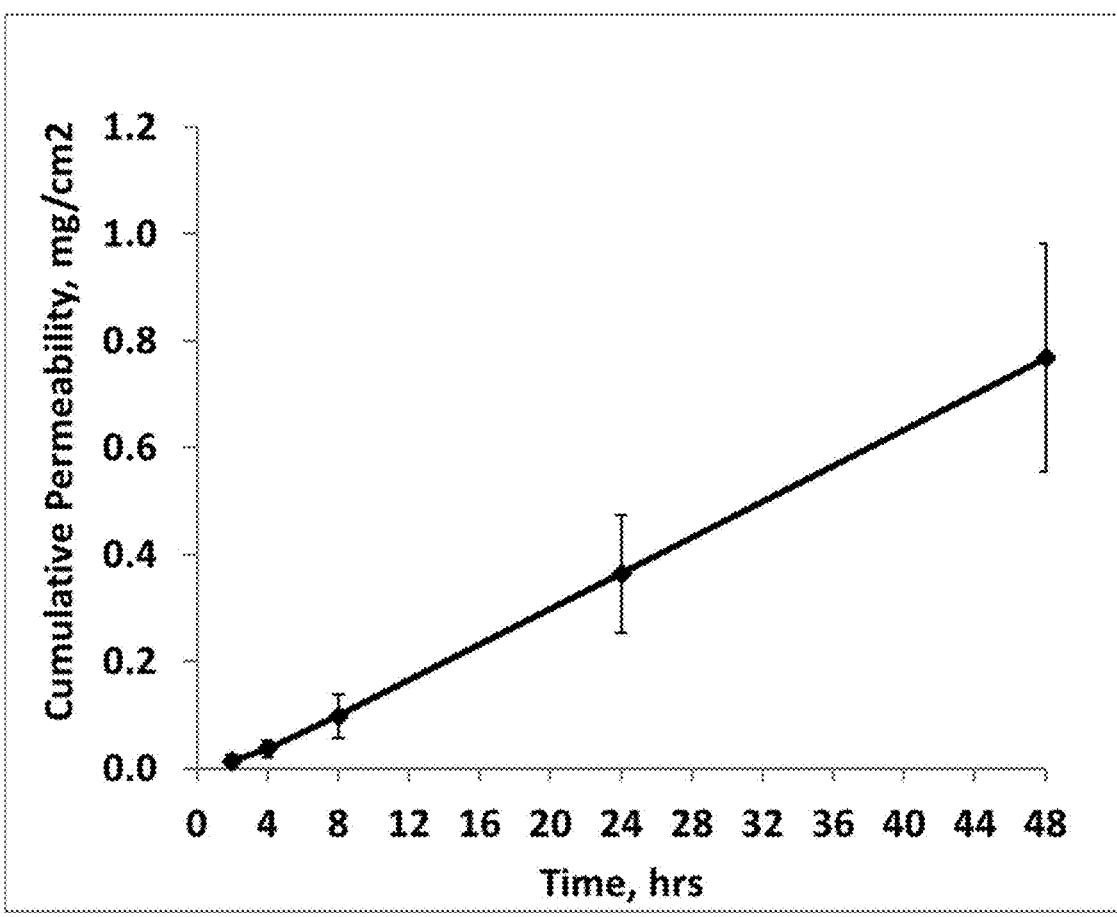
FIG. 2 presents a graph showing the in vitro mean permeability of ketamine from ketamine patches (formulation details shown in Table A of Example 1A) in Franz cell model using human cadaver skin.

These data demonstrate that the two patches delivered ketamine at about 0.33 and 1.00 mg/hour, respectively, based on the linear absorption range between 4 and 48 hours, see Table 1B below and FIG. 2.

TABLE 1B

In vitro cumulative permeability of ketamine from ketamine patches using human cadaver skin in Franz Cell Model

| | Batches | | | | | | | | |
|---|---|---|---|---|---|---|---|---|---|
| | BNX180802, 20 cm2 (N = 12) | | | BNX180902, 60 cm2 (N = 12) | | | Averaged Value (Based on two batches, N = 24) | | |
| Time, h | Cum. mean, mg/cm$^2$ | SD, mg/cm$^2$ | CV % | Cum. mean, mg/cm$^2$ | SD, mg/cm$^2$ | CV % | Cum. mean, mg/cm$^2$ | SD, mg/cm$^2$ | CV % |
| 2 | 0.0132 | 0.0056 | 42.0% | 0.0108 | 0.0069 | 64.3 | 0.0140 | 0.0104 | 74.4 |
| 4 | 0.0393 | 0.0127 | 32.3% | 0.0330 | 0.0178 | 54.0 | 0.0362 | 0.0155 | 42.8 |
| 8 | 0.111 | 0.029 | 26.0% | 0.0945 | 0.0464 | 49.1 | 0.0974 | 0.0416 | 42.7 |
| 24 | 0.364 | 0.081 | 22.2% | 0.362 | 0.139 | 38.3 | 0.363 | 0.111 | 30.5 |
| 48 | 0.724 | 0.152 | 21.0% | 0.811 | 0.260 | 32.0 | 0.768 | 0.213 | 27.7 |

The in vitro permeability data showed a slow-rising phase in absorption in about 2-4 hours, presumably due to retention of the drug in the skin tissue, followed by an approximate linear increase in the cumulative amount from 4 to 48 hours. The estimated in vitro permeation rate at the steady state between 4 and 48 hours was about 0.0167 mg/hr/cm$^2$, i.e., 0.33 mg/hr for the 20 cm$^2$ patch and 1.00 mg/hr for the 60 cm$^2$ patch.

Example 2C. Ketamine Dissolution Studies

The drug release test of ketamine patch prepared according to Example 1A was conducted using dissolution equipment Logan DISSO III-7 (USP 3 and 7 Dissolution Apparatus in one unit). Program was set to run the test as USP 7 Apparatus. The drug release of Ketamine patch reached above 85% within 24 hours, meeting the criterion of more than 85% drug release at time point 72 hours.

Medium for the release study was phosphate buffer solution (pH 7.4, prepared from 10 PBS tablets, manufactured from MP Biomedicals LLC in 1 L water). Other operational parameters were: eight patches (circles with 0.5 inch in diameter) adhered to the disk on the sample holder, medium volume=20 mL, medium temperature=37° C., reciprocal speed=20 dpm (dip per min), and drip time=3 s, hold time= 3 s, stoke=2 cm, clearance=10.0 mm, drip position=217.1 mm. Sampling times were 1, 2, 4, 8, 24, 48 and 72 h. Sample volume=2 mL, prime volume=8 mL, purge=10.0 mL. Analytical methods are as shown in Example 2A.

The drug release (%), along with standard deviation and relative standard deviation (RSD), for the batch tested at the pre-selected sampling times are given in the following table. The released drug (%), averaged values, along with standard deviation and % RSD, for the formulation tested at the pre-selected sampling are given in the following table.

TABLE 1C

The released drug percent of Ketamine Patch using Dissolution USP 7 Apparatus.

| Batch No. | 117-180420 (N = 8) | | |
|---|---|---|---|
| Time, h | Drug release, mean, % | SD | RSD % |
| 1 | 42.69% | 2.86% | 6.690% |
| 2 | 62.11% | 3.13% | 5.035% |
| 4 | 77.56% | 2.53% | 3.258% |
| 8 | 87.55% | 1.74% | 1.989% |
| 24 | 92.73% | 1.16% | 1.256% |
| 48 | 93.77% | 1.05% | 1.124% |
| 48 | 94.01% | 1.05% | 1.118% |

Example 3A. Ketamine Patch Stability Studies

In this test, it was found that DIA-2E was storage stable when stored at room temperature (25±2° C.) at 60% relative humidity (RH)±5% RH or at 40±2° C. at 75% relative humidity (RH)±5% RH, no ketamine particles or crystals were found at 1 month, 3 months, or 6 months. In contrast, DIA-3E, while storage stable when stored at room temperature (25±2° C.) at 60% relative humidity (RH)±5% RH, with no ketamine particles or crystals were at 1 month, 3 months, or 6 months. When stored at 40±2° C. at 75% relative humidity (RH)±5% RH, ketamine particles or crystals were found in DIA-3E at 6 months.

A batch of 20 cm² patches (in vitro release rate of about 8 mg/24 hour) were tested for stability at 25° C./60% RH. It was found that these patches are stable under the tested conditions for more than 24 months. Formulation details including preparations of the patches are shown in Example 1A (Table A), each patch includes about 24.7 mg of ketamine base. The results up to 24 months were shown in Table 1D below:

TABLE 1D

Stability Test for 20 cm² patches at 25° C./60% RH

| Test | Acceptance Criteria | Time (Months) | | | | | | |
|---|---|---|---|---|---|---|---|---|
| | | 0 | 3 | 6 | 9 | 12 | 18 | 24 |
| Patch Appearance | 1. Clear adhesive coating sandwiched between a split transparent stiff liner and a beige-colored pliant backing film; 2. Adhesive matrix is free of crystals or particles. | Conforms | Conforms | Conforms | Conforms | Conforms | Conforms | Conforms |
| Weight of adhesive matrix | Report averaged weight of 6 patches | 163 mg | 178 mg | 171 mg | 182 mg | 180 mg | 181 mg | 177 mg |
| Peel Adhesion (off HDPE Panel) | Report result | 408 g/in | 375 g/in | 435 g/in | 236 g/in | 217 g/in | 290 g/in | 313 g/in |
| Cold Flow | 1. The patch can be easily removed from the pouch; 2. After removal of the release liner, minimal adhesive remains on the release liner and minimal adhesive stringing is observed at the perimeter of the patch. | Conforms | Conforms | Conforms | Conforms | Conforms | Conforms | Conforms |
| Assay of Ketamine by HPLC | 90-110% of label claim | 92.5% | 96.9% | 98.2% | 98.7% | 97.9% | 98.5% | 98.9% |
| Related Substances | Impurity A-NMT 0.1%; Unknown Impurity-NMT 0.3%; Total Impurity-NMT 1.0% | ND* | ND | ND | ND | ND | ND | ND |

*ND = not detectable.

A batch of 60 cm² patches (in vitro release rate of about 24 mg/24 hour) were tested for stability at 25° C./60% RH. It was found that these patches are stable under the tested conditions for more than 24 months. Formulation details including preparation of the patches are shown in Example 1A (Table A), each patch includes about 87.3 mg of ketamine base. The results were shown in Table 1E below:

TABLE 1E

Stability Test for 60 cm2 patches at 25° C./60% RH

| Test | Acceptance Criteria | Time (Months) | | | | | | |
|---|---|---|---|---|---|---|---|---|
| | | 0 | 3 | 6 | 9 | 12 | 18 | 24 |
| Patch Appearance | 1. Clear adhesive coating sandwiched between a split transparent stiff liner and a beige-colored pliant backing film; 2. Adhesive matrix is free of crystals or particles. | Conforms | Conforms | Conforms | Conforms | Conforms | Conforms | Conforms |

TABLE 1E-continued

Stability Test for 60 cm2 patches at 25° C./60% RH

| Test | Acceptance Criteria | Time (Months) | | | | | | |
|---|---|---|---|---|---|---|---|---|
| | | 0 | 3 | 6 | 9 | 12 | 18 | 24 |
| Weight of adhesive matrix | Report averaged weight of 6 patches | 532 mg | 551 mg | 529 mg | 519 mg | 520 mg | 522 mg | 519 mg |
| Peel Adhesion (off PDPE Panel) | Report result | 354 g/in | 352 g/in | 227 g/in | 271 g/in | 153 g/in | 213 g/in | 300 g/in |
| Cold Flow | 1. The patch can be easily removed from the pouch; 2. After removal of the release liner, minimal adhesive remains on the release liner and minimal adhesive stringing is observed at the perimeter of the patch. | Conforms | Conforms | Conforms | Conforms | Conforms | Conforms | Conforms |
| Assay of Ketamine by HPLC | 90-110% of label claim | 109.5% | 92.1% | 99.6% | 97.7% | 98.5% | 98.3% | 98.5% |
| Related Substances | Impurity A-NMT 0.1%; Unknown Impurity-NMT 0.3%; Total Impurity-NMT 1.0% | ND* | ND | ND | ND | ND | ND | ND |

*ND = not detectable.

Similar tests were done for the 20 and 60 cm² patches at 40° C./75% RH for at least 6 months. The results show that the 20 and 60 cm² patches are stable under the tested conditions for at least 6 months and meet the acceptance criteria shown in Table 1D or 1E.

The 20 and 60 cm² placebo patches (see Example 1B, Table B for ingredients) were also tested for stability and were found to be stable under either of the conditions: 25° C./60% RH (for at least 24 months) or 40° C./75% RH (for at least 6 months).

Example 3B. 30—Months Stability Studies

A batch of 20 cm² patches (in vitro release rate of about 8 mg/24 hour) were tested for stability after 30-months of their preparation. It was found that these patches are stable, with no observable drug crystals and have substantially the same in vitro ketamine permeation rate. Formulation details including preparations of the patches are shown in Example 1A (Table A), each patch includes about 24.7 mg of ketamine base.

The following tests were performed: Visual observation under polarized microscope; Assay of ketamine by HPLC; and Skin permeation study using human cadaver skin (see Example 2B).

From polarized microscopic imaging study: no apparent crystals were observed in 30-Mo ketamine patch sample, indicating that the drug product is stable physically for 30 months after manufacturing.

The HPLC analysis shows that ketamine is stable.

| Parameter | Specifications | Test Results |
|---|---|---|
| Assay of ketamine | 90-110% of label claim | 98% |
| Related Substances (Impurities) | NMT 0.1% | <0.05% |
| Weight of Adhesive Matrix | Report results | 176 mg |

The skin permeation study shows that the 30-Mo Ketamine Patch is as good as the data generated when the patches were initially prepared. This further verifies the observation we have on the 30-Month Patch's microscopic images, where no Crystals were found. The permeation data of the 30-month ketamine patches are shown in the table below (compare to earlier tests of the same batch shown in Table 1B):

| Two cells were used: Cumulative ketamine permeated, μg/cm2 | | | |
|---|---|---|---|
| Hours | Cell 1 | Cell 2 | average |
| 2 | 12.67 | 12.38 | 12.52 |
| 4 | 58.63 | 46.21 | 52.42 |
| 8 | 119.26 | 80.26 | 99.76 |
| 24 | 442.09 | 319.00 | 380.55 |
| 48 | 846.12 | 749.93 | 798.02 |

Example 4. Ketamine Patch Skin Irritation and Sensitization Studies

Skin Irritation Studies: A primary skin irritation test was conducted with rabbits to determine the potential for ketamine transdermal patch and placebo patch (see formulation in Examples 1A and 1B) to produce irritation after a single topical application. Under the conditions of this study, the test substance is classified as slightly irritating to the skin. One 1-inch×1-inch pieces of the test substance and placebo weighing approximately 0.13 grams, were applied to the skin of three healthy rabbits for 4 hours. Following exposure, dermal irritation was evaluated by the Draize method of scoring (Draize, Woodard, & Calvery, 1944). All animals appeared active and healthy and gained body weight during the study. Apart from the dermal irritation noted below, there were no other signs of gross toxicity, adverse clinical effects, or abnormal behavior.

Ketamine Transdermal Patch: Within 30-60 minutes of patch removal, all three treated sites exhibited well-defined erythema. The overall incidence and severity of irritation decreased gradually with time. All animals were free of dermal irritation by Day 7 (study termination).

Placebo Patch: Within 30-60 minutes of patch removal, all three treated sites exhibited very slight to well-defined erythema. The overall incidence and severity of irritation decreased with time. All animals were free of dermal irritation by 72 hours. The Primary Dermal Irritation Index (PDII) calculated for the active ketamine transdermal patch was 1.3, and for the placebo patch was 0.9.

Under the conditions of this study, both ketamine transdermal patch and placebo patch tested are classified as slightly irritating to the skin.

Sensitization Studies: A 20-22 mm circle, adhesive side down, of the test substance patch was topically applied to twenty healthy test guinea pigs, once each week, 6 hours per application for a three-week induction period. A group of ten guinea pigs received an application of the placebo patch in the same manner as the test substance patch (i.e., ketamine patch). Twenty-seven days after the first induction dose, a challenge dose of the test substance patch or the placebo patch was applied to a naive site on each guinea pig. A naive control group (ten animals) was maintained under the same environmental conditions and treated with the test substance and placebo patches at challenge only. Approximately 24 and 48 hours after each induction and challenge dose, the animals were scored for erythema.

Induction Phase: Test Animals (20-22 mm circles of test substance): Very faint erythema (0.5) was noted in a total of four animals at the test sites during the second and third inductions. Placebo Animals (20-22 mm circles of placebo): Very faint erythema (0.5) was noted in a total of three animals at the placebo sites during the second induction only.

Challenge Phase: Test Animals (20-22 mm circles of test substance): There was no dermal irritation noted at any test site following the challenge application. Placebo Animals (20-22 mm circles of placebo): There was no dermal irritation noted at any placebo site following the challenge application.

Naive Control Animals (20-22 mm circles of test substance): There was no dermal irritation noted at any naive control site following the challenge application. Naive Control Animals (20-22 mm circles of placebo): There was no dermal irritation noted at any naive control site following the challenge application.

CONCLUSION: Based on these findings, both ketamine transdermal patch and placebo patch tested are not considered to be a contact sensitizer in the Buehler sensitization assay.

Example 5. Pharmacokinetic and Pharmacodynamics Studies

This was a Phase 1, first-in-human, single-blind, multi-center, clinical study to evaluate the pharmacokinetics (PK), safety, and antidepressant effects of ketamine transdermal patch 20 mg (low-dose) and 40 mg (high-dose) in sub-optimally responsive subjects (defined as <50% response to current antidepressant treatment) diagnosed with major depressive disorder (MDD). The transdermal patch was designed to deliver during a 24 hour period low-dose ketamine, predicted to administer approximately 20 mg dose, placebo, and high-dose ketamine, predicted to administer approximately 40 mg dose, in three sequential stages. Patch residual drug measurements were conducted after each subject had completed the Stage 1 dosing (low-dose) and PK analyses were done to determine the size of patches and duration of application for each subject to ensure the dose delivered in Stage 3 would be close to 40 mg. Eighteen (18) subjects were included in this study.

In this study, adult subjects with MDD were enrolled and received a ketamine low-dose, placebo, and a ketamine high-dose patch in three study stages. This study aimed to determine the PK, antidepressant (pharmacodynamic [PD]), and safety effects of the ketamine transdermal patch in sub-optimally responsive subjects diagnosed with MDD.

Figure 3:
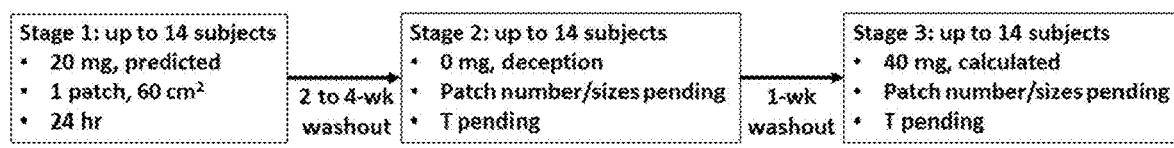
FIG. 3 shows an overall scheme of the clinical study dosing schedules herein.

Enrollment was planned to achieve participation of up to 14 adult subjects with MDD in the 3 stages of the protocol. Subjects were to be screened within 4 weeks of enrollment. Eligible subjects who provided written consent were to be enrolled into Stage 1 of the study. In Stage 1 of the study, subjects were to receive the low-dose transdermal patch. The amount of residual drug was to be measured and PK analysis conducted for each subject to inform the subsequent dosing. In Stage 2, after a 2 to 4 week washout period, a placebo patch was to be administered. A "deception" protocol was used in order to ensure the subjects remained blinded to the treatment. Placebo administration was followed by a 1 week washout period, after which subjects were to receive the high-dose transdermal patch in Stage 3. The overall study duration from screening until the end of Stage 3 was approximately 60 days, including both inpatient and outpatient portions of the study. The general study design is illustrated in FIG. 3.

Male or female subjects diagnosed with MDD who had a current depressive episode of at least 8 weeks were enrolled into this study. The following main inclusion criteria must have also been met:

Met the Diagnostic and Statistical Manual of Mental Disorders, Fifth Edition (DSM-5) criteria for MDD based on the Structured Clinical Interview for DSM-5 (SCID-5).

Presented a current depressive episode of at least 8 weeks.

Have a MADRS≥20 at screening and at baseline.

Have failed >1 and <8 trials in the current episode per the Massachusetts General Hospital Antidepressant Treatment Response Questionnaire (MGH ATRQ).

Have sub-optimal response defined as <50% response to current antidepressant treatment (≥8 weeks at an adequate and stable dose for at least 4 weeks) per the MGH ATRQ.

Is in general good health per Investigator discretion based on medical history, physical examination (PE), electrocardiogram (ECG), and routine laboratory tests (blood chemistry, hematology, urinalysis, and drug screen).

Have a body mass index (BMI) of 18-35 kg/m2 (inclusive) at screening.

Exclusion criteria include for example, a clinically significant abnormal ECG at the screening visit, treatment with any investigational drug, use of any known cytochrome P450 (CYP) 3A4 enzyme-inducing/inhibiting agents (e.g., barbiturates, phenothiazines, cimetidine, St. John's Wort), or herbal supplements within 7 days prior to the first dose of study medication, a known hypersensitivity to ketamine, a history of use of ketamine for MDD and did not respond to ketamine, or recent use of ketamine in any formulation for any indication within 4 weeks prior to screening.

Treatment Administered:

Stage 1: Subjects who consented to participate and met all inclusion/exclusion criteria were to receive a single application of ketamine transdermal patch (60 cm$^2$) in the morning on the upper arm for 24 hours. The patch was predicted to deliver systemically approximately 20 mg. Stage 2: Subjects who completed the Stage 1 procedures and who did not meet the stopping criteria and completed the 2 to 4 week washout period, were to receive a single application of ketamine transdermal patch placebo in the morning on the upper arm. The patch number/sizes (20 and 60 cm$^2$) and duration (T), if necessary and different from 24 hours, were determined after the PK profile of the 20 mg dose of ketamine transdermal patch was analyzed and modeled. Stage 3: Subjects who completed the Stage 2 study procedures and who did not meet the stopping criteria and completed the 1-week washout were to receive a single application of ketamine transdermal patch. The patch number/sizes (20 and 60 cm$^2$) and duration (T), if necessary and different from 24 hours, were determined after the PK profile of each subject in the 20 mg dose stage of ketamine transdermal patch was analyzed and modeled. The ketamine transdermal patch and placebo patch formulations have the ingredients shown in Tables A or B in Example 1A. For the ketamine patches, a 20 cm$^2$ patch includes total ketamine base about 24.7 mg and a 60 cm$^2$ patch includes total ketamine base 87.3 mg.

This was a single-blind study. All subjects received ketamine transdermal patches that delivered 20 mg (low dose), placebo, and 40 mg (high dose) racemic ketamine sequentially.

Whole venous blood samples of 3 mL were drawn from a peripheral vein in the opposite side of the patch at the specified times after administration of the ketamine transdermal patch. For Stage 1, blood samples were collected pre-patch application, and at 2, 6, 12, 24, 28, 32, 48, 96, and 168 hours post-patch application. For Stages 2 and 3, blood samples were collected pre-patch application, and at 2, 6, 12, 24 hours post-patch application (or duration of individualized treatment [T] as determined by 20 mg treatment PK data, to deliver exactly 40 mg of ketamine, if necessary), as well as T+4, T+8, T+12 (if needed based on the assessment of PK and safety results from the low-dose treatment), T+24, T+72, and T+144 hours post-patch application.

Blood samples were collected in tubes containing sodium heparin and stored on ice or room temperature until centrifuged under refrigeration or room temperature for at least 10 minutes at 3,000 revolutions per minute. After centrifugation, plasma was removed, divided into 2 aliquots of approximately 0.6 mL each, frozen, and stored at or below −20° C. Blood was processed to plasma and frozen within 1 hour of collection. Processed frozen plasma samples were transferred on dry ice to the analytical laboratory and were stored at or below −20° C. until bioanalysis was performed.

The PK parameters of ketamine, as well as ketamine principle metabolites, norketamine and hydroxynorketamine, were determined. A non-compartmental analysis (NCA) was used to calculate PK parameters using Phoenix® WinNonlin® 6.4 or later (Certara, USA). The PK parameters calculated are listed in Table 2A below.

TABLE 2A

Pharmacokinetic Parameters

| Parameter Name | Parameter Description |
|---|---|
| $C_{max}$ | Maximum observed plasma concentration |
| $T_{max}$ | Time to maximum observed plasma concentration |
| $t_{1/2}$ | Apparent terminal elimination half-life |
| $AUC_{0-t}$ | Area under the plasma concentration-time curve from time 0 to time t |
| $AUC_{0-\infty}$ | Extrapolated area under the plasma concentration-time curve from time 0 to infinity |
| $\lambda_z$ | Terminal phase rate constant |
| $AUC_{extr}$ | The proportion of $AUC_{0-\infty}$ due to extrapolation |

Safety data included adverse events (AEs), concomitant medications, PE, vital signs (VS), ECGs, clinical laboratory results, other safety measures based on questionnaires (Clinician-Administered Dissociative States Scale [CADSS], Observer's Assessment of Alertness/Sedation Scale [OAA/S], Brief Psychiatric Rating Scale [BPRS]), and the emergence of suicidality based on the suicidal ideation and suicidal behavior ratings of the Columbia-Suicide Severity Rating Scale (C-SSRS). Safety summaries and analyses were performed on the Safety Population and were presented by treatment. Observed data was summarized using counts and percentages for discrete variables and means, SD, median, inter-quartile range (25$^{th}$-75$^{th}$ percentile), minimum, and maximum for continuous measures.

PD endpoints included change from baseline in standardized clinician-rated outcome measures such as the MADRS, SDQ, the CGI-S, and the CGI-I, and also the proportion of subjects with 50% reduction in the MADRS. Depression assessment was conducted in person or by phone interview. In general, descriptive summary statistics for continuous variables included the number of subjects (N), mean, median, SD, quartiles, and minimum and maximum. Descriptive statistics for categorical variables included number and percentage of subjects in each category. Summary statistics were presented by treatment.

Summary of Results

Pharmacokinetics:

The actual calculated average dose of ketamine delivered at Stage 1 (low-dose) was 27.8 mg and the actual calculated average dose of ketamine delivered at Stage 3 (high-dose) was 51.3 mg (SD, 15.1 mg). The estimation for both doses was relatively close to the target dose. This residual drug analysis from the worn patched showed that the dose absorbed into body from a 60 cm$^2$ patch is about 28 mg in 24 hours.

TABLE 2B

Drug Residual Analysis of Patches Administered at Stage 1

| Stage | ID | Patches administered, cm$^2$ | Ketamine absorption estimated/ total, mg | Actual dosing duration, hr |
|---|---|---|---|---|
| 1 | Mean (SD) | 60 | 27.8 (7.5) | Range 24.0 to 24.3 |
| | CV % | — | 27 | — |

The PK profile of the tested ketamine transdermal patch showed a slow-rising and prolonged exposure, with an average $C_{max}$ of ketamine approximately 10.3 to 14.4 ng/mL at Stage 1 and Stage 3. The $C_{max}$ was about 15-20 fold lower than that reported from a typical 40 min intravenous (IV) infusion of 0.5 mg/kg of ketamine. Generally, AUC values followed the ascending order of ketamine, norketamine, and hydroxynorketamine. The mean AUC ratio of hydroxynorketamine over ketamine was about 1.40 to 1.54 at Stage 1 and Stage 3, respectively. See Table 2C below as well as FIGS. 4 and 5.

TABLE 2C

Pharmacokinetic parameters for Stages 1 and 3

| ID | | $AUC_{all}$ ng/mL·h | $AUC_{inf}$ ng/mL·h | Extrap % | $T_{max}$ h | $C_{max}$ ng/mL | $T_{1/2}$ h |
|---|---|---|---|---|---|---|---|
| | | | Ketamine | | | | |
| Stage 1 | N | 18 | 15 | 15 | 18 | 18 | 15 |
| | Median | 280 | 274 | 6 | 28.0 | 9.92 | 13.7 |
| | Mean | 284 | 299 | 6 | 27.1 | 10.3 | 13.2 |
| | SD | 135 | 140 | 4 | 3.8 | 5.1 | 4.4 |
| | CV % | 48 | 47 | 65 | 14 | 49 | 34 |
| Stage 3 | N | 12 | 11 | 11 | 12 | 12 | 11 |
| | Median | 339 | 362 | 3 | 28.0 | 9.67 | 14.9 |
| | Mean | 393 | 423 | 4 | 27.0 | 14.4 | 13.8 |
| | SD | 236 | 241 | 3 | 2.8 | 14.0 | 3.8 |
| | CV % | 60 | 57 | 78 | 10 | 97 | 28 |
| | | | Hydroxynorketamine | | | | |
| Stage 1 | N | 18 | 7 | 7 | 18 | 18 | 7 |
| | Median | 364 | 573 | 6 | 32.0 | 12.6 | 17.9 |
| | Mean | 438 | 666 | 10 | 33.0 | 12.3 | 19.3 |
| | SD | 263 | 287 | 8 | 7.2 | 6.8 | 4.0 |
| | CV% | 60 | 43 | 80 | 22 | 55 | 21 |
| Stage 3 | N | 12 | 7 | 7 | 12 | 12 | 7 |
| | Median | 488 | 660 | 10 | 29.9 | 12.8 | 19.5 |
| | Mean | 549 | 839 | 15 | 33.5 | 15.7 | 20.2 |
| | SD | 344 | 431 | 13 | 8.4 | 10.5 | 5.2 |
| | CV % | 63 | 51 | 86 | 25 | 67 | 26 |
| | | | Norketamine | | | | |
| Stage 1 | N | 18 | 17 | 17 | 18 | 18 | 17 |
| | Median | 328 | 367 | 11 | 28.0 | 9.85 | 21.0 |
| | Mean | 377 | 420 | 12 | 28.4 | 11.1 | 19.4 |
| | SD | 211 | 267 | 9 | 1.9 | 7.1 | 6.1 |
| | CV % | 56 | 64 | 80 | 7 | 64 | 31 |
| Stage 3 | N | 12 | 9 | 9 | 12 | 12 | 9 |
| | Median | 387 | 500 | 7 | 28.0 | 10.3 | 19.2 |
| | Mean | 486 | 624 | 7 | 31.1 | 13.4 | 17.9 |
| | SD | 323 | 307 | 5 | 6.9 | 9.0 | 5.3 |
| | CV % | 67 | 49 | 65 | 22 | 67 | 30 |

The results of PK linearity analysis are summarized in Table 2D below. The average AUC of ketamine per $cm^2$ patch over 24 hours was 3.62 and 4.17 ng·hour/mL for Stage 1 and Stage 3, with a coefficient of variation (CV %) of 39% and 47%, respectively.

TABLE 2D

Plasma AUC of Ketamine Normalized by the Product of Patch area ($cm^2$) and Duration (day) at Stages 1 and 3

| | Stage 1 AUC/(cm2 · d), (ng/mL · h)/(cm2 · d) | Stage 3 AUC/(cm2 · d), (ng/mL · h)/(cm2 · d) | Stage 3/Stage 1: |
|---|---|---|---|
| Median | 3.73 | 3.78 | 1.23 |
| Mean | 3.62 | 4.17 | 1.16 |
| CV % | 39 | 47 | 28 |
| 90% CI | — | — | (0.99-1.33) |

Pharmacodynamics:

Exploratory pharmacodynamic assessment of ketamine transdermal patch included assessment of treatment response based on the Montgomery-Asberg Depression Rating Scale (MADRS), Clinical Global Impressions-Severity (CGI-S), and Symptoms of Depression Questionnaire (SDQ) scores. Preliminary analysis of the exploratory PD results leads to the following conclusions:

Lower mean baseline total scores of the MADRS, SDQ, and CGI-S were observed from Stage 1 to Stage 3.

Improvements in the MADRS, SDQ, and CGI-S total scores compared to the corresponding baseline total scores were achieved at all post-patch application timepoints for all treatments.

At most timepoints for the MADRS, SDQ, and CGI-S, greater improvements in responses to depression scales were seen following high-dose and placebo patch application compared with those following low-dose ketamine patch application. Since this was a single cohort treated sequentially, the observed results may reflect a sequence effect, such that following the initial treatment with low-dose ketamine at Stage 1, subjects may have been more responsive to the intention to treat their depression during the following stages, rather than to the drug itself.

CGI-I ratings were between much improved (2) and no change (4) at all time points for all treatments. No clear trends in CGI-I scores were observed following placebo, ketamine low-dose, or ketamine high-dose application.

Major adverse events associated with ketamine (e.g. dissociation, dizziness, and effects on blood pressure) are generally transients and are observed in association with peak plasma concentrations. These side effects typically resolved after about 2 hours following a dose of 0.5 mg/kg 40 minutes IV infusion (Murrough et al., 2013; Singh et al, 2016; Lapidus et al, 2014; Singh et al, 2016; Diazgranados et al, 2010; Phillips et al., 2019; Daly et al., 2018).

Ketamine was generally safe and well tolerated in subjects at 20 mg and 40 mg doses. See Table 3 below. There were no adverse reactions noted at the patch application site. There were no deaths or SAEs reported during the study. One subject was discontinued due to a TEAE of worsening of depression, but received all study treatments prior to discontinuation. Slightly more than half (8/15) of all TEAEs during the study were considered by the Investigator as unrelated to the study drug. Following ketamine administration, 2 TEAEs (headache and diarrhoea) were considered by the Investigator as possibly related to the study drug and 1 TEAE (somnolence) was considered probably related to the study drug. The majority of the TEAEs reported during this study were mild in severity. There were no severe TEAEs reported. There were no clinically significant abnormal trends in laboratory parameters observed during the study. No notable mean changes from baseline or differences between treatments were observed for SBP, DBP, oxygen saturation, or temperature. Following ketamine high dose administration, a decrease in mean respiratory rate and an increase in HR compared to baseline were observed. No clinically significant PE findings were observed during the study. No trends in mean change from baseline in PR interval or QTcB interval were observed. Greater increases from baseline in mean RR interval were observed following ketamine high dose administration compared to ketamine low dose administration. There was no increase in QRS duration at any post-patch application timepoint. No significant differences in the OAA/S change from baseline composite score were observed between treatments at any timepoint. Post-patch application, there was no increase in the total score of the BPRS, the BPRS-Positive subscale, or the CADSS for either low-dose or high-dose ketamine, or placebo, indicating no emergence of dissociative or psychotomimetic symptoms following patch application.

TABLE 3

Treatment-Emergent Adverse Events by MedDRA Primary System Organ Class and Preferred Term During Treatment (Safety Population)

| System Organ Class Preferred Term | Stage 1: Ketamine Low-Dose (N = 18) | | Stage 2: Placebo (N = 15) | | Stage 3: Ketamine High-Dose (N = 12) | |
|---|---|---|---|---|---|---|
| | n (%) | # of Events | n (%) | # of Events | n (%) | # of Events |
| At least 1 TEAE | 3 (16.7) | 3 | 4 (26.7) | 4 | 4 (33.3) | 5 |
| Skin and subcutaneous tissue disorders | 0 | 0 | 1 (6.7) | 1 | 1 (8.3) | 2 |
| Dermatitis | 0 | 0 | 1 (6.7)) | 1 | 0 | 0 |
| Erythema | 0 | 0 | 0 | 0 | 1 (8.3) | 1 |
| Swelling face | 0 | 0 | 0 | 0 | 1 (8.3) | 1 |
| Gastrointestinal disorders | 1 (5.6) | 1 | 1 (6.7) | 1 | 0 | 0 |
| Diarrhoea | 1(5.6) | 1 | 1 (6.7) | 1 | 0 | 0 |
| Injury, poisoning, and procedural complications | 1 (5.6) | 1 | 0 | 0 | 1 (8.3) | 1 |
| Contusion | 1(5.6) | 1 | 0 | 0 | 1 (8.3) | 1 |
| Nervous system disorders | 1 (5.6) | 1 | 0 | 0 | 1 (8.3) | 1 |
| Headache | 0 | 0 | 0 | 0 | 1 (8.3) | 1 |
| Somnolence | 1 (5.6) | 1 | 0 | 0 | 0 | 0 |
| Cardiac disorders | 0 | 0 | 1 (6.7) | 1 | 0 | 0 |
| Tachycardia | 0 | 0 | 1 (6.7) | 1 | 0 | 0 |
| Infections and infestations | 0 | 0 | 1 (6.7) | 1 | 0 | 0 |
| Urinary tract infection | 0 | 0 | 1 (6.7) | 1 | 0 | 0 |
| Psychiatric disorders | 0 | 0 | 0 | 0 | 1 (8.3) | 1 |
| Depression | 0 | 0 | 0 | 0 | 1 (8.3) | 1 |

Abbreviations: MedDRA = Medical Dictionary for Regulatory Activities; TEAE = treatment-emergent adverse event.

The overall results suggest a significantly safer profile for ketamine patch at a predicted dose of up to 40 mg (actual mean dose~50 mg based on residual drug analysis) compared with that of a typical 40 min i.v. infusion or intranasal administration of ketamine. No or minimal observation for dizziness, sedation, dissociative effects, blood pressure elevations from administering the ketamine transdermal patches, comparing to about 70% prevalence of these AEs with IV infusion or Spravato.

Example 6. Ketamine Patches for Treating Depression

As shown herein, substantial reductions in MADRS from baseline were observed in all three stages of Example 5. Survey was conducted to collect ALL studies with the MADRS scale assessed after a single dose of ketamine or esketamine (Singh et al, A Double-Blind, Randomized, Placebo-Controlled, Dose-Frequency Study of Intravenous Ketamine in Patients With Treatment-Resistant Depression. Am J Psychiatry 2016 Aug. 1; 173(8):816-26; Murrough et al, Antidepressant Efficacy of Ketamine in Treatment-Resistant Major Depression: A Two-Site Randomized Controlled Trial. Am J Psychiatry. 2013 October; 170(10):1134-42; Lapidus et al, A Randomized Controlled Trial of Intranasal Ketamine in Major Depressive Disorder. Biol Psychiatry. 2014 Dec. 15; 76(12):970-6; Loo et al. Placebo-controlled Pilot Trial Testing Dose Titration and Intravenous, Intramuscular and Subcutaneous Routes for Ketamine in Depression. Acta Psychiatr Scand. 2016 July; 134(1):48-56; Singh et al, Intravenous Esketamine in Adult Treatment-Resistant Depression: A Double-Blind, Double-Randomization, Placebo-Controlled Study. Biol Psychiatry. 2016 Sep. 15; 80(6):424-431; Diazgranados et al, A Randomized Add-On Trial of an N-methyl-D-aspartate Antagonist in Treatment-Resistant Bipolar Depression. Arch Gen Psychiatry. 2010 August; 67(8):793-802; Phillips, et al, Single, Repeated, and Maintenance Ketamine Infusions for Treatment-Resistant Depression: A Randomized Controlled Trial. Am J Psychiatry. 2019 May 1; 176(5):401-409; FDA Briefing Document. Psychopharmacologic Drugs Advisory Committee (PDAC) and Drug Safety and Risk Management (DSaRM) Advisory Committee Meeting. Feb. 12, 2019). These reductions are substantial and in comparable or greater magnitude than the other ketamine or esketamine studies with other dosing methods (IV infusion or intranasal). As shown in FIGS. 6 and 7, antidepressant effects were observed in all stages of treatment, low dose (20 mg of ketamine base), placebo, or high dose (40 mg of ketamine base), and such effects were larger comparing to those typically seen in other ketamine studies.

Placebo stage (stage 2) also showed substantial decreases in MADRS (FIG. 6). Placebo effect in depression study is very normal. The large placebo drop shown in Example 5 were much larger than those from other studies as surveyed (FIG. 8). The explanation was called conditioned effect (on Stage 1). As shown in Example 5, the study was done in a sequential manner, with a low dose (28 mg, actual dose based on residue analysis) at Stage 1, followed by placebo (Stage 2), and then a high dose (about 53 mg, actual dose based on residue analysis) at Stage 3. The study was blinded to patients, meaning that patients did not know if they received a ketamine patch or a placebo patch. The significant antidepressant effect exerted at Stage 1 may bleed into Stage 2; in other words, the patients have experienced the antidepressant effects from Stage 1, therefore, the patients may have the expectation that they received the ketamine dose as well, thus psychologically approved their mood etc. This phenomenon is common in psychiatry field.

Importantly, the baseline dropped from Stage 1 to Stages 2 and 3 (FIG. 6). This indicated that administration of the ketamine transdermal patch produced a long-term antidepressant effects, even after ketamine or metabolites are completely cleared in the body.

CGI-S as another scale measuring antidepressant effect showed the similar effect as MADRS, including large drop from baseline, decreasing baseline from Stages 1 to 2 and 3. See FIG. 9.

As shown herein, the observed antidepressant effects following administration of ketamine transdermal patches were prolonged for the entire week, see e.g., FIG. 6. Typically after single dose of ketamine by IV infusion or intranasal spray, the antidepressant effect only lasted for about 3 days, and at the end of the week, the effect typically returns to baseline. The prolonged antidepressant effect is presumably due to the prolonged PK exposure of ketamine and HNK from administering the ketamine transdermal patches.

A correlation between the observed antidepressant effects and $C_{max}$ of ketamine and hydroxyketamine was also observed (see FIG. 10). Thus, the antidepressant effects can be further strengthened when the dose or concentration of ketamine and/or HNK increases. The relationship showed that when the concentration of ketamine or HNK increases to 20-30 ng/mL, the MADRS response reaches about the near maximal effects with dosing ketamine transdermal patches. As shown in FIG. 4, delivery of about 100 mg dose to a patient by applying ketamine transdermal patches for 24 hours will result a $C_{max}$ of around 30 ng/mL for ketamine and HNK with prolonged exposure over 24 hours or more. Thus, such higher dose is expected to further enhance the antidepressant effects.

In light of these results and observations, the following shows a new treatment of depression using ketamine transdermal patches and optionally placebo patches.

Specifically, a patient, who meets the Diagnostic and Statistical Manual of Mental Disorders, Fifth Edition (DSM-5) criteria for MDD based on the Structured Clinical Interview for DSM-5 (SCID-5), is treated with a ketamine transdermal patch (e.g., described herein). In some cases, the patient can be those who have failed >1 and <8 trials in the current episode per the Massachusetts General Hospital Antidepressant Treatment Response Questionnaire (MGH ATRQ) and/or have sub-optimal response defined as <50% response to current antidepressant treatment (≥8 weeks at an adequate and stable dose for at least 4 weeks) per the MGH ATRQ. The ketamine transdermal patch is applied to the patient for a duration of about 24 hours. The patient is delivered a dose of about 15 mg to about 100 mg of ketamine, such as about 20 mg, about 40 mg, about 50 mg, about 60 mg, about 80 mg, or about 100 mg, which can be supplied by one or more monolithic patches having a patch size of about 20 cm²-about 90 cm².

In some cases, the patient is treated chronically with the ketamine transdermal patch. In such cases, the ketamine transdermal patches are typically applied to the patient once or twice a week, with the duration of each application about 24 hours, or in some cases can be up to 48 or 72 hours. In some cases, the patient can be administered placebo patches (e.g., described herein) in between the ketamine transdermal patches. Using a once a week dosing regimen as an example, the patient can be treated with a first ketamine transdermal patch for 24 hours on day 1, after which, the first ketamine transdermal patch is removed, which is followed by no treatment until a week later, on day 8, either a substantially the same ketamine transdermal patch or a substantially the same placebo patch (except without the ketamine) is applied to the patient for 24 hours, and so on. In some cases, the patient can be administered a ketamine transdermal patch, followed by no treatment (no ketamine or placebo patch) for a period ranging from 1 week to 6 weeks, before administering the next treatment, which can also be either a substantially the same ketamine transdermal patch or a substantially the same placebo patch (except without the ketamine), although in such dosing regimen, it is preferred not to use placebo patches after the no treatment period.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A transdermal delivery device comprising a drug-in-adhesive layer, wherein the drug-in-adhesive layer comprises:
   (a) ketamine in an amount of 14-17% by weight;
   (b) oleyl oleate and levulinic acid, each in an amount of 4-7% by weight;
   (c) a polyvinyl pyrrolidone-co-vinyl acetate in an amount of 15-25% by weight;
   (d) a carboxylate-functionalized polyacrylate-vinylacetate copolymer in an amount of 45-55% by weight, wherein the carboxylate-functionalized polyacrylate-vinylacetate copolymer is a copolymer of 2-ethyl hexyl acrylate, vinyl acetate, butyl acrylate, acrylic acid, and tert octyl acrylamide; and
   (e) an antioxidant in an amount of 0.3-0.7% by weight, wherein the transdermal delivery device has a ketamine flux of about 0.1-1 mg/cm$^2$/day and is storage stable for about 24 months, or longer, when stored at room temperature at 60% relative humidity±5% RH, or storage stable for about 6 months, or longer, when stored at 40±2° C. at 75% relative humidity (RH)±5% RH, wherein the drug-in-adhesive layer does not have any visible ketamine particles or crystals by polarized microscope after the transdermal delivery device is stored at room temperature (25±2° C.) at 60% relative humidity (RH)±5% RH for about 24 months or longer or at 40±2° C. at 75% relative humidity (RH)±5% RH for about 6 months or longer.

2. The transdermal delivery device of claim 1, wherein the drug-in-adhesive layer comprises:
   (a) ketamine in an amount of 15% to 16% by weight;
   (b) oleyl oleate and levulinic acid, each in an amount of 5-6% by weight;
   (c) the polyvinyl pyrrolidone-co-vinyl acetate in an amount of 20-25% by weight;
   (d) the carboxylate-functionalized polyacrylate-vinylacetate copolymer in an amount of 50-55% by weight; and
   (e) the antioxidant in an amount of 0.3-0.7% by weight.

3. The transdermal delivery device according to claim 1, wherein the drug-in-adhesive layer is homogenous.

4. The transdermal delivery device according to claim 1, which has an active surface area of about 10 cm$^2$ to about 180 cm$^2$.

5. The transdermal delivery device according to claim 1, which has a total ketamine load of about 0.5 mg/cm$^2$ to about 2 mg/cm$^2$.

6. The transdermal delivery device according to claim 1, which is capable of adhering to the skin of a subject for a period of time ranging from 8 hours to about 168 hours.

7. The transdermal delivery device of claim 6, which is capable of continuously delivering ketamine to the subject during the period of time when the transdermal delivery device adheres to the skin of the subject, at a substantially constant rate ranging from about 0.1 mg/cm$^2$/day to about 1 mg/cm$^2$/day.

8. A kit comprising:
   (a) one or more transdermal delivery devices comprising ketamine according to claim 1; and
   (b) one or more placebo transdermal delivery devices, wherein each of the placebo transdermal delivery devices is substantially the same as each of the transdermal delivery devices comprising ketamine, except that the placebo transdermal delivery device does not contain ketamine.

9. The transdermal delivery device according to claim 1, which is in a form of a monolithic patch, wherein the monolithic patch has
   (a) an active surface area of about 20 cm$^2$, which contains ketamine in the amount of about 24.7 mg, and can deliver a dose of ketamine at a rate of about 6-16 mg/day for about 1 day, 2 days, or 3 days,
   (b) an active surface area of about 40 cm$^2$, which contains ketamine in the amount of about 49.6 mg, and can deliver a dose of ketamine at a rate of about 10-30 mg/day, for about 1 day, 2 days, or 3 days,
   (c) an active surface area of about 60 cm$^2$, which contains ketamine in the amount of about 87.3 mg, and can deliver a dose of ketamine at a rate of about 20-40 mg/day, for about 1 day, 2 days, or 3 days,
   (d) an active surface area of about 80 cm$^2$, which contains ketamine in the amount of about 100 mg, and can deliver a dose of ketamine at a rate of about 25-50 mg/day, for about 1 day, 2 days, or 3 days,
   (e) an active surface area of about 90 cm$^2$, which contains ketamine in the amount of about 112.5 mg, and can deliver a dose of ketamine at a rate of about 30-60 mg/day, for about 1 day, 2 days, or 3 days,
   (f) an active surface area of about 100 cm$^2$, which contains ketamine in the amount of about 124.7 mg, and can deliver a dose of ketamine at a rate of about 35-70 mg/day, for about 1 day, 2 days, or 3 days,
   (g) an active surface area of about 120 cm$^2$, which contains ketamine in the amount of about 150 mg, and can deliver a dose of ketamine at a rate of about 40-80 mg/day, for about 1 day, 2 days, or 3 days, or
   (h) an active surface area of about 180 cm$^2$, which contains ketamine in the amount of about 225 mg, and can deliver a dose of ketamine at a rate of about 60-110 mg/day, for about 1 day, 2 days, or 3 days.

* * * * *